US010767230B2

(12) United States Patent
Too et al.

(10) Patent No.: US 10,767,230 B2
(45) Date of Patent: Sep. 8, 2020

(54) MICRORNA BIOMARKER FOR THE DIAGNOSIS AND TREATMENT OF GASTRIC CANCER

(71) Applicants: Agency for Science, Technology and Research, Singapore (SG); National University of Singapore, Singapore (SG); National University Hospital (Singapore) Pte Ltd, Singapore (SG)

(72) Inventors: Heng-phon Too, Singapore (SG); Lihan Zhou, Singapore (SG); Ruiyang Zou, Singapore (SG); Khay Guan Yeoh, Singapore (SG); Bok Yan So, Singapore (SG); Feng Zhu, Singapore (SG); Wei Peng Yong, Singapore (SG)

(73) Assignees: Agency for Science, Technology and Research, Singapore (SG); National University of Singapore, Singapore (SG); National University Hospital (Singapore) Pte Ltd., Singapore (SG)

( * ) Notice: Subject to any disclaimer, the term of this patent is extended or adjusted under 35 U.S.C. 154(b) by 508 days.

(21) Appl. No.: 15/501,691

(22) PCT Filed: Aug. 11, 2015

(86) PCT No.: PCT/SG2015/050256
§ 371 (c)(1),
(2) Date: Feb. 3, 2017

(87) PCT Pub. No.: WO2016/022076
PCT Pub. Date: Feb. 11, 2016

(65) Prior Publication Data
US 2017/0233822 A1    Aug. 17, 2017

(30) Foreign Application Priority Data

Aug. 7, 2014 (SG) .......................... 10201404742W

(51) Int. Cl.
*C12Q 1/6886* (2018.01)
*G16B 25/00* (2019.01)
*G16B 20/00* (2019.01)
*G01N 33/574* (2006.01)
*G16H 50/20* (2018.01)

(52) U.S. Cl.
CPC ..... *C12Q 1/6886* (2013.01); *G01N 33/57407* (2013.01); *G16B 20/00* (2019.02); *G16B 25/00* (2019.02); *G16H 50/20* (2018.01); *C12Q 2600/106* (2013.01); *C12Q 2600/112* (2013.01); *C12Q 2600/118* (2013.01); *C12Q 2600/158* (2013.01); *C12Q 2600/16* (2013.01); *C12Q 2600/178* (2013.01); *G01N 2800/50* (2013.01)

(58) Field of Classification Search
None
See application file for complete search history.

(56) References Cited

U.S. PATENT DOCUMENTS

2013/0065769 A1    3/2013 Wong

FOREIGN PATENT DOCUMENTS

| CN | 101988059 A | 3/2011 |
|---|---|---|
| CN | 102007223 A | 4/2011 |
| CN | 103773761 A | 5/2014 |
| JP | 2013085542 A | 5/2013 |
| WO | WO-2009/108853 A1 | 9/2009 |
| WO | WO-2009/147656 A1 | 12/2009 |
| WO | WO-2012/010584 A1 | 1/2012 |
| WO | WO-2015052526 A1 * | 4/2015 |

OTHER PUBLICATIONS

Liu, Rui, et al. "A five-microRNA signature identified from genome-wide serum microRNA expression profiling serves as a fingerprint for gastric cancer diagnosis." European journal of cancer 47.5 (2011): 784-791.*

Benjamini, Y. and Hochberg, Y., Controlling the false discovery rate: A practical and powerful approach to multiple testing, J.R. Statist. Soc. B, 57(1): 289-300 (1995).

Blanco-Calvo, M. et al., Circulating microRNAs: molecular microsensors in gastrointestinal cancer, Sensors, 12(7): 9349-9362 (2012).

Cai, H. et al., Plasma microRNAs serve as novel potential biomarkers for early detection of gastric cancer, Medical Oncology, 30(1): 452 1-7 (2013).

Cissell, K.A. and Deo, S.K., Trends in microRNA detection, Anal Bioanal Chem, 394(4): 1109-1116 (2009).

Cortez, M.A. et al., MicroRNAs in body fluids—the mix of hormones and biomarkers, Nat Rev Clin Oncol, 8(8): 467-477 (2011).

Cui, M-H. et al., Upregulation of micro RNA 181 c expression in gastric cancer tissues and plasma. Asian Pacific journal of cancer prevention: Asian Pacific Journal of Cancer Prevention, 14(5): 3063-3066 (2013).

(Continued)

*Primary Examiner* — G Steven Vanni
(74) *Attorney, Agent, or Firm* — Choate, Hall & Stewart LLP; Brian E. Reese; Dana M. Daukss

(57) ABSTRACT

Disclosed are methods of determining the likelihood of a subject having or developing a gastric cancer. The methods comprise measuring the expression level of at least one miRNA having at least 90% sequence identity with an miRNA as described herein in a non-cellular biofluid sample obtained from the subject, wherein differential expression of miRNA expression in the sample obtained from the subject, as compared to a control, may be indicative of the subject having gastric cancer and wherein the miRNA may be either an miRNA listed as "up-regulated" or an miRNA listed as "down-regulated". Also disclosed is a method of determining the likelihood of a subject having or developing a stage of a gastric cancer.

4 Claims, 11 Drawing Sheets
Specification includes a Sequence Listing.

(56) References Cited

OTHER PUBLICATIONS

Etheridge, A. et al., Extracellular microRNA: a new source of biomarkers, Mutat Res, 717(1-2): 85-90 (2011).

Ferlay, J. et al., Estimates of worldwide burden of cancer in 2008: GLOBOCAN 2008, Int J Cancer, 127(12): 2893-2917 (2010).

Gao, M. et al., Clinical application of micro RNA in gastric cancer in Eastern Asian area, World J. Gastroenterol, 19(13): 2019-2027 (2013).

Gong, H. et al., Characterization of photosystem II in salt-stressed cyanobocterial Spirulina platensis cells, Biochimica et Biophysica Acta, 1777(6): 488-495 (2008).

Gorur, A. et al., Determination of plasma microRNA for early detection of gastric cancer, Mol Biol Rep, 40(3): 2091-2096 (2013).

Hindson, B.J. et al., High-throughput droplet digital PCR system for absolute quantitation of DNA copy number, Anal Chem, 83(22): 8604-8610 (2011).

International Search Report for PCT/SG2015/050256, 9 pages (dated Oct. 30, 2015).

Jemal, A. et al., Global cancer statistics, CA Cancer J Clin., 61(2): 69-90 (2011).

Kim, S.Y. et al., Validation of Circulating miRNA Biomarkers for Predicting Lymph Node Metastasis in Gastric Cancer, The Journal of Molecular Diagnosis, 15(5):661-669 (2013).

Li, B-s., et al., Plasma microRNAs, miR-223, miR-21 and miR-218, as Novel Potential Biomarkers for Gastric Cancer Detection, PloS ONE, 7(7): e41629 1-8 (2012).

Li, B. et al., Analysis of connection networks among miRNAs differentially expressed in early gastric cancer for disclosing some biological features of disease development, Gene, 548:159-165 (2014).

Li, C. et al., miRNA-199a-3p in plasma as a potential diagnostic biomarker for gastric cancer, Ann Surg Oncol, 20: S397-S405 (2013).

Li, C. et al., MiRNA-199a-3p: A potential circulating diagnostic biomarker for early gastric cancer, Journal of Surgical Oncology, 108(2): 89-92 (2013).

Li, Y. and Kowdley, K.V., Method for microRNA isolation from clinical serum samples, Anal Biochem, 431(1): 69-75 (2012).

Liang, H. et al., The origin, function, and diagnostic potential of extracellular microRNAs in human body fluids, Wiley Interdiscip Rev RNA, 5(2): 285-300 (2014).

Liu, H. et al., Genome-wide microRNA profiles identify miR-378 as a serum biomarker for early detection of gastric cancer, Cancer Lett, 316(2): 196-203 (2012). Accepted Manuscript, 38 pages (2011).

Liu, R. et al., A five-microRNA signature identified from genome-wide serum microRNA expression profiling serves as a fingerprint for gastric cancer diagnosis, European Journal of Cancer, 47(5):784-791 (2011).

Lo, S-S. et al., Overexpression of miR-370 and down regulation of its novel target TGFβ-RII contribute to the progression of gastric carcinoma, Oncogene, 31(2): 226-237 (2012).

Mabert, K. et al., Cancer biomarker discovery: current status and future perspectives, Int J Radiat Biol, Accepted Manuscript, 49 pages (2014).

Redova, M. et al., Circulating miRNAs as new blood-based biomarkers for solid cancers, Future Oncol, 9(3): 387-402 (2013).

Saeys, Y. et al., A review of feature selection techniques in bioinformatics, Bioinformatics, 23(19): 2507-2517 (2007).

Song, J. et al., Identification of Suitable Reference Genes for qPCR Analysis of Serum microRNA in Gastric Cancer Patients, Digestive Diseases and Sciences, 57:897-904 (2012).

Song, M-y. et al, Identification of serum microRNAs as novel non-invasive biomarkers for early detection of gastric cancer, PloS ONE, 7(3): e33608 1-9 (2012).

Tong, F. et al., MicroRNAs in gastric cancer: from bench top to bedside, Dig Dis Sci, 59(1): 24-30 (2014).

Tsongalis, G.J. et al., MicroRNA Analysis: Is It Ready for Prime Time? Clinical Chemistry, 59(2): 343-347 (2013).

Tsujiura, M. et al., Circulating microRNAs in plasma of patients with gastric cancers, British Journal of Cancer, 102(7): 1174-1179 (2010).

Ueda, T. et al., Relation between microRNA expression and progression and prognosis of gastric cancer: a microRNA expression analysis, Lancet Oncology, 11(2):136-146 (2010).

Uedo, N. et al., Screening and Treating Intermediate Lesions to Prevent Gastric Cancer, Gastroenterol Clin N Am., 42(2): 317-335 (2013).

Valladares-Ayerbes, M. et al., Circulating miR-200c as a diagnostic and prognostic biomarker for gastric cancer, Journal of Translational Medicine, 10:186 1-14 (2012).

Written Opinion for PCT/SG2015/050256, 10 pages (dated Oct. 30, 2015).

Wu, H-H. et al., Advances in molecular biomarkers for gastric cancer: miRNAs as emerging novel cancer markers, Expert Reviews in Molecular Medicine, 16: e1 1-18 (2014).

Xiong, M. et al., Biomarker identification by feature wrappers, Genome Res., 11(11): 1878-1887 (2001).

Zhang, W-H. et al., The Identification of miR-375 as a Potential Biomarker in Distal Gastric Adenocarcinoma, Oncology Research, 20(4): 139-147 (2012).

Zhang, X. et al., Combination of hsa-miR-375 and hsa-miR-142-5p as a predictor for recurrence risk in gastric cancer patients following surgical resection, Annals of Oncology, 22(10):2257-2266 (2011).

Zheng, G. et al., A two-microRNA signature as a potential biomarker for early gastric cancer, Oncology Letters, 7:679-684 (2014).

Liu, T. et al., MicroRNA-27a functions as an oncogene in gastric adenocarcinoma by targeting prohibitin, Cancer Lett, 273(2):233-242 (2009).

* cited by examiner

Black – Gastric cancer subjects
White – normal subjects

Black – Gastric cancer subjects
White – normal subjects

Majority of gastric cancer subjects

MICRORNA BIOMARKER FOR THE DIAGNOSIS AND TREATMENT OF GASTRIC CANCER

CROSS-REFERENCE TO RELATED APPLICATIONS

This patent application is a National Stage Entry of International Patent Application No. PCT/SG2015/050256, filed on Aug. 11, 2015 which claims the benefit of priority of Singapore patent application No. 10201404742W, filed 7 Aug. 2014, the contents of each of which are hereby incorporated by reference in their entirety for all purposes herein.

FIELD OF THE INVENTION

The present invention relates to biochemistry in particular biomarkers. In particular, the present invention relates to biomarkers associated with cancer and methods of using the biomarkers to determine the likelihood that a patient suffers from cancer, such as gastric cancer.

BACKGROUND OF THE INVENTION

Gastric cancer is the 4th most common cancer (>1 million cases per year) and the 2nd most common cause of cancer deaths worldwide. Prognosis of gastric cancer is poor, with a less than 10% 5-year survival rate, largely because the condition is usually presented at an advanced state of the disease. Hence, to improve the clinical outcomes, early detection and accurate monitoring of the disease is necessary. Currently, endoscopy is the only reliable method for early diagnosis but it is limited as a screening test due to the high cost and risk. A less invasive screening test for gastric cancer is highly desirable and should reduce unnecessary endoscopy.

Thus, the present invention provides an alternative method of detecting gastric cancer.

SUMMARY OF THE INVENTION

In one aspect, there is provided a method of detecting or diagnosing gastric cancer in a subject or determining the likelihood of a subject developing gastric cancer, the method comprising: determining an expression level of at least one miRNA having at least 90% sequence identity with an miRNA in a non-cellular biofluid sample obtained from the subject, wherein differential expression of the miRNA expression, as compared to a control, is indicative of the subject having gastric cancer, and wherein the miRNA is either an "up-regulated" miRNA selected from the group consisting of hsa-miR-142-5p, hsa-miR-29c-3p, hsa-miR-93-5p, hsa-miR-140-5p, hsa-miR-148a-3p, hsa-miR-183-5p, hsa-miR-29b-3p, hsa-miR-424-5p, hsa-miR-101-3p, hsa-miR-106b-3p, hsa-miR-128, hsa-miR-1280, hsa-miR-140-3p, hsa-miR-15b-3p, hsa-miR-186-5p, hsa-miR-18b-5p, hsa-miR-197-3p, hsa-miR-19a-3p, hsa-miR-19b-3p, hsa-miR-20b-5p, hsa-miR-21-3p, hsa-miR-23a-5p, hsa-miR-25-3p, hsa-miR-27a-5p, hsa-miR-29a-3p, hsa-miR-29b-2-5p, hsa-miR-29c-5p, hsa-miR-338-5p, hsa-miR-425-3p, hsa-miR-4306, hsa-miR-450a-5p, hsa-miR-486-5p, hsa-miR-500a-3p, hsa-miR-501-5p, hsa-miR-532-3p, hsa-miR-550a-5p, hsa-miR-579, hsa-miR-589-5p, hsa-miR-590-5p, hsa-miR-598, hsa-miR-616-5p, hsa-miR-627, hsa-miR-629-3p, hsa-miR-629-5p, hsa-miR-93-3p, hsa-miR-195-5p, hsa-miR-18a-3p, hsa-miR-363-3p, hsa-miR-181a-2-3p, hsa-miR-16-5p, hsa-miR-501-3p, hsa-miR-23a-3p, hsa-miR-339-3p, hsa-miR-15a-5p, hsa-miR-320b, hsa-miR-374b-5p, hsa-miR-650, hsa-miR-1290, hsa-miR-22-3p, hsa-miR-320c, hsa-miR-130a-3p, hsa-miR-320e, hsa-miR-378a-3p, hsa-miR-9-5p, hsa-miR-200b-3p, hsa-miR-141-3p, hsa-miR-191-5p, hsa-miR-628-5p, hsa-miR-484, hsa-miR-425-5p; or a "down-regulated" miRNA selected from the group consisting of hsa-miR-103a-3p, hsa-miR-30a-5p, hsa-miR-181a-5p, hsa-miR-107, hsa-miR-26a-5p, hsa-miR-126-3p, hsa-miR-99b-5p, hsa-miR-339-5p, hsa-miR-122-5p, hsa-miR-136-5p, hsa-miR-139-5p, hsa-miR-146a-5p, hsa-miR-154-5p, hsa-miR-193b-3p, hsa-miR-23c, hsa-miR-30b-5p, hsa-miR-337-5p, hsa-miR-382-5p, hsa-miR-409-3p, hsa-miR-411-5p, hsa-miR-485-3p, hsa-miR-487b, hsa-miR-495, hsa-miR-885-5p, hsa-miR-99a-5p, hsa-miR-362-5p, hsa-miR-671-3p, hsa-miR-454-3p, hsa-miR-328, hsa-miR-320a, hsa-miR-126-5p, hsa-miR-27a-3p, hsa-miR-30d-5p, hsa-miR-10a-5p, hsa-miR-10b-5p, hsa-miR-497-5p, hsa-miR-134, and hsa-miR-150-5p.

In another aspect, there is provided a method of detecting or diagnosing gastric cancer stage in a subject or determining the likelihood of a subject having a stage of a gastric cancer, the method comprising: determining the expression level of at least one microRNA (miRNA) having at least 90% sequence identity with an miRNA as listed in at least one of the tables selected from the group consisting of Table 8, Table 15, Table 16, and Table 17, in a non-cellular biofluid sample obtained from the subject; and wherein differential expression of miRNA expression in the sample, as compared to a control, diagnoses the subject to have any one of stage 1, stage 2, stage 3 or stage 4 gastric cancer.

In yet another aspect, there is provided a method of detecting or diagnosing gastric cancer in a subject, comprising the steps of: (a) measuring an expression level of at least one miRNA in a non-cellular biofluid sample, wherein the miRNA has at least 90% sequence identity with an miRNA selected from the group consisting of hsa-miR-103a-3p, hsa-miR-142-5p, hsa-miR-29c-3p, hsa-miR-30a-5p, hsa-miR-107, hsa-miR-26a-5p, hsa-miR-140-5p, hsa-miR-148a-3p, hsa-miR-29b-3p, hsa-miR-126-3p, hsa-miR-181a-5p, hsa-miR-27a-5p, hsa-miR-616-5p, hsa-miR-484, hsa-miR-4306, hsa-miR-590-5p, hsa-miR-362-5p, hsa-miR-106b-3p, hsa-miR-497-5p, hsa-miR-18b-5p, hsa-miR-122-5p, hsa-miR-200b-3p, hsa-miR-197-3p, hsa-miR-486-5p, hsa-miR-99a-5p, hsa-miR-885-5p, hsa-miR-598, hsa-miR-454-3p, hsa-miR-130a-3p, hsa-miR-150-5p, hsa-miR-30d-5p, hsa-miR-10b-5p, hsa-miR-532-3p, hsa-miR-23a-5p, hsa-miR-21-3p, hsa-miR-136-5p, hsa-miR-1280, and hsa-miR-16-5p; (b) generating a score based on the expression level of the miRNAs measured in step (a); and (c) using the score to predict the likelihood of the subject having gastric cancer, wherein the score is calculated by a classification algorithm that compares the expression level of the subject with that of a positive control (sample from gastric cancer subject) or a negative control (sample from gastric cancer free subject), and wherein the score identifies the likelihood of the subject to either: i. have gastric cancer, which score would fall within the score of the positive control, or ii. have no gastric cancer (gastric cancer free), which score would fall within the score of the negative control.

BRIEF DESCRIPTION OF THE DRAWINGS

The invention will be better understood with reference to the detailed description when considered in conjunction with the non-limiting examples and the accompanying drawings, in which:

FIG. 2 shows the steps occurred in the process from isolation of total miRNA from clinical sample to eventual data processing and statistical analysis. As illustrated in FIG. 2, clinical samples are first subjected to the step of "isolation", which refers to the isolation and purification of miRNA from samples, such as serum of a patient. Next, samples are added with spike-in miRNA, which are non-natural synthetic miRNAs mimics (i.e. small single-stranded RNA with length range from 22 to 24 bases). These spike-in miRNA are added into samples to monitor the efficiencies at various steps including isolation, reverse transcription, augmentation and qPCR. Next, miRNA are divided to a number of multiple groups. This step is referred to as "multiplex design", where miRNA assays were deliberately divided into a number of multiplex groups (45 to 65 miRNA per group) in silico to minimize non-specific amplifications and primer-primer interaction during the RT and augmentation processes. Next, samples go through "multiplex reverse transcription" process where various pools of reverse transcription primers were combined and added to different multiplex groups to generate cDNA. Upon generation of cDNA, a pool of PCR primers are combined with each of the cDNA pool generated (from a certain multiplex croup) and an optimized touch down PCR is carried out to enhance the amount of total cDNAs in the group simultaneously. This step of enhancement of the amount of total (all) cDNAs is referred to as "augmentation" step. After augmentation and before data processing and statistical analysis, the augmented cDNA undergoes a single-plex qPCR, which refers to the step where the augmented cDNA pools are distributed in to various wells in the 384 plates and single-plex qPCR reactions are then carried out. At the same time as measurements of miRNA in clinical samples, synthetic miRNA standard curves are measured together to obtain interpolation of absolute copy numbers in all the measurements. Thus, FIG. 2 provides a detailed step by step workflow of miRNA sample processing that occurred in the Experimental section below.

FIG. 3 shows a heat-map representation of all reliably detected miRNAs (as listed in Table 4); the expression levels (copy/ml) of miRNAs were presented in log 2 scale and standardized to zero mean. The color of the points represented the concentrations. Hierarchical clustering was carried out for both dimensions (the miRNAs and the samples) based on the Euclidean distance. For the horizon dimension: black represents gastric cancer subjects and white represents normal/control subjects.

FIG. 6 and FIG. 7 show large numbers of cancer related and non-related miRNAs are found to be positively correlated, which makes the choice of the best miRNA combinations for gastric cancer diagnosis challenging.

FIG. 8 shows the receiver operating characteristic curves of top (based on AUC, which is the area under the receiver operating characteristic curve) up-regulated (row 1) and down-regulated (row 2) miRNAs in the various stages of gastric cancer subjects as compared to miRNAs in normal/control subjects.

FIG. 9 shows that the miRNAs used for determining the various stages of gastric cancer appear to be specific for the stages they are correlated to, with the exception of large overlap observed in both Stage 3 and Stage 4, which is expected as these two stages are clinically closely related.

FIG. 10 shows the robustness of the data obtained from the various multivariant biomarker panels.

FIG. 11 shows the differences in the AUC between the various numbers of miRNAs in a multivariant biomarker panel set.

BRIEF DESCRIPTION OF THE TABLES

Figure 1:
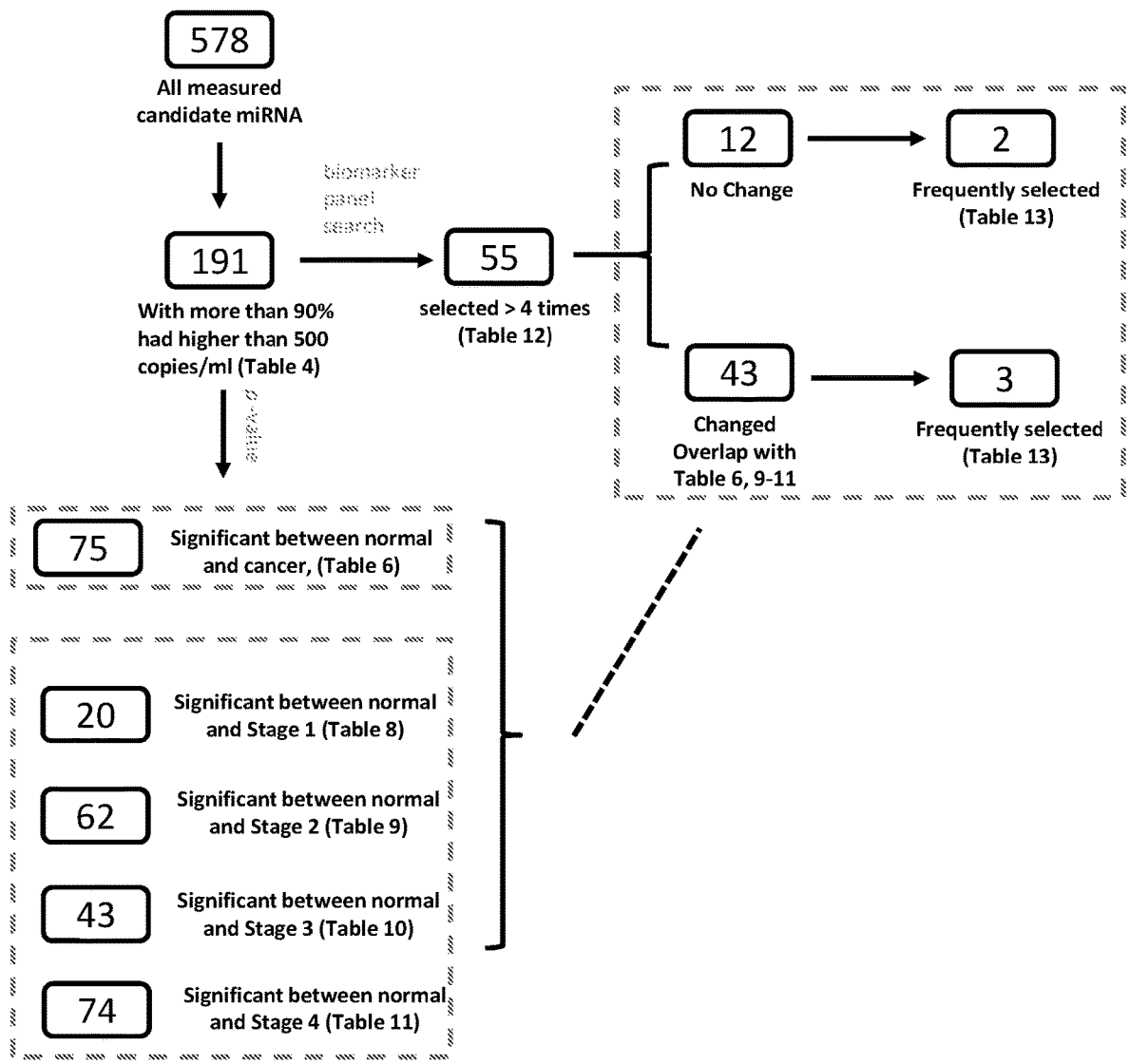
FIG. 1 shows a schematic diagram of the division of miRNAs detected in patients with gastric cancer.

The invention will be better understood with reference to the detailed description when considered in conjunction with the non-limiting examples and the accompanying tables, in which:

Table 1 shows a summary of serum/plasma microRNA biomarker studies for gastric cancer. Table 1 summarizes various studies that measure the level of miRNAs in cell-free serum/plasma samples. Only results validated with RT-qPCR are listed in this table. "GC" refers to gastric cancer subjects and "C" refers to control subjects.

Table 2 shows the clinical information of gastric cancer subjects analyzed in the Experiment section of the present disclosure. All serums were collected from 236 gastric cancer subjects before any treatment and stored at −80° C. prior to use. The status of *H. pylori* infection is also indicated in column labelled "H pylori", which refers to *Helicobacter pylori*.

Table 3 shows the clinical information of normal subjects (control). All normal/control subject s (237 subjects) were confirmed gastric cancer free by endoscopy at the time the samples were collected. Subjects were followed up for 3-5 years with endoscopy screening every 2 years to ensure the subjects did not develop gastric cancer within this period of time. All serums were stored at −80° C. prior to use. The status of *H. pylori* infection is also indicated in column labelled "H pylori", which refers to *Helicobacter pylori*.

Table 4 shows the sequences of 191 miRNA reliably detected in the serum samples of both gastric cancer subjects and normal subjects (control). An miRNA is considered "reliably detected" when at least 90% of the serum samples had a concentration higher than 500 copies per ml. The miRNAs were named according to the miRBase V18 release.

Table 5 shows a summary of the characteristics of both gastric cancer subjects and healthy control (normal subjects/control).

Table 6 lists miRNAs that are differentially expressed in normal subject (control) and gastric cancer subjects. For the comparison between normal/control and all gastric cancer subjects (regardless of subtypes and stages), 75 miRNA had p-value lower than 0.01 after false discovery rate correction (Bonferroni method). AUC—area under the receiver operating characteristic curve; fold change—the mean expression level (copy/ml) of miRNA in the cancer population divided by that in the normal/control population.

Table 7 shows the comparison between the current study and other literature reports. MiRNAs not listed in Table 4 (i.e. miRNAs with expression level of ≥500 copies/ml) were considered to be below detection limit of the study (N.D.). Thus, Table 7 shows the majority of the purported differentially regulated miRNA in the art are different from the exemplary miRNA of the present disclosure.

Table 8 lists miRNAs that are differentially expressed between normal subjects (control) and stage 1 gastric cancer subjects. For the comparison between normal/control and stage 1 gastric cancer subjects, 20 miRNA had p-value lower than 0.01 after false discovery rate correction (Bonferroni method). AUC—area under the receiver operating characteristic curve; fold change—the mean expression level (copy/ml) of miRNA in the cancer population divided by that in the normal/control population.

Table 9 lists miRNAs that are differentially expressed between normal subjects (control) and stage 2 gastric cancer subjects. For the comparison between normal/control and stage 2 gastric cancer subjects, 62 miRNA had p-value lower than 0.01 after false discovery rate correction (Bonferroni method). AUC—area under the receiver operating characteristic curve; fold change—the mean expression level (copy/ml) of miRNA in the cancer population divided by that in the normal/control population.

Table 10 lists miRNAs that are differentially expressed between normal subjects (control) and stage 3 gastric cancer subjects. For the comparison between normal/control and stage 3 gastric cancer subjects, 43 miRNA had p-value lower than 0.01 after false discovery rate correction (Bonferroni method). AUC—area under the receiver operating characteristic curve; fold change—the mean expression level (copy/ml) of miRNA in the cancer population divided by that in the normal/control population.

Table 11 lists miRNAs that are differentially expressed between normal subjects (control) and stage 4 gastric cancer subjects. For the comparison between normal/control and stage 4 gastric cancer subjects, 74 miRNA had p-value lower than 0.01 after false discovery rate correction (Bonferroni method). AUC—area under the receiver-operating characteristic curve; fold change—the mean expression level (copy/ml) of miRNA in the cancer population divided by that in the normal/control population.

Table 12 lists miRNAs that are identified in the multivariant biomarker panel identification process. The identities of the miRNAs selected for the assembly of biomarker panels with 6, 7, 8, 9, and 10 miRNA were summarized. Prevalence was defined by the counts of the miRNA in all panels divided by the total number of panels. The panels with the top 10% and bottom 10% AUC were excluded to avoid counting of falsely discovered biomarkers due to fitting of inaccurate data from subpopulations generated by the randomization process in cross-validation analysis. Only the miRNAs with 4 or more counts among were listed. The changes of the miRNAs in various stages of gastric cancers were defined based on Table 6, 8-11.

Table 13 shows the statistics of the occurrence of miRNAs frequently selected in the multivariant biomarker panel selection process. The percentage of miRNA panels using different numbers of miRNAs from the two miRNAs groups: hsa-21-5p, hsa-103a-3p and hsa-20a-5p group, and the hsa-532-5p and hsa-30e-5p group. The top 10% and bottom 10% of the 6, 7, 8, 9, 10 miRNA biomarker panels defined by the AUC in the validation set (FIG. 10) were excluded for counting.

Table 14 lists miRNAs that are differentially expressed between normal/control and gastric cancer (regardless of stages), which were not previously reported in the art (which are listed in Table 1).

Table 15 lists miRNAs that are differentially expressed between normal/control and stage 2 gastric cancer, which were not previously reported in the art.

Table 16 lists miRNAs that are differentially expressed between normal/control and stage 3 gastric cancer, which were not previously reported in the art.

Table 17 lists miRNAs that are differentially expressed between normal/control and stage 4 gastric cancer, which were not previously reported in the art.

Table 18 lists miRNAs that are differentially expressed between normal/control and either stage 1, stage 2, stage 3, stage 4 or all stages of gastric cancer, which were not previously reported in the art. Table 18 is a combination of Table 14, Table 8, Table 15, Table 16 and Table 17.

Table 19 lists miRNAs frequently selected for use in multivariant biomarker panel where the expression levels of the miRNAs were altered in the gastric cancer subjects (i.e. significant group from Table 12), which were not previously reported in the art.

Table 20 lists miRNAs frequently selected for use in multivariant biomarker panel where the expression levels of the miRNAs were not altered in the gastric cancer subjects (i.e. insignificant group from Table 12), which were not previously reported in the art.

Figure 15:
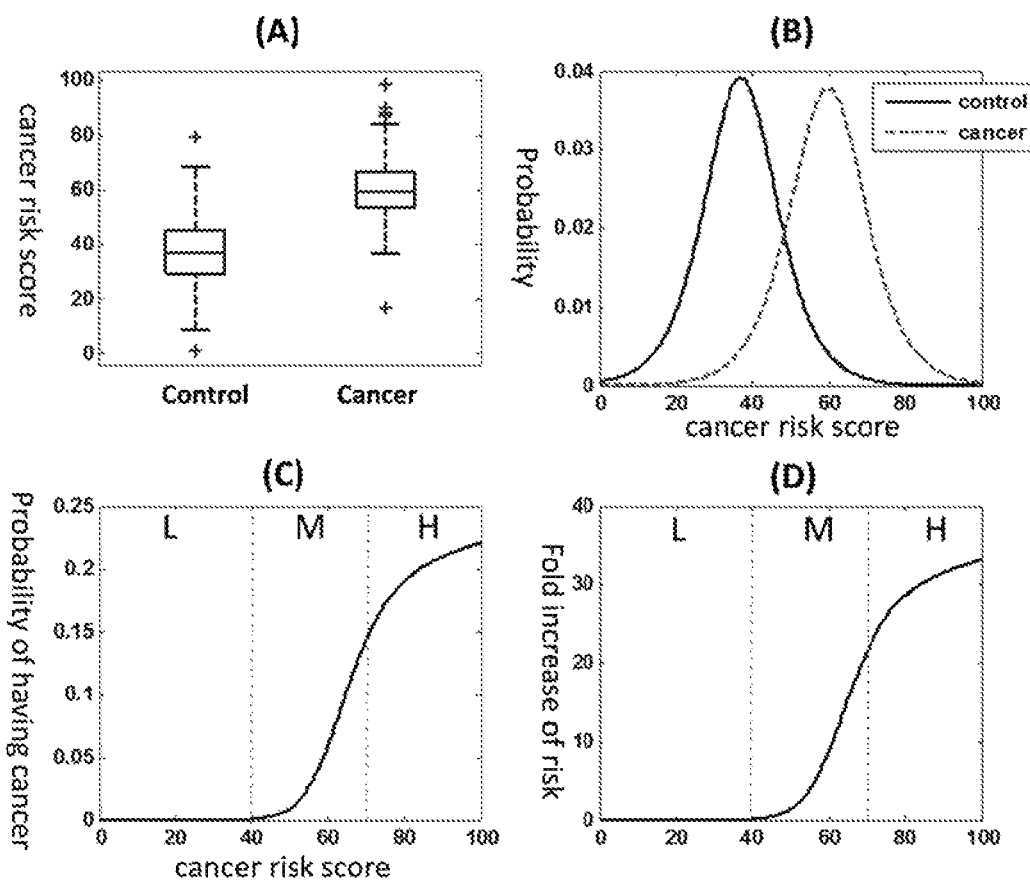
FIG. 15 shows (A) the boxplot representation of cancer risk scores for the control and gastric cancer subjects in this study; (B) the probability distributions of the cancer risk score fitted with logistic distribution for the control and gastric cancer subjects in this study, (C) the probability of an unknown subject (belonging to the high risk population) having gastric cancer depends on the value of cancer risk score (the prevalence of gastric cancer in high risk population was 0.0067 based on the data from National University Hospital); (D) fold increase of the probability (risk) of an unknown subject having gastric cancer at various cancer risk score levels compared to the prevalence of gastric cancer in high risk population. The dashed lines define the threshold scores that separate the subjects into high cancer risk (H), medium cancer risk (M) or low cancer risk (L) groups.

Table 21 lists 12 miRNAs (with their $K_i$ coefficient values) frequently selected in the multivariant biomarker panel identification process with prevalence >20% which are combined to calculate the cancer risk score (Formula 1) in FIG. 15.

DETAILED DESCRIPTION OF THE PRESENT INVENTION

MicroRNAs (miRNAs) are small noncoding RNAs that are known to play a role in gene-expression regulation and aberrant expression is implicated in the pathogenesis of a variety of cancers, including gastric cancer. It is known that microRNA can be used to determine the likelihood of a subject developing a cancer.

Figure 12:
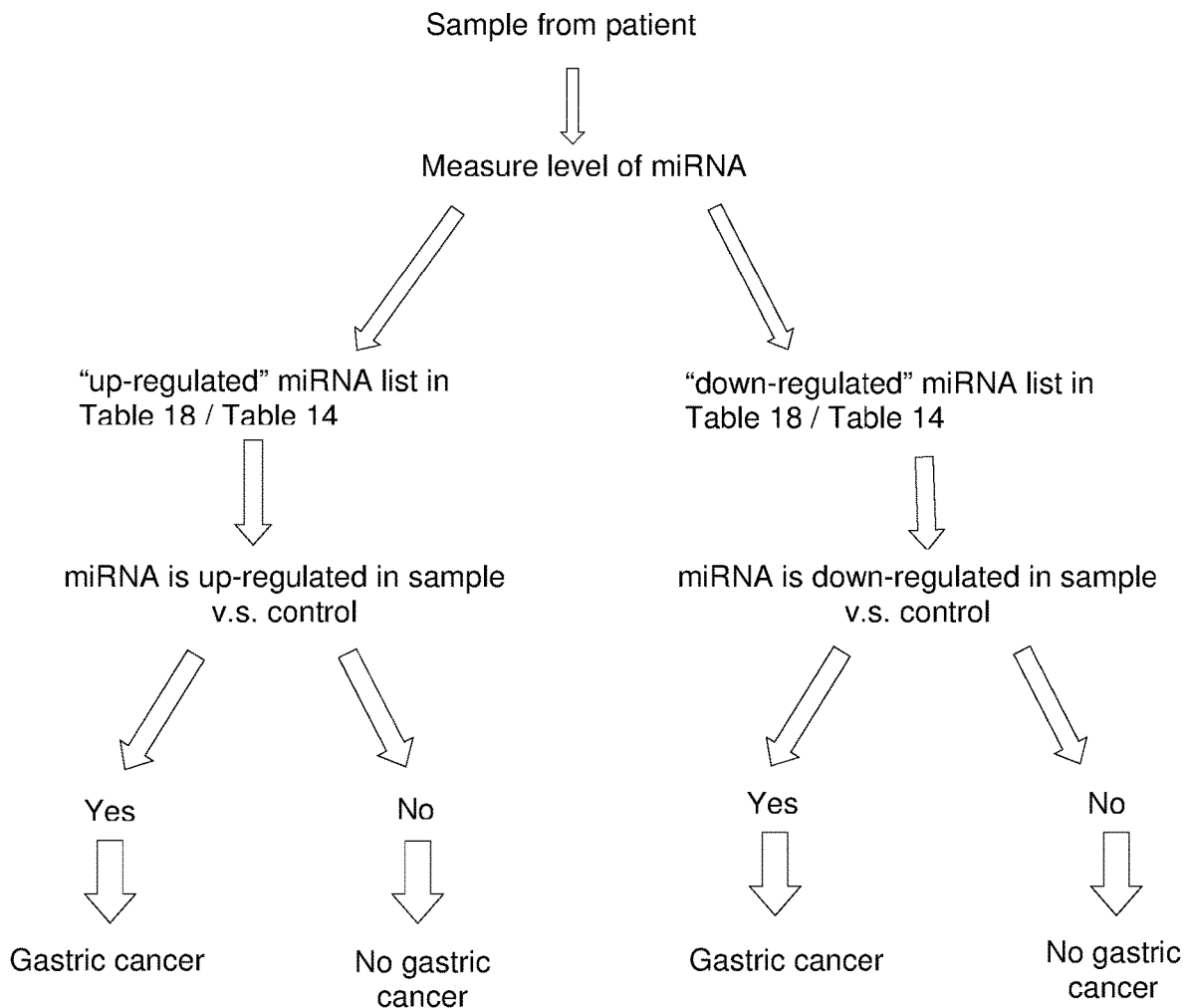
FIG. 12 shows a schematic diagram summarizing the steps of the method as described herein when used to determine the likelihood of a subject having gastric cancer.

Thus, in one aspect, there is provided a method for determining the likelihood of a subject developing or having gastric cancer. In one example, FIG. 12 summarizes the steps of the method for determining the likelihood of a subject developing or having gastric cancer. In one example, the method may also be for detecting or diagnosing gastric cancer in a subject. In one example, the method is an in vitro method. In one example, the method as described herein may comprise measuring or determining the expression level of at least one microRNA (miRNA) having at least 90% sequence identity with an miRNA listed in Table 18 in a non-cellular biofluid sample obtained from the subject, wherein differential expression of miRNA expression, as compared to a control, is indicative of the subject having gastric cancer and wherein the miRNA is either an miRNA listed as "up-regulated" in Table 18 or an miRNA listed as "down-regulated" in Table 18.

Table 18 lists miRNA which may be used to determine the likelihood of a patient developing or having gastric cancer and is as follows:

| Up-regulated | Down-regulated |
|---|---|
| hsa-miR-101-3p | hsa-miR-107 |
| hsa-miR-106b-3p | hsa-miR-122-5p |
| hsa-miR-128 | hsa-miR-126-3p |
| hsa-miR-1280 | hsa-miR-136-5p |
| hsa-miR-140-3p | hsa-miR-139-5p |
| hsa-miR-140-5p | hsa-miR-146a-5p |
| hsa-miR-142-5p | hsa-miR-154-5p |
| hsa-miR-148a-3p | hsa-miR-181a-5p |
| hsa-miR-15b-3p | hsa-miR-193b-3p |
| hsa-miR-183-5p | hsa-miR-23c |
| hsa-miR-186-5p | hsa-miR-26a-5p |
| hsa-miR-18b-5p | hsa-miR-30a-5p |
| hsa-miR-197-3p | hsa-miR-30b-5p |
| hsa-miR-19a-3p | hsa-miR-337-5p |
| hsa-miR-19b-3p | hsa-miR-339-5p |
| hsa-miR-20b-5p | hsa-miR-382-5p |
| hsa-miR-21-3p | hsa-miR-409-3p |
| hsa-miR-23a-5p | hsa-miR-411-5p |
| hsa-miR-25-3p | hsa-miR-485-3p |
| hsa-miR-27a-5p | hsa-miR-487b |
| hsa-miR-29a-3p | hsa-miR-495 |
| hsa-miR-29b-2-5p | hsa-miR-885-5p |
| hsa-miR-29b-3p | hsa-miR-99a-5p |
| hsa-miR-29c-3p | hsa-miR-103a-3p |
| hsa-miR-29c-5p | hsa-miR-362-5p |
| hsa-miR-338-5p | hsa-miR-671-3p |
| hsa-miR-424-5p | hsa-miR-454-3p |
| hsa-miR-425-3p | hsa-miR-328 |
| hsa-miR-4306 | hsa-miR-320a |
| hsa-miR-450a-5p | hsa-miR-99b-5p |
| hsa-miR-486-5p | hsa-miR-126-5p |
| hsa-miR-500a-3p | hsa-miR-27a-3p |
| hsa-miR-501-5p | hsa-miR-30d-5p |
| hsa-miR-532-3p | hsa-miR-10a-5p |
| hsa-miR-550a-5p | hsa-miR-10b-5p |
| hsa-miR-579 | hsa-miR-497-5p |
| hsa-miR-589-5p | hsa-miR-134 |
| hsa-miR-590-5p | hsa-miR-150-5p |
| hsa-miR-598 | |
| hsa-miR-616-5p | |
| hsa-miR-627 | |
| hsa-miR-629-3p | |
| hsa-miR-629-5p | |
| hsa-miR-93-3p | |
| hsa-miR-93-5p | |
| hsa-miR-195-5p | |
| hsa-miR-18a-3p | |
| hsa-miR-363-3p | |
| hsa-miR-181a-2-3p | |
| hsa-miR-16-5p | |
| hsa-miR-501-3p | |
| hsa-miR-23a-3p | |
| hsa-miR-339-3p | |
| hsa-miR-15a-5p | |
| hsa-miR-320b | |
| hsa-miR-374b-5p | |
| hsa-miR-650 | |
| hsa-miR-1290 | |
| hsa-miR-22-3p | |

-continued

| Up-regulated | Down-regulated |
|---|---|
| | hsa-miR-320c |
| | hsa-miR-130a-3p |
| | hsa-miR-320e |
| | hsa-miR-378a-3p |
| | hsa-miR-9-5p |
| | hsa-miR-200b-3p |
| | hsa-miR-141-3p |
| | hsa-miR-191-5p |
| | hsa-miR-628-5p |
| | hsa-miR-484 |
| | hsa-miR-425-5p |

As used herein, the term "miRNA" or "microRNA" or "miR" refers to an RNA (or RNA analog) comprising the product of an endogenous, non-coding gene whose precursor RNA transcripts can form small stem-loops from which mature "miRNAs" are cleaved by the endonuclease Dicer. MiRNAs are encoded in genes distinct from the mRNAs whose expression they control. In one example, the term "miRNA" or "microRNA" refers to single-stranded RNA molecules of at least 10 nucleotides and of not more than 35 nucleotides covalently linked together. In one example, the polynucleotides are molecules of 10 to 33 nucleotides or of 15 to 30 nucleotides in length, or of 17 to 27 nucleotides or of 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The sequences of the miRNAs as described herein are provided in Table 4 provided herein, which includes miRNA sequences SEQ ID NO: 1 to SEQ ID NO: 191. As would be appreciated by the skilled person in the art, miRNA is a type of polynucleotide that has sequences comprising letters such as "ATGC". It will be understood that the nucleotides are in 5'→3' order from left to right and that "A" denotes deoxyadenoside, "C" denotes deoxycytidine, "G" denotes doxyguanoside, and "T" denotes deoxythymidine, unless otherwise noted. The letters A, C, G, and T can be used to refer to the bases themselves, to the nucleosides, or to nucleotides comprising the bases, as is standard in the art. This term includes oligonucleotides composed of naturally occurring nucleobases, sugars, and internucleotides (backbone) linkages as well as oligonucleotides having non-naturally-occurring portions which function similarly or with specific improved functions. In naturally occurring polynucleotides, the inter-nucleoside linkage is typically a phosphodiester bond, and the subunits are referred to as "nucleotides". The term "oligonucleotide" may also include fully or partly modified or substituted oligonucleotides, such as in the bases and/or sugars.

As would be appreciated in the art of the present disclosure, in any of the methods as described herein, the miRNAs may not have 100% sequence identity with the sequences of miRNAs as listed in Table 4. Thus, in one example, the measured miRNA may have at least 75%, or at least 80%, or at least 85%, or at least 90%, or at least 95%, or at least 97.5%, or at least 98%, or at least 99%, or at least 99.9% sequence identity to the miRNAs as listed in any one of Table 8, Table 15, Table 16, Table 17, Table 18, Table 19 or Table 20 (with reference to Table 4). In one example, the measured miRNAs may have one, two, three or four nucleotide substitutions. Thus, the miRNAs as used in the methods as described herein may be detected using reagents that may be able to hybridize or bind specifically to the sequences as listed in Table 8, Table 15, Table 16, Table 17, Table 18, Table 19 or Table 20 (with reference to sequences provided in Table 4). As used herein, the terms "hybridizing to" and "hybridization" are interchangeable used with the terms "specific for" and "specifically binding" and refer to the sequence specific non-covalent binding interactions with a complementary nucleic acid, for example, interactions between a target nucleic acid sequence and a target specific nucleic acid primer or probe. In one example, a nucleic acid probe, which hybridizes is one which hybridizes with a selectivity of greater than 70%, greater than 80%, greater than 90% or of 100% (i.e. cross hybridization with one of the miRNAs as described herein may occur at less than 30%, less than 20%, less than 10%). As would be understood to a person skilled in the art, a nucleic acid probe, which "hybridizes" to the miRNA as described herein may be determined taking into account the length and composition. In one example, the nucleic acid probes, which hybridize with the any of the miRNAs as described herein may have one, or two, or three mismatched base pairing. In one example, the term "miRNA" as described herein may include miRNAs, which during production, the 3'-end and/or 5' end of the miRNA may be modified and/or digested. In one example, miRNA that has been modified and/or digested at the 3'-end and/or 5' end during production is picked up by the assay of the present invention. In one example, the miRNA as disclosed herein may include miRNAs which may differ from the sequences as listed in Table 4 by 3, or 4, or 5 nucleotides.

As used herein, the term "cancer" refers to the presence of cells possessing characteristics typical of cancer-causing cells, such as uncontrolled proliferation, immortality, metastatic potential, rapid growth and proliferation rate, and certain characteristic morphological features known in the art. In one example, the "cancer" may be gastric cancer or stomach cancer. In one example, the "cancer" may include pre-malignant as well as malignant cancers. Thus, the term "gastric cancer" covers all stages of gastric cancer as described by the National Cancer Institute of the National Health.

In one example, as would be appreciated by a person skilled in the art, the methods as described herein do not involve the step performed by a doctor/physician. Thus, the results as obtained from the methods as described herein would need to be combined with clinical data and other clinical presentations before a final diagnosis performed by a physician can be provided to the subject. The final diagnosis on whether a subject has gastric cancer is the scope of a physician and is not considered to be part of the present disclosure. Accordingly, as used herein, the term "determining", "detecting" and "diagnosing" refers to the identification of the chances or likelihood of a subject having disease (such as gastric cancer) at any stage of its development, or the determination of predisposition of a subject to develop the disease. In one example, "diagnosis", "determination", "detecting" occurs prior to the manifestation of symptoms. In one example, "diagnosis", "determination", "detecting", allows a clinician/physician (in conjunction with other clinical presentations), confirmation of gastric cancer in a subject suspected of having gastric cancer.

As used herein, the term "differential expression" refers to a difference in the level of expression of one or more miRNAs, as measured by the amount of miRNA, in one sample as compared with the level of expression of the same one or more miRNA in a second sample or with regard to a predetermined reference value or a control. Differential expression can be determined by methods known in the art, such as by array hybridization, next generation sequencing, RT-PCR and other methods as would be understood by a person skilled in the art.

Depending on the purposes of the methods as described herein, the control group used to determine whether a differential expression is observed may be different. However, as a general rule, the control group, in any given method as described herein, may be readily determined by the skilled person in the art. Unless specifically mentioned otherwise, in one example, the control group may be a subject without any gastric cancer related diseases. In one example, the control group may be a healthy subject without any existing diseases. In one example, the control group may be a subject known to have non-gastric cancer related diseases, such as, but is not limited to, gastritis, intestinal metaplasia, intestinal atrophy and the like. In one example, the control may vary on the nature of the sample as well as other factors such as the gender, age, ethnicity of the subjects based on whom the training data set was obtained from. In one example, the control subject may be of an Asian ethnicity or descent, for example a Chinese ethnicity or ethnic Chinese descent.

In one example, differential expression is observed when an miRNA as listed as "up-regulated" in Table 18, when compared to a control, is found to be up-regulated in the sample obtained from a subject suspected to have gastric cancer. Thus, in one example, upregulation of miRNAs as listed as "up-regulated" in Table 18, as compared to the control, may be indicative of the subject having gastric cancer or diagnoses the subject to have gastric cancer.

As used herein, in any of the examples or methods as described herein, the term "up-regulated" refers to an increase in the level of miRNA expression or the detection of more copies of miRNA as compared to a control. In one example, an miRNA may be considered to be "up-regulated" if the level of expression is at least about 1.01 fold change relative to control or more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, an miRNA may be considered to be "up-regulated" if the level of expression is at least about 1.02 fold change to about 2.5 fold change, relative to control. In one example, as exemplified in Table 6, an miRNA may be considered to be "up-regulated" if the level of expression is at least about 1.05 fold change to about 1.53 fold change, relative to control. In one example, the miRNA may be considered to be "up-regulated" if the level of expression may have about 1.10 fold, or about 1.15 fold, or about 1.20 fold, or about 1.25 fold, or about 1.30 fold, or about 1.35 fold, or about 1.40 fold, or about 1.45 fold, or about 1.50 fold change, relative to control. As used herein, the control may be a gastric cancer free subject.

In one example, differential expression is observed when an miRNA as listed as "down-regulated" in Table 18, when compared to a control, is found to be down-regulated in the sample obtained from a subject suspected to have gastric cancer. Thus, in one example, down-regulation of miRNAs as listed as "down-regulated" in Table 18, as compared to the control, may be indicative of the subject having gastric cancer or may diagnose the subject to have gastric cancer.

As used herein, in any of the examples or methods as described herein, the term "down-regulated" refers to a decrease in the level of miRNA expression or the detection of less copies of miRNA as compared to a control. In one example, an miRNA may be considered to be "down-regulated" if the level of expression is shown to have at least about 0.99 fold change relative to control or less more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, an miRNA may be considered to be "down-regulated" if the level of expression is at least about 0.98 fold change to about 0.3 fold change, relative to control. In one example, as exemplified in Table 6, an miRNA may be considered to be "down-regulated" if the level of expression is shown to have at least about 0.5 fold change to about 0.92 fold change, relative to control. In one example, the miRNA expression may be considered to be "down-regulated" if the level of expression may have about 0.95 fold, or about 0.90 fold, or about 0.85 fold, or about 0.80 fold, or about 0.75 fold, or about 0.70 fold, or about 0.65 fold, or about 0.60 fold, or about 0.55 fold change, relative to control. As used herein, the control may be a gastric cancer free subject.

The term "about" is used herein to indicate that a value includes the inherent variation of error as known in the art, which may occur from the use of devices, methods being employed to determine the value, or the variation that exists among the study subjects. Thus, in one example, the term "about", in the context of fold change in expression, as used throughout the present disclosure as described herein, may mean+/−5% of the stated value, or +/−4% of the stated value, or +/−3% of the stated value, or +/−2% of the stated value, or +/−1% of the stated value, or +/−0.5% of the stated value.

In one example, the method as described herein may measures the differential expression of one or more miRNAs as listed in Table 18. Thus, in one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45, or at least 50, or at least 55, or at least 60, or at least 65, or at least 70, or at least 75, or at least 80, or at least 85, or at least 90, or at least 95, or at least 100, or at least 105, or at least 107 or all of the miRNA as listed in Table 18. In one example, the method may measure from one to 108 miRNAs listed in Table 18, or from two to 10, or from 11 to 30, or from 31 to 50, or from 50 to 70, or from 71 to 90, or from 91 to 108 miRNAs as listed in Table 18. In one example, the method may measure differential expression of all miRNAs listed in Table 18.

In one example, the method as described herein may measure the differential expression of at least one miRNA as listed as "up-regulated" in Table 18 and at least one miRNA as listed as "down-regulated in Table 18. In one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45, or at least 50, or at least 55, or at least 60, or at least 65, or 70 of the miRNA as listed as "up-regulated" in Table 18; and at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or 38 of the miRNA as listed as "down-regulated" in Table 18.

In one example, the method as described herein may comprise measuring the expression level of at least one microRNA (miRNA) as listed in Table 14 in a non-cellular biofluid sample obtained from the subject.

Table 14 lists miRNA which may be used to determine the likelihood of a patient developing or having gastric cancer and is as follows:

| Up-regulated | Down-regulated |
| --- | --- |
| hsa-miR-101-3p | hsa-miR-107 |
| hsa-miR-106b-3p | hsa-miR-122-5p |
| hsa-miR-128 | hsa-miR-126-3p |
| hsa-miR-1280 | hsa-miR-136-5p |
| hsa-miR-140-3p | hsa-miR-139-5p |
| hsa-miR-140-5p | hsa-miR-146a-5p |
| hsa-miR-142-5p | hsa-miR-154-5p |
| hsa-miR-148a-3p | hsa-miR-181a-5p |
| hsa-miR-15b-3p | hsa-miR-193b-3p |
| hsa-miR-183-5p | hsa-miR-23c |
| hsa-miR-186-5p | hsa-miR-26a-5p |
| hsa-miR-18b-5p | hsa-miR-30a-5p |
| hsa-miR-197-3p | hsa-miR-30b-5p |
| hsa-miR-19a-3p | hsa-miR-337-5p |
| hsa-miR-19b-3p | hsa-miR-339-5p |
| hsa-miR-20b-5p | hsa-miR-382-5p |
| hsa-miR-21-3p | hsa-miR-409-3p |
| hsa-miR-23a-5p | hsa-miR-411-5p |
| hsa-miR-25-3p | hsa-miR-485-3p |
| hsa-miR-27a-5p | hsa-miR-487b |
| hsa-miR-29a-3p | hsa-miR-495 |
| hsa-miR-29b-2-5p | hsa-miR-885-5p |
| hsa-miR-29b-3p | hsa-miR-99a-5p |
| hsa-miR-29c-3p | hsa-miR-99b-5p |
| hsa-miR-29c-5p | |
| hsa-miR-338-5p | |
| hsa-miR-424-5p | |
| hsa-miR-425-3p | |
| hsa-miR-4306 | |
| hsa-miR-450a-5p | |
| hsa-miR-486-5p | |
| hsa-miR-500a-3p | |
| hsa-miR-501-5p | |
| hsa-miR-532-3p | |
| hsa-miR-550a-5p | |
| hsa-miR-579 | |
| hsa-miR-589-5p | |
| hsa-miR-590-5p | |
| hsa-miR-598 | |
| hsa-miR-616-5p | |
| hsa-miR-627 | |
| hsa-miR-629-3p | |
| hsa-miR-629-5p | |
| hsa-miR-93-3p | |
| hsa-miR-93-5p | |

As known in the art, when a proliferative disease progress (with or without treatment), the clinical presentation of the disease will vary between stages of the progression. Thus, to assist the skilled person in determining how a gastric/stomach cancer has progressed, the National Cancer Institute at the National Institute of Health has published a generalized clinical presentation of stages observed in gastric/stomach cancer. The stages of a gastric cancer include, but are not strictly limited within its definition to, the following stages described as follows:

Stage I: In stage I, cancer has formed in the inside lining of the mucosa (innermost layer) of the stomach wall. Stage I is divided into stage IA and stage IB, depending on where the cancer has spread.

Stage IA: Cancer may have spread into the submucosa (layer of tissue next to the mucosa) of the stomach wall.

Stage IB: Cancer may have spread into the submucosa (layer of tissue next to the mucosa) of the stomach wall and is found in 1 or 2 lymph nodes near the tumor; or has spread to the muscle layer of the stomach wall.

Stage II: Stage II gastric cancer is divided into stage IIA and stage IIB, depending on where the cancer has spread.

Stage IIA: Cancer has spread to the subserosa (layer of tissue next to the serosa) of the stomach wall; or has spread to the muscle layer of the stomach wall and is found in 1 or 2 lymph nodes near the tumor; or may have spread to the submucosa (layer of tissue next to the mucosa) of the stomach wall and is found in 3 to 6 lymph nodes near the tumor.

Stage IIB: Cancer has spread to the serosa (outermost layer) of the stomach wall; or has spread to the subserosa (layer of tissue next to the serosa) of the stomach wall and is found in 1 or 2 lymph nodes near the tumor; or has spread to the muscle layer of the stomach wall and is found in 3 to 6 lymph nodes near the tumor; or may have spread to the submucosa (layer of tissue next to the mucosa) of the stomach wall and is found in 7 or more lymph nodes near the tumor.

Stage III: Stage III gastric cancer is divided into stage IIIA, stage IIIB, and stage IIIC, depending on where the cancer has spread.

Stage IIIA: Cancer has spread to the serosa (outermost) layer of the stomach wall and is found in 1 or 2 lymph nodes near the tumor; or has spread to the subserosa (layer of tissue next to the serosa) of the stomach wall and is found in 3 to 6 lymph nodes near the tumor; or has spread to the muscle layer of the stomach wall and is found in 7 or more lymph nodes near the tumor.

Stage IIIB: Cancer has spread to nearby organs such as the spleen, transverse colon, liver, diaphragm, pancreas, kidney, adrenal gland, or small intestine, and may be found in 1 or 2 lymph nodes near the tumor; or has spread to the serosa (outermost layer) of the stomach wall and is found in 3 to 6 lymph nodes near the tumor; or the subserosa (layer of tissue next to the serosa) of the stomach wall and is found in 7 or more lymph nodes near the tumor.

Stage IIIC: Cancer has spread to nearby organs such as the spleen, transverse colon, liver, diaphragm, pancreas, kidney, adrenal gland, or small intestine, and may be found in 3 or more lymph nodes near the tumor; or has spread to the serosa (outermost layer) of the stomach wall and is found in 7 or more lymph nodes near the tumor.

Stage IV: In stage IV, cancer has spread to distant parts of the body.

Figure 13:
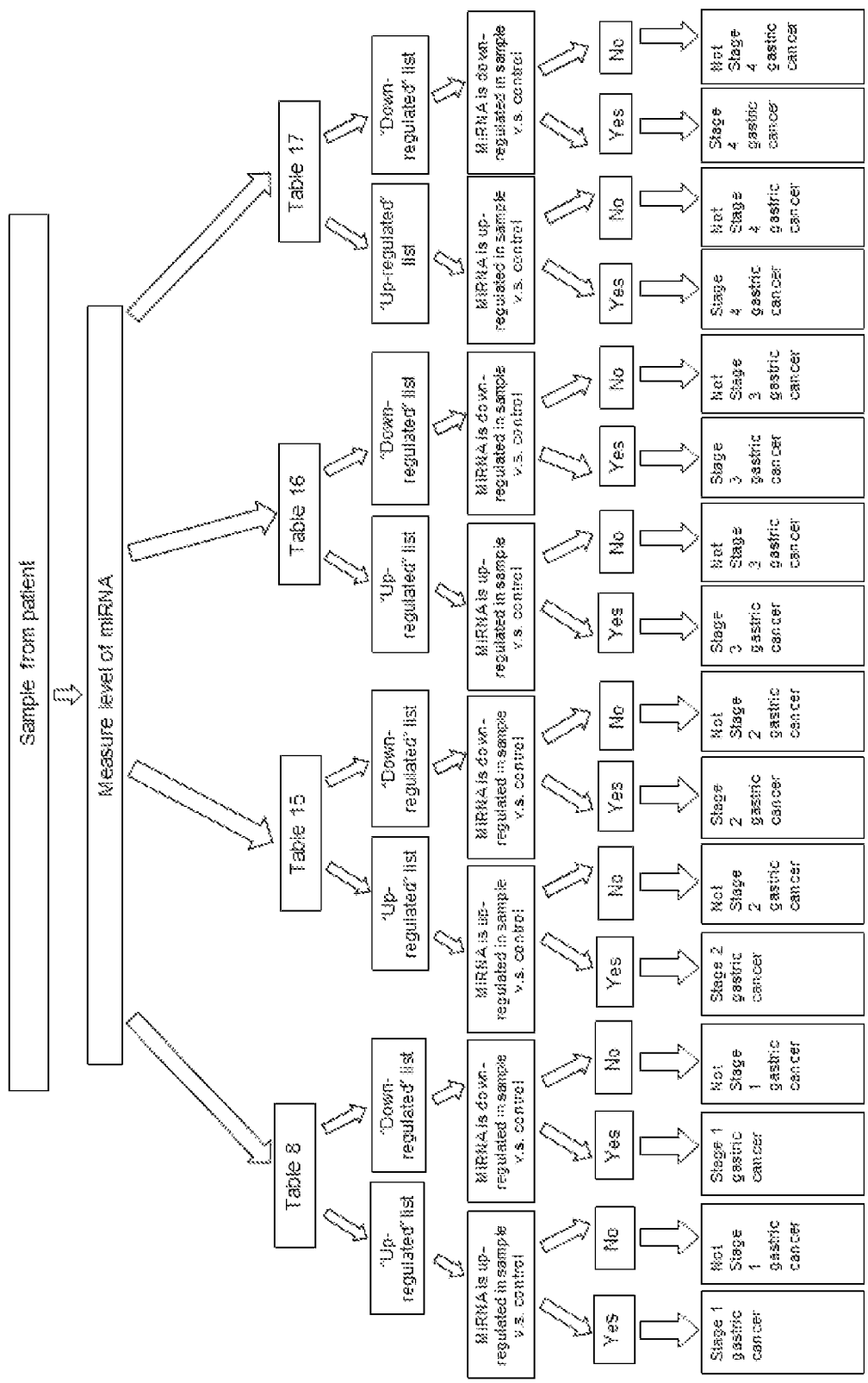
FIG. 13 shows a schematic diagram summarizing the steps of the method as described herein when used to determine the likelihood of a subject having one of the stages of gastric cancer.

As would be appreciated by a skilled person in the art, the determination on whether a subject has a particular stage would be useful in providing the clinician a clear guideline on how to best approach any treatment or palliative care. Thus, in one aspect, the present disclosure provides a method of detecting or diagnosing gastric cancer stage in a subject. In one example, the method determines the likelihood of a subject having a stage of gastric cancer. In this aspect, the method comprising measuring the expression level of at least one microRNA (miRNA) having at least 90% sequence identity with an miRNA as listed in at least one of the tables selected from the group consisting of Table 8; Table 9 or Table 15; Table 10 or Table 16; and Table 11 or Table 17, in a non-cellular biofluid sample obtained from the subject, wherein a differential expression of miRNA expression in the sample obtained from the subject, as compared to a control, may be indicative of the likelihood of a subject having any one of stage 1, stage 2, stage 3 or stage 4 gastric cancer, or may diagnose the subject to have any one of stage 1, stage 2, stage 3 or stage 4 gastric cancer. As used herein, the control may be a gastric cancer free subject. In one example, FIG. 13 summarizes the steps of the method for determining the likelihood of a subject developing or having one of the stages of gastric cancer.

In one example, differential expression is observed when an miRNA as listed as "up-regulated" in Table 8, as compared to the control, may be indicative of the subject to have stage 1 gastric cancer or may diagnose the subject to have stage 1 gastric cancer, and wherein the miRNA may include at least one of the miRNA as listed as "up-regulated" in Table 8. Table 8 is detailed further in the Experimental section. In one example, an miRNA may be considered to be "up-regulated" if the level of expression is at least about 1.01 fold change to about 2.5 fold change, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA may be considered to be "up-regulated" if the level of expression may have about 1.10 fold, or about 1.15 fold, or about 1.20 fold, or about 1.25 fold, or about 1.30 fold, or about 1.35 fold, or about 1.40 fold, or about 1.45 fold, or about 1.50 fold change, relative to control. In one example, as exemplified in Table 8, an miRNA may be considered to be "up-regulated" if the level of expression is at least about 1.11 fold change to about 1.57 fold change, relative to control.

In one example, the method as described herein may measures the differential expression of one or more miRNAs as listed as "up-regulated" in Table 8. Thus, in one example, the method may measure the differential expression of at least two, or at least three, or at least four, or at least five, or at least six, or at least seven, or eight miRNAs as listed as "up-regulated" in Table 8.

In one example, differential expression is observed when an miRNA as listed as "down-regulated" in Table 8, as compared to the control, may be indicative of the subject to have stage 1 gastric cancer or may diagnose the subject to have stage 1 gastric cancer. In one example, the miRNA may include at least one of the miRNA as listed as "down-regulated" in Table 8. In one example, an miRNA may be considered to be "down-regulated" if the level of expression has at least about 0.9 fold change or less, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA expression may be considered to be "down-regulated" if the level of expression may have about 0.95 fold, or about 0.90 fold, or about 0.85 fold, or about 0.80 fold, or about 0.75 fold, or about 0.70 fold, or about 0.65 fold, or about 0.60 fold, or about 0.55 fold change, relative to control. In one example, as exemplified in Table 8, an miRNA may be considered to be "down-regulated" if the level of expression has at least about 0.68 fold change to about 0.84 fold change, relative to control.

In one example, the method as described herein may measure the differential expression of one or more miRNAs as listed as "down-regulated" in Table 8. Thus, in one example, the method may measure the differential expression of at least two, or at least three, or at least four, or at least five, or at least six, or at least seven, or at least eight, or at least nine, or at least ten, or at least eleven or twelve miRNAs as listed as "down-regulated" in Table 8.

In one example, the method as described herein may measure the differential expression of at least one miRNA as listed as "up-regulated" in Table 8 and at least one miRNA as listed as "down-regulated in Table 8. In one example, the method may measure the differential expression of at least two, or at least three, or at least four, or at least five, or at least six, or at least seven, or 8 of the miRNA as listed as "up-regulated" in Table 8; and at least two, or at least three, or at least four, or at least five, or at least six, or at least seven, or at least eight, or at least nine, or at least 10, or at least 11, or 12 of the miRNA as listed as "down-regulated" in Table 8.

In one example, differential expression is observed when an miRNA as listed as "up-regulated" in Table 9 or Table 15, as compared to the control, may be indicative of the subject to have stage 2 gastric cancer or may diagnose the subject to have stage 2 gastric cancer. Table 9 is detailed further in the Experimental section. In one example, the miRNA may include at least one of the miRNA as listed as "up-regulated" in Table 15.

Table 15 lists miRNA which may be used to determine the likelihood of a patient developing (or having) or having stage 2 gastric cancer and is as follows:

| Up-regulated | Down-regulated |
|---|---|
| hsa-miR-27a-5p | hsa-miR-126-3p |
| hsa-miR-183-5p | hsa-miR-107 |
| hsa-miR-629-5p | hsa-miR-320a |
| hsa-miR-424-5p | hsa-miR-339-5p |
| hsa-miR-1280 | hsa-miR-337-5p |
| hsa-miR-18b-5p | hsa-miR-99b-5p |
| hsa-miR-195-5p | hsa-miR-193b-3p |
| hsa-miR-18a-3p | hsa-miR-885-5p |
| hsa-miR-550a-5p | |
| hsa-miR-197-3p | |
| hsa-miR-363-3p | |
| hsa-miR-450a-5p | |
| hsa-miR-20b-5p | |
| hsa-miR-15b-3p | |
| hsa-miR-142-5p | |
| hsa-miR-93-5p | |
| hsa-miR-501-5p | |
| hsa-miR-4306 | |
| hsa-miR-181a-2-3p | |
| hsa-miR-16-5p | |
| hsa-miR-128 | |
| hsa-miR-500a-3p | |
| hsa-miR-501-3p | |
| hsa-miR-19a-3p | |
| hsa-miR-629-3p | |
| hsa-miR-25-3p | |
| hsa-miR-140-5p | |
| hsa-miR-29a-3p | |
| hsa-miR-23a-5p | |
| hsa-miR-148a-3p | |
| hsa-miR-598 | |
| hsa-miR-186-5p | |
| hsa-miR-93-3p | |
| hsa-miR-23a-3p | |
| hsa-miR-339-3p | |
| hsa-miR-15a-5p | |
| hsa-miR-29b-3p | |
| hsa-miR-140-3p | |
| hsa-miR-29c-5p | |

| Up-regulated | Down-regulated |
| --- | --- |
| hsa-miR-320b | |
| hsa-miR-15b-5p | |
| hsa-miR-221-3p | |
| hsa-miR-29b-2-5p | |
| hsa-miR-532-3p | |
| hsa-miR-374b-5p | |
| hsa-miR-29c-3p | |
| hsa-miR-589-5p | |
| hsa-miR-106b-3p | |

In one example, an miRNA may be considered to be "up-regulated" if the level of expression is at least about 1.01 fold change to about 2.5 fold change, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA may be considered to be "up-regulated" if the level of expression may have about 1.10 fold, or about 1.15 fold, or about 1.20 fold, or about 1.25 fold, or about 1.30 fold, or about 1.35 fold, or about 1.40 fold, or about 1.45 fold, or about 1.50 fold change, relative to control. In one example, as exemplified in Table 9, an miRNA may be considered to be "up-regulated" if the level of expression is at least about 1.13 fold change to about 2.13 fold change, relative to control.

In one example, the method as described herein may measures the differential expression of one or more miRNAs as listed as "up-regulated" in Table 9 or Table 15. Thus, in one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45, or at least 50, or 54 miRNAs as listed as "up-regulated" in Table 9 or Table 15.

In one example, differential expression is observed when an miRNA as listed as "down-regulated" in Table 9 or Table 15, as compared to the control, may be indicative of the subject to have stage 2 gastric cancer or may diagnose the subject to have stage 2 gastric cancer. In one example, the miRNA may include at least one of the miRNA as listed as "down-regulated" in Table 15. In one example, an miRNA may be considered to be "down-regulated" if the level of expression has at least about 0.9 fold change or less, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA expression may be considered to be "down-regulated" if the level of expression may have about 0.95 fold, or about 0.90 fold, or about 0.85 fold, or about 0.80 fold, or about 0.75 fold, or about 0.70 fold, or about 0.65 fold, or about 0.60 fold, or about 0.55 fold change, relative to control. In one example, as exemplified in Table 9, an miRNA may be considered to be "down-regulated" if the level of expression has at least about 0.56 fold change to about 0.87 fold change, relative to control.

In one example, the method as described herein may measures the differential expression of one or more miRNAs as listed as "down-regulated" in Table 9 or 15. Thus, in one example, the method may measure the differential expression of at least two, or at least three, or at least four, or at least five, or at least six, or at least seven, or eight miRNAs as listed as "down-regulated" in Table 9 or 15.

In one example, the method as described herein may measure the differential expression of at least one miRNA as listed as "up-regulated" in Table 9 or 15 and at least one miRNA as listed as "down-regulated in Table 9 or 15. In one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45, or at least 50, or 54 miRNAs as listed as "up-regulated" in Table 9 or Table 15; and at least two, or at least three, or at least four, or at least five, or at least six, or at least seven, or eight of the miRNA as listed as "down-regulated" in Table 9 or Table 15.

In one example, when the method as described herein that may provide a diagnosis or an indication on whether a subject may have stage 2 gastric cancer uses Table 15, the method may further comprise comparing the expression level of any one or more of miRNAs including, but not limited to, of miR-20a-5p, miR-223-3p, miR-17-5p, miR-106b-5p, miR-423-5p, and miR-21-5p.

In one example, differential expression is observed when an miRNA as listed as "up-regulated" in Table 10 or Table 16, as compared to the control, may be indicative of the subject to have stage 3 gastric cancer or may diagnose the subject to have stage 3 gastric cancer. Table 10 is detailed further in the Experimental section. In one example, the miRNA may include at least one of the miRNA as listed as "up-regulated" in Table 16.

Table 16 lists miRNA which may be used to determine the likelihood of a patient developing (or having) or having stage 3 gastric cancer and is as follows:

| Up-regulated | Down-regulated |
| --- | --- |
| hsa-miR-629-5p | hsa-miR-126-5p |
| hsa-miR-650 | hsa-miR-126-3p |
| hsa-miR-1280 | hsa-miR-27a-3p |
| hsa-miR-27a-5p | hsa-miR-99b-5p |
| hsa-miR-18b-5p | hsa-miR-107 |
| hsa-miR-424-5p | hsa-miR-30a-5p |
| hsa-miR-500a-3p | |
| hsa-miR-629-3p | |
| hsa-miR-550a-5p | |
| hsa-miR-4306 | |
| hsa-miR-197-3p | |
| hsa-miR-616-5p | |
| hsa-miR-128 | |
| hsa-miR-450a-5p | |
| hsa-miR-148a-3p | |
| hsa-miR-598 | |
| hsa-miR-15b-3p | |
| hsa-miR-1290 | |
| hsa-miR-93-3p | |
| hsa-miR-22-3p | |
| hsa-miR-23a-5p | |
| hsa-miR-320c | |
| hsa-miR-130a-3p | |
| hsa-miR-320b | |

-continued

| Up-regulated | Down-regulated |
|---|---|
| hsa-miR-320e | |
| hsa-miR-19a-3p | |
| hsa-miR-378a-3p | |
| hsa-miR-9-5p | |
| hsa-miR-29b-2-5p | |
| hsa-miR-532-3p | |
| hsa-miR-590-5p | |
| hsa-miR-589-5p | |
| hsa-miR-140-5p | |
| hsa-miR-29c-5p | |

In one example, an miRNA may be considered to be "up-regulated" if the level of expression is at least about 1.01 fold change to about 2.5 fold change, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA may be considered to be "up-regulated" if the level of expression may have about 1.10 fold, or about 1.15 fold, or about 1.20 fold, or about 1.25 fold, or about 1.30 fold, or about 1.35 fold, or about 1.40 fold, or about 1.45 fold, or about 1.50 fold change, relative to control. In one example, as exemplified in Table 10, an miRNA may be considered to be "up-regulated" if the level of expression is at least about 1.20 fold change to about 1.93 fold change, relative to control.

In one example, the method as described herein may measures the differential expression of one or more miRNAs as listed as "up-regulated" in Table 10 or Table 16. Thus, in one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or 37 miRNAs as listed as "up-regulated" in Table 10 or Table 16.

In one example, differential expression is observed when an miRNA as listed as "down-regulated" in Table 10 or Table 16, as compared to the control, may be indicative of the subject to have stage 3 gastric cancer or may diagnose the subject to have stage 3 gastric cancer. In one example, the miRNA may include at least one of the miRNA as listed as "down-regulated" in Table 16. In one example, an miRNA may be considered to be "down-regulated" if the level of expression has at least about 0.9 fold change or less, relative to control. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA expression may be considered to be "down-regulated" if the level of expression may have about 0.95 fold, or about 0.90 fold, or about 0.85 fold, or about 0.80 fold, or about 0.75 fold, or about 0.70 fold, or about 0.65 fold, or about 0.60 fold, or about 0.55 fold change, relative to control. In one example, as exemplified in Table 10, an miRNA may be considered to be "down-regulated" if the level of expression has at least about 0.72 fold change to about 0.88 fold change, relative to control.

In one example, the method as described herein may measures the differential expression of one or more miRNAs as listed as "down-regulated" in Table 10 or 16. Thus, in one example, the method may measure the differential expression of at least two, or at least three, or at least four, or at least five, or six miRNAs as listed as "down-regulated" in Table 10 or 16.

In one example, the method as described herein may measure the differential expression of at least one miRNA as listed as "up-regulated" in Table 10 or 16 and at least one miRNA as listed as "down-regulated in Table 10 or 16. In one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or 37 miRNAs as listed as "up-regulated" in Table 10 or Table 16; and at least two, or at least three, or at least four, or at least five, or six of the miRNA as listed as "down-regulated" in Table 10 or Table 16.

In one example, the method as described herein that may provide a diagnosis or an indication on whether a subject may have stage 3 gastric cancer uses Table 16, the method may further comprise comparing the expression level of any one or more of miRNAs including, but not limited to, miR-21-5pm, miR-223-3p and miR-423-5p.

In one example, differential expression is observed when an miRNA as listed as "up-regulated" in Table 11 or Table 17, as compared to the control, may be indicative of the subject to have stage 4 gastric cancer or may diagnose the subject to have stage 4 gastric cancer. Table 10 is detailed further in the Experimental section. In one example, the miRNA may include at least one of the miRNA as listed as "up-regulated" in Table 17.

Table 17 lists miRNA which may be used to determine the likelihood of a patient developing (or having) stage 4 gastric cancer and is as follows:

| Up-regulated | Down-regulated |
|---|---|
| hsa-miR-27a-5p | hsa-miR-181a-5p |
| hsa-miR-338-5p | hsa-miR-30d-5p |
| hsa-miR-450a-5p | hsa-miR-30b-5p |
| hsa-miR-183-5p | hsa-miR-126-3p |
| hsa-miR-579 | hsa-miR-146a-5p |
| hsa-miR-616-5p | hsa-miR-107 |
| hsa-miR-424-5p | hsa-miR-99b-5p |
| hsa-miR-200b-3p | hsa-miR-10a-5p |
| hsa-miR-148a-3p | hsa-miR-139-5p |
| hsa-miR-142-5p | hsa-miR-10b-5p |
| hsa-miR-629-3p | hsa-miR-23c |
| hsa-miR-4306 | hsa-miR-497-5p |
| hsa-miR-15b-3p | hsa-miR-154-5p |
| hsa-miR-627 | hsa-miR-26a-5p |
| hsa-miR-20b-5p | hsa-miR-339-5p |
| hsa-miR-197-3p | hsa-miR-382-5p |
| hsa-miR-101-3p | hsa-miR-134 |
| hsa-miR-598 | hsa-miR-409-3p |
| hsa-miR-23a-5p | hsa-miR-487b |
| hsa-miR-141-3p | hsa-miR-136-5p |
| hsa-miR-19a-3p | hsa-miR-150-5p |
| hsa-miR-550a-5p | hsa-miR-193b-3p |
| hsa-miR-140-5p | hsa-miR-30a-5p |
| hsa-miR-29c-3p | hsa-miR-99a-5p |
| hsa-miR-18b-5p | hsa-miR-337-5p |
| hsa-miR-590-5p | hsa-miR-495 |

-continued

| Up-regulated | Down-regulated |
|---|---|
| hsa-miR-1280 | hsa-miR-885-5p |
| hsa-miR-191-5p | hsa-miR-122-5p |
| hsa-miR-589-5p | |
| hsa-miR-140-3p | |
| hsa-miR-93-5p | |
| hsa-miR-29b-3p | |
| hsa-miR-628-5p | |
| hsa-miR-93-3p | |
| hsa-miR-106b-3p | |
| hsa-miR-484 | |
| hsa-miR-29a-3p | |
| hsa-miR-29b-2-5p | |
| hsa-miR-29c-5p | |
| hsa-miR-425-5p | |
| hsa-miR-425-3p | |

In one example, an miRNA may be considered to be "up-regulated" if the level of expression is at least about 1.01 fold change to about 2.5 fold change, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA may be considered to be "up-regulated" if the level of expression may have about 1.10 fold, or about 1.15 fold, or about 1.20 fold, or about 1.25 fold, or about 1.30 fold, or about 1.35 fold, or about 1.40 fold, or about 1.45 fold, or about 1.50 fold change, relative to control. In one example, as exemplified in Table 11, an miRNA may be considered to be "up-regulated" if the level of expression is at least about 1.12 fold change to about 1.86 fold change, relative to control.

In one example, the method as described herein may measures the differential expression of one or more miRNAs as listed as "up-regulated" in Table 11 or Table 17. Thus, in one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45 or 46 miRNAs as listed as "up-regulated" in Table 11 or Table 17.

In one example, differential expression is observed when an miRNA as listed as "down-regulated" in Table 11 or Table 17, as compared to the control, may be indicative of the subject to have stage 4 gastric cancer or may diagnose the subject to have stage 4 gastric cancer. In one example, the miRNA may include at least one of the miRNA as listed as "down-regulated" in Table 17. In one example, an miRNA may be considered to be "down-regulated" if the level of expression has at least about 0.9 fold change or less, relative to control more. In one example, the p-values in a statistical test for the change may be lower than 0.05. In one example, the p-values may be calculated using a statistical test known in the art such as a t-test (p-value<0.01). In another example, the statistical test is a t-test (p-value<0.01) that is corrected for false discovery rate (FDR) estimation using Bonferroni-type multiple comparison procedures as known in the art. This was exemplarily used in the examples below. In one example, the miRNA expression may be considered to be "down-regulated" if the level of expression may have about 0.95 fold, or about 0.90 fold, or about 0.85 fold, or about 0.80 fold, or about 0.75 fold, or about 0.70 fold, or about 0.65 fold, or about 0.60 fold, or about 0.55 fold change, relative to control. In one example, as exemplified in Table 11, an miRNA may be considered to be "down-regulated" if the level of expression has at least about 0.48 fold change to about 0.90 fold change, relative to control.

In one example, the method as described herein may measures the differential expression of one or more miRNAs as listed as "down-regulated" in Table 11 or 17. Thus, in one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or 28 miRNAs as listed as "down-regulated" in Table 11 or 17.

In one example, the method as described herein may measure the differential expression of at least one miRNA as listed as "up-regulated" in Table 11 or 17 and at least one miRNA as listed as "down-regulated in Table 11 or 17. In one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or at least 40, or at least 45 or 46 miRNAs as listed as "up-regulated" in Table 11 or Table 17; and at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or 28 of the miRNA as listed as "down-regulated" in Table 11 or Table 17.

In one example, the method as described herein that may provide a diagnosis or an indication on whether a subject may have stage 4 gastric cancer uses Table 17, the method may further comprise comparing the expression level of any one or more of miRNAs including, but not limited to, miR-21-5pm, miR-223-3pm, miR-20a-5pm, miR-106b-5p, and miR-17-5p.

Figure 14:
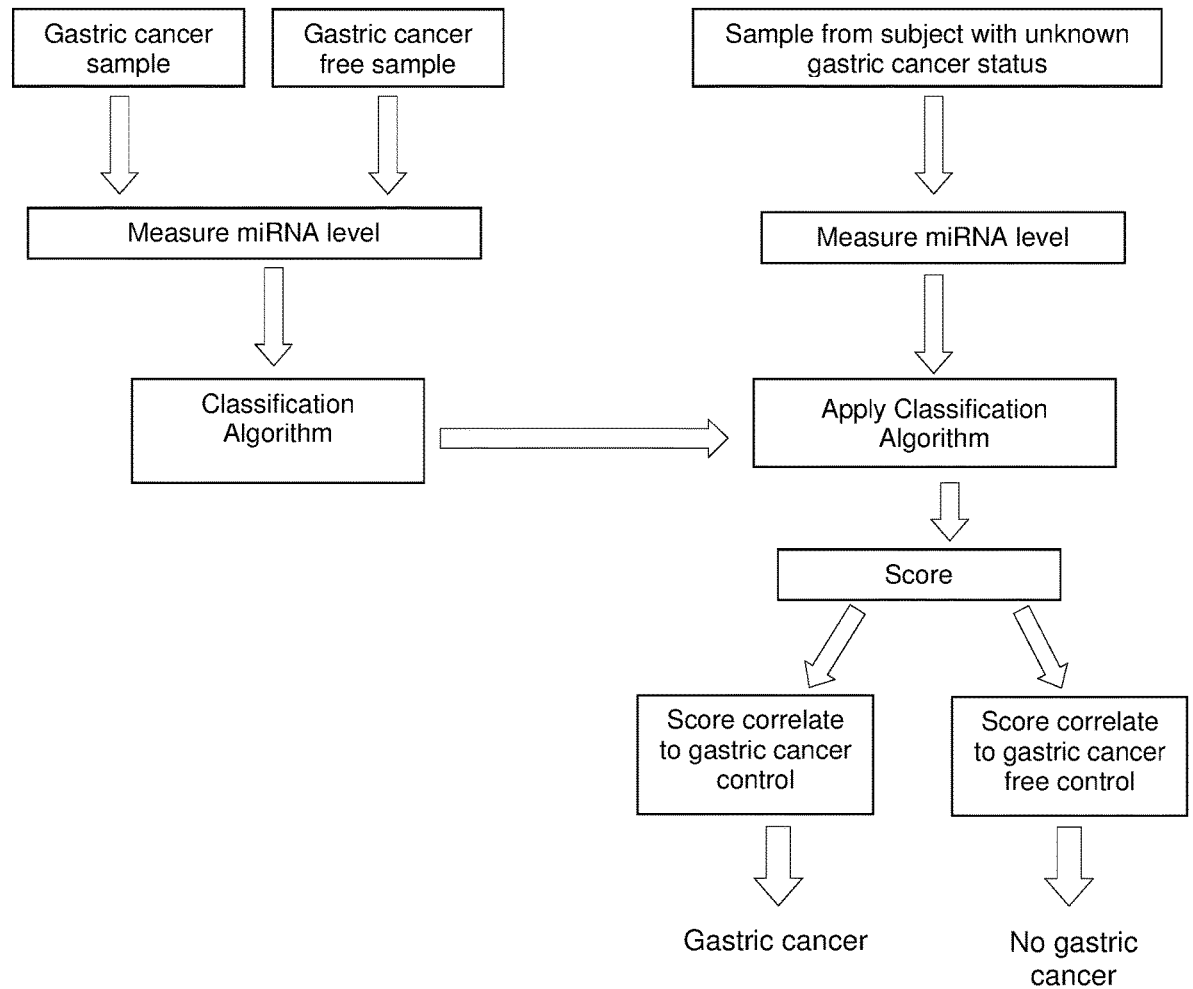
FIG. 14 shows a schematic diagram summarizing the steps of the multivariant method as described herein in determining the likelihood of a subject having gastric cancer.

In yet another aspect, there is provided a method of detecting or diagnosing gastric cancer in a subject or determining the likelihood of a subject having gastric cancer or, comprising the steps of: (a) measuring the expression level of at least one miRNAs having at least 90% sequence identity with an miRNA as listed in Table 12 or Table 19 in a non-cellular biofluid sample; (b) generating a score based on the expression level of the miRNAs measured in step (a); and (c) using the score to predict the likelihood of the subject having gastric cancer, wherein the score is calculated by a classification algorithm that compares the expression level of the subject with that of a positive control (sample from gastric cancer subject) or a negative control (sample from gastric cancer free subject), and the score identifies the likelihood of the subject to either: (i) have gastric cancer, which score would fall within the score of the positive control, or (ii) have no gastric cancer (i.e. gastric cancer free), which score would fall within the score of the negative control. In one example, the miRNA may include at least one of the miRNA as listed as in Table 19. In one example, this method of detecting or diagnosing gastric cancer in a subject or determining the likelihood of a subject having gastric cancer may be referred to as a multivariant method. In one example, the multivariant method may use miRNAs that have been determined by a clinical data to be representative of a sub-population or group. In one example, the multivariant biomarker panel may comprise biomarkers as listed in Table 12, which comprises both miRNAs found to be associated with gastric cancer and miRNAs found to be not associated with gastric cancer. In one example, the miRNAs that may be used in the multivariant method that are associated with gastric cancer may be comprised in Table 19. Table 12 is detailed further in the Experimental section. In one example, FIG. 14 summarizes the steps of the multivariant method for determining the likelihood of a subject developing (or having) gastric cancer.

Table 19 lists miRNAs frequently selected for use in multivariant biomarker panel where the expression levels of the miRNAs were altered in the gastric cancer subjects and is as follows:

| miRNA altered in gastric cancer |
| --- |
| hsa-miR-103a-3p |
| hsa-miR-181a-5p |
| hsa-miR-142-5p |
| hsa-miR-27a-5p |
| hsa-miR-26a-5p |
| hsa-miR-616-5p |
| hsa-miR-30a-5p |
| hsa-miR-484 |
| hsa-miR-4306 |
| hsa-miR-590-5p |
| hsa-miR-362-5p |
| hsa-miR-106b-3p |
| hsa-miR-497-5p |
| hsa-miR-18b-5p |
| hsa-miR-122-5p |
| hsa-miR-200b-3p |
| hsa-miR-197-3p |
| hsa-miR-486-5p |
| hsa-miR-99a-5p |
| hsa-miR-885-5p |
| hsa-miR-598 |
| hsa-miR-454-3p |
| hsa-miR-130a-3p |
| hsa-miR-29c-3p |
| hsa-miR-126-3p |
| hsa-miR-107 |
| hsa-miR-140-5p |
| hsa-miR-150-5p |
| hsa-miR-30d-5p |
| hsa-miR-10b-5p |
| hsa-miR-532-3p |
| hsa-miR-23a-5p |
| hsa-miR-29b-3p |
| hsa-miR-21-3p |
| hsa-miR-148a-3p |
| hsa-miR-136-5p |
| hsa-miR-1280 |
| hsa-miR-16-5p |

As mentioned above, the multivariant method may comprise may comprise determination of biomarkers as listed in Table 12, which comprises both miRNAs found to be associated with gastric cancer and miRNAs found to be not associated with gastric cancer. Thus, if in one example, the multivariant method uses miRNAs as listed in Table 19, the method would further comprises measuring the expression level of at least one miRNAs, which when compared to the negative control, the expression level is not altered in the subject. In one example, the miRNAs, which when compared to the negative control, the expression level is not altered in the subject, may be any one of the miRNAs as listed in Table 20.

Table 20 lists miRNAs frequently selected for use in multivariant biomarker panel where the expression levels of the miRNAs were not associated with gastric cancer subjects and is as follows:

| gastric cancer unrelated miRNA |
| --- |
| hsa-miR-532-5p |
| hsa-miR-30e-5p |
| hsa-miR-340-5p |
| hsa-miR-23b-3p |
| hsa-miR-224-5p |
| hsa-miR-185-5p |
| hsa-miR-320d |
| hsa-miR-374a-5p |
| hsa-miR-584-5p |
| hsa-miR-194-5p |

In one example, in the multivariant method as described herein, as known in the art, the score may calculate using a classification algorithm. In one example, the classification algorithm may include, but is not limited to, support vector machine algorithm, logistic regression algorithm, multinomial logistic regression algorithm, Fisher's linear discriminant algorithm, quadratic classifier algorithm, perceptron algorithm, k-nearest neighbors algorithm, artificial neural network algorithm, random forests algorithm, decision tree algorithm, naive Bayes algorithm, adaptive Bayes network algorithm, and ensemble learning method combining multiple learning algorithms. As would be appreciated by the skilled person in the art, the classification algorithm may be pre-trained using the expression level of the positive control and the negative control.

In the particular aspect of the multivariant method as described herein, the positive control may be a sample obtained from a subject with gastric cancer and the negative control is a sample obtained from a gastric cancer free control. In one example, the gastric cancer free control may be as described above. That is, in one example, the gastric cancer free control may be a subject without any gastric cancer related diseases. In one example, the gastric cancer free control may be a healthy subject without any existing diseases. In one example, the gastric cancer free control may be a subject known to have non-gastric cancer related diseases, such as, but is not limited to, gastritis, intestinal metaplasia, intestinal atrophy and the like. In one example, the control may vary on the nature of the sample as well as other factors such as the gender, age, ethnicity of the subjects based on whom the training data set was obtained from. In one example, the control subject may be of a Chinese ethnicity or ethnic Chinese descent.

As would be appreciated by those skilled in the art, the expression level of the miRNAs may be any one of concentration, log(concentration), Ct/Cq number, two to the power of Ct/Cq number and the like.

Figure 11:
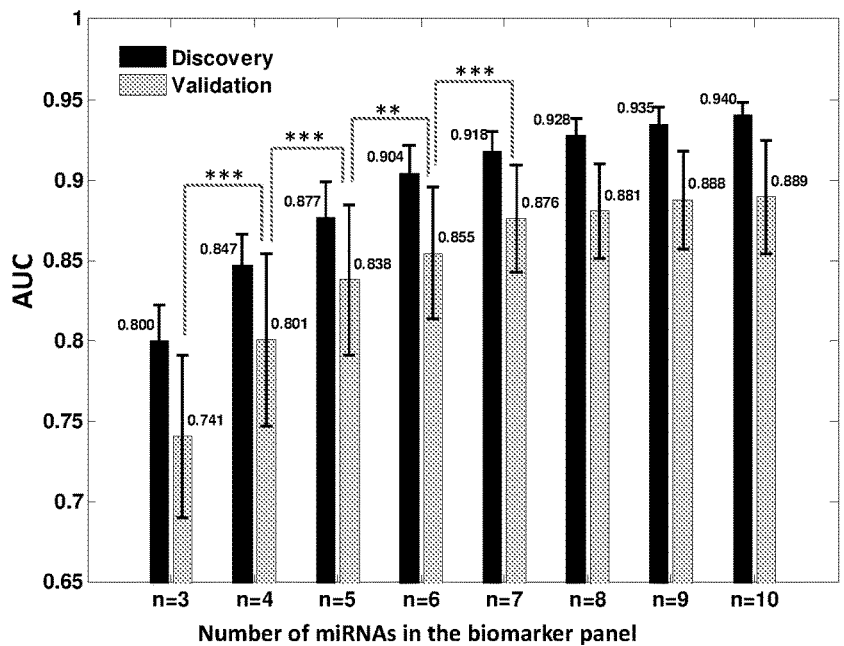
FIG. 11 shows a bar graph showing the means of AUC of various multivariant biomarker panels in the discovery set (black bars) and validations set (gray bars) during the cross validation processes. The error bar represented the standard deviation of the AUC. In order to test the significance of the AUC improvement in the validation set when more miRNAs were included in the panel, the right-tailed t-test was carried to compare all the adjacent gray bars. *: p-value<0.05; : p-value<0.01; *: p-value<0.001. Thus.

In one example, the method as described herein may use a data-trained formula that may be able to determine the likelihood of a subject having gastric cancer. In one example, the algorithm combines the measurement of multiple miRNA to give a score for the prediction of the risk of a subject having gastric cancer. It may combine the information of multiple genetic target and gives a better prediction accuracy than using single miRNA biomarker. In one example, the minimum number of miRNA biomarker to build a useful panel is 4. For example, it is shown in FIG. 11 that the biomarker panel with 4 miRNAs has an average AUC>0.8 in the validation set which is considered to be useful biomarker panel. The improvement on the performance of the biomarker panel (in terms of AUC values) does not increase significantly when the miRNA is more than 7. Accordingly, in one example, the minimum number of miRNA to build an optimum panel with maximized performance is 7 miRNAs. In one example, the formula that may be used for calculating the score for determining the likelihood of a subject having gastric cancer may be as follows:

$$A \times miRNA1 + B \times miRNA2 + C \times miRNA3 + D,$$

wherein miRNA1, miRNA2, miRNA3 were values related with the expression level of miRNA which can be the copy number, the log(copy number), the Ct/Cq number or others numbers; and A, B, C, D were the coefficients which can be positive or negative. For example, the score for determining the likelihood of a subject having gastric cancer (i.e. cancer risk score) may be calculated by combining 12 miRNAs (Table 21) frequently selected in the multivariant biomarker panel identification process with prevalence >20%, as described in the examples below and in FIG. 15. In one example, when a score is obtained from the formula, the higher/lower the score, the higher the chance of a subject having gastric cancer. In one example, the range may not be clearly defined as the coefficients may be scaled. For example, all coefficients (i.e. A, B, or C) may be half the amount or the value of D may be changed depending on training by the training data set. In one example, the value of the score may be positively or negatively correlated with the risk of having gastric cancer. The actual correlation would depend on the training data set and the skilled person in the art would be familiar with the necessary adjustment required upon establishment of the training data set.

In one example, the range may not be clearly defined as the coefficients may be scaled. For example, all coefficients (i.e. A, B, or C) may be twice the amount or the value of D may be changed depending on training by the training data set. In one example, the value of the score may be positively or negatively correlated with the risk of having gastric cancer. The actual correlation would depend on the training data set and the skilled person in the art would be familiar with the necessary adjustment required upon establishment of the training data set.

In one example, all coefficients (i.e. A, B, or C) may be purposely adjusted to half the amount and/or the value of D may be purposely changed to scale the range of the calculated value based on the formula for most of the subjects from 0 to 100. In one example, the value of the score may be positively or negatively correlated with the risk of having gastric cancer. The actual correlation would depend on the training data set and the skilled person in the art would be familiar with the necessary adjustment required upon establishment of the training data set.

In one example, the method as described herein may measure the expression level of at least one miRNA as listed as "significant" in Table 12 or as listed in Table 19 and at least one miRNA as listed as "insignificant" in Table 12 or as listed in Table 20. In one example, the method may measure the differential expression of at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or 42 miRNAs as listed as "significant" in Table 12 or at least two, or at least three, or at least four, or at least five, or at least six, or at least seven, or at least eight, or at least nine, or at least 10, or at least 11, or at least 12, or at least 13, or at least 14, or at least 15, or at least 20, or at least 25, or at least 30, or at least 35, or 38 of the miRNAs as listed in Table 19; and at least two, or at least three, or at least four, or at least five, or at least six, or at least seven, or at least eight, or at least nine, or 12 of the miRNAs as listed as "insignificant" in Table 12 or at least two, or at least three, or at least four, or at least five, or at least six, or at least seven, or at least eight, or at least nine, or 10 of the miRNAs as listed in Table 20.

In one example, when the multivariant method as described herein uses miRNAs related to gastric cancer as listed in Table 19, the method may further comprise measuring the expression level of any one or more of miRNAs selected from the group consisting of miR-21-5p, miR-20a-5pm, miR-17-5p, miR-423-5p and miR-223-3p.

In one example, wherein the multivariant method as described herein uses unrelated miRNAs as listed in Table 20, the method as described herein may further comprise measuring the expression level of any one or more of miRNAs selected from the group consisting of miR-34a-5p and miR-27b-3p.

Figure 2:
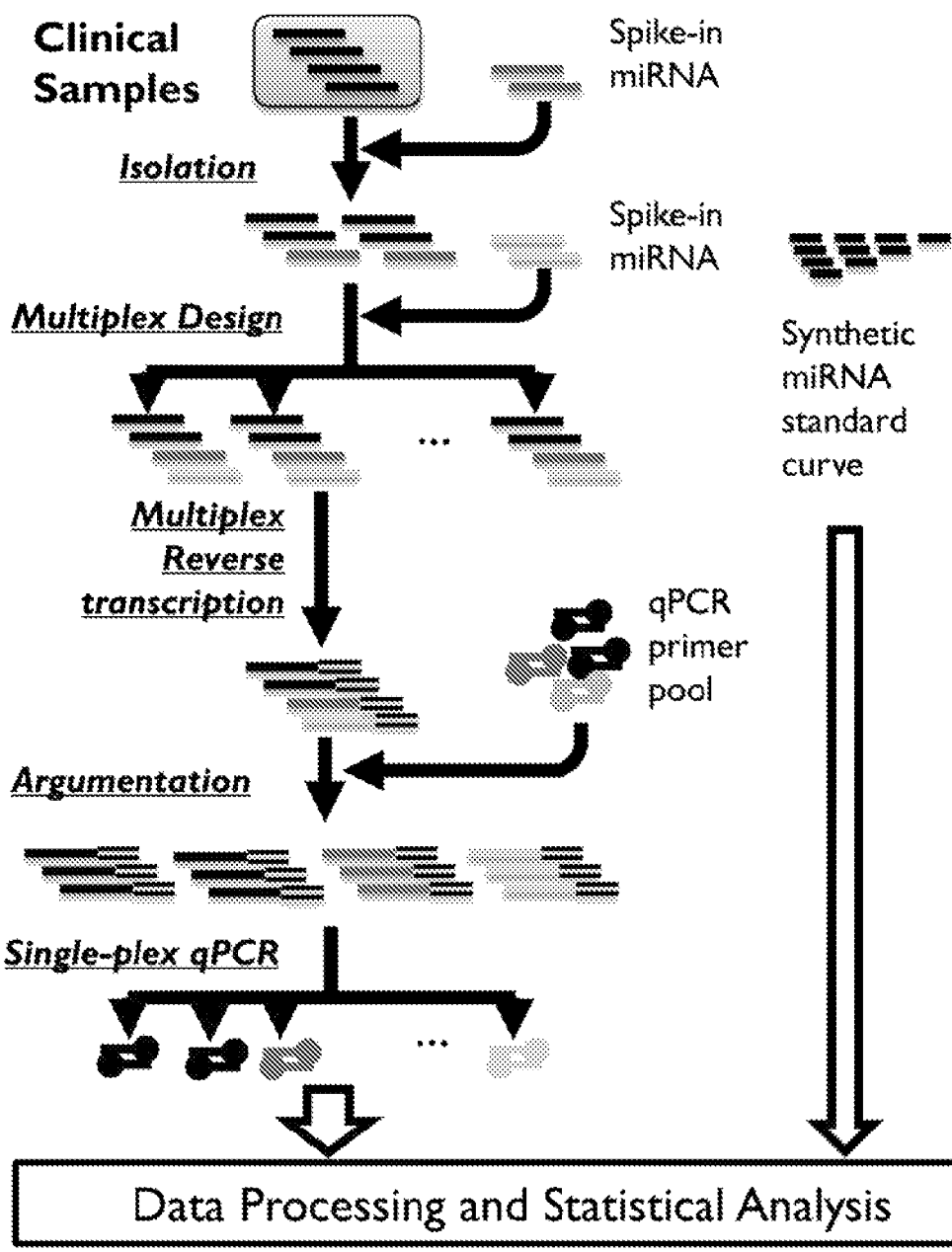
FIG. 2 shows an example of a workflow diagram of the high-throughput miRNA RT-qPCT measurement of miRNA detected in clinical samples.

An exemplary approach to arrive at miRNA sets that correlate with gastric cancer is summarized below. In addition, the general workflow is shown in FIGS. 1, 2 and 14.

Step 1: Total RNA (or subfractions thereof) is extracted from a sample (such as plasma, serum, or other blood fractions) of a subject or subjects with gastric cancer using suitable kits and/or purification methods.

Step 2: From the respective sample, the quantity (expression level) of one miRNA or sets of at least one miRNAs selected from the group consisting of SEQ ID NO: 1 to SEQ ID NO: 191 is measured using experimental techniques. In one example, the at least one miRNA may be selected from the group as listed in Tables 12, 19 and 20. These techniques are techniques known in the art, which may include, but are not limited to, array based approaches, amplification methods (PCR, RT-PCR, or qPCR), sequencing, next generation sequencing, and/or mass spectroscopy.

Step 3: In order to gather information on the diagnostic value and the redundancy of each of the single miRNA biomarkers, mathematical methods are applied. These methods are known methods in the art and may include, but are not limited to, basic mathematic approaches (e.g. Fold Quotients, Signal-to-Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3) is used to estimate for each miRNA biomarker the diagnostic content or value. Usually, however, this diagnostic value is too small to get a highly accurate diagnosis with accuracy rates, specificities and sensitivities beyond the 80% barrier. The diagnostic content of the miRNAs suitable for diagnosing gastric cancer is listed in FIG. 1. This Figure includes the miRNAs as listed in Tables 12, 19, and 20.

Step 5: In order to increase the performance for diagnosing of individuals suffering from gastric cancer, more than one miRNA biomarker may be employed. Thus statistical learning/machine learning/bioinformatics/computational approaches are applied for set selection in order to select/define sets of miRNA biomarkers (may comprising miRNAs as listed in Table 12 or Tables 19 and 20) that are tailored for the detection of gastric cancer. These techniques include, but are not limited to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least one, or at least two, or more for the set) to all measured miRNA, are then used to carry out a diagnosis of gastric cancer. To this end, statistical learning/machine learning/bioinformatics/computational approaches are applied that include, but are not limited to, any type of supervised or unsupervised analysis: classification techniques (e.g. naive Bayes, Linear Discriminant Analysis, Quadratic Discriminant Analysis Neural Nets, Tree based approaches, Support Vector Machines, Nearest Neighbor Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning approaches (Step 6) an algorithm or a mathematical function for diagnosing gastric cancer is obtained. This algorithm or mathematical function is applied to a miRNA expression profile (miRNA expression profile data) of an individual (subject) to be diagnosed for gastric cancer.

In any of the methods as described herein, the non-cellular biofluid may include any bodily fluid that does not include any cellular component of the fluid. Thus, in one example, upon extraction from the subject, the biofluid or bodily fluid may comprise cellular components generally found in a bodily fluid or biofluid of a subject. However, this biofluid or bodily fluid may be processed with methods known in the art to remove any cellular components contained within the biofluid or bodily fluid. For example, a centrifugation or purification process to remove cellular components of the bodily fluid or biofluid may be performed before the methods of the present disclosure may be conducted. Thus, in one example, the bodily fluid or non-cellular biofluid may include, but is not limited to non-cellular components of amniotic fluid, breast milk, bronchial lavage, cerebrospinal fluid, colostrum, interstitial fluid, peritoneal fluids, pleural fluid, saliva, seminal fluid, urine, tears, whole blood, including plasma, red blood cells, white blood cells and serum. In one example, the non-cellular biofluid may be serum or plasma.

As used herein, in any of the methods as described herein, the terms "subject" and "patient" may be used interchangeably to refer to an animal (e.g., a mammal, a fish, an amphibian, a reptile, a bird and an insect). In one example, the subject may be a mammal (e.g., a non-human mammal (such as a dog, a cat, or a primate) and a human). In one example, the subject may be a primate (e.g., a chimpanzee and a human). In one example, the subject may be a human. In one example, the subject may be a human with or without gastric (or stomach) cancer. In the Experimental section of the present disclosure, the training data set was obtained from subjects of Chinese ethnicity or Chinese descent. Thus, in one example, the subject may be of an Asian descent. In one example, the subject may be of a Chinese ethnicity or ethnic Chinese descent.

In one example, the methods as described herein may be provided as a kit. The kit may comprise components necessary or detecting the miRNAs as described herein. Components may include primers/probes that may hybridizes with the miRNAs as described herein, reagents, containers and/or equipment configured to detect miRNAs and primer/probes as described herein. In one example, the container within the kit may contain a primer/probe set that may detect or determine the level of the miRNAs as described herein that is radiolabelled before use. The kit may comprise containers of substances for reverse transcribing and amplifying one or more miRNAs, such as containers comprising dNTPs (each of the four deoxynucleotides dATP, dCTP, dGTP, and dTTP), buffers, reverse transcriptase and DNA polymerase. The kit may also comprise nucleic acid template(s) for a positive control and/or negative control reaction. The kits may further include any reaction components or buffer necessary for isolation of miRNAs from samples obtained from subjects.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Methods

Pre-Analytics (Sample Collection and microRNA Extraction):

Serum samples from normal (i.e. gastric cancer free control) and gastric cancer subjects were centrally collected by Singapore Gastric Cancer Consortium, processed and stored frozen at −80° C. Total RNA from 200 µl of serum were isolated using the well-established column based miRNeasy kit (Qiagen, Hilden, Germany), on a semi-automated QiaCube system. Serum contains minute amount of RNA. To reduce the loss of RNA and monitor extraction efficiency, rationally designed isolation enhancers (MS2) and spike-in control RNAs (MiRXES) were added to the specimen prior to isolation.

RT-qPCR:

The isolated total RNAs and synthetic RNA standards were converted to cDNA in optimized multiplex reverse transcription reactions with a second set of spike-in control RNAs to detect the presence of inhibitors and monitor the RT-qPCR efficiency. The Impron II (Promega®) reverse transcriptase was used to perform the reverse transcription following manufacture's instruction. The synthesized cDNA was then subjected to a multiplex augmentation step and quantified using a Sybr Green based single-plex qPCR assays (MIQE compliant) (MiRXES®). ABI® ViiA-7 384 machine was used for qPCR reactions. The overview and details of miRNA RT-qPCR measurement workflow is summarized in FIG. 2.

Data Processing:

The raw Cycles to Threshold (Ct) values were processed and the absolute copy numbers of the target miRNAs in each sample were determined through intra-polation of the synthetic miRNA standard curves. The technical variations introduced during RNA isolation and the processes of RT-qPCR were normalized by the spike-in control RNAs. For the analysis of single miRNA, the biological variations were further normalized by a set of validated endogenous reference miRNAs stably expressed across all control and disease samples.

Study Design

A well-designed clinical study (case-control study) was carried out to ensure the accurate identification of biomarkers for the diagnosis of gastric cancer. A total of 237 Chinese patients with gastric cancer of average age of 68.0±10.9 years old (stage 1 to 4) were used in this study and comparisons were made with another 236 age and sex matched normal (healthy/gastric cancer free) Chinese subjects, serving as the control group. All the cancer subjects were confirmed by endoscopy as well as biopsy and the serum samples were collected before any treatment. All the normal (healthy) subjects were confirmed gastric cancer free by endoscopy at the time when samples were collected and were followed up for 3-5 years with endoscopy screening every 2 years to ensure the subjects did not develop gastric cancer within this period of time. The detailed clinical information of the subjects was listed in Tables 2 and 3. All serum samples were stored at −80° C. prior to use. The characteristics of the studied subjects are summarized in Table 5. A large numbers of the control (normal/healthy/gastric cancer free subjects) subjects had gastric diseases such as gastritis, intestinal metaplasia and atrophy. Thus, the control group represented the high-risk population for gastric cancer. Although, the percentage of gastric cancer patients with *Helicobacter pylori* (78.8%) was more than that in the control group (55.7%), the marginal difference was insufficient to support the use *Helicobacter pylori* as a biomarker for gastric cancer.

TABLE 2

Clinical information of gastric cancer subjects

| S/N | Sex | Age | Classification | Stage | Gastritis | H Pylori | Intestinal Metaplasia | Atrophy |
|---|---|---|---|---|---|---|---|---|
| 1 | Female | 69 | Intestinal | 1a | Yes | Yes | Yes | No |
| 2 | Male | 64 | Intestinal | 1a | Yes | Yes | Yes | No |
| 3 | Male | 60 | Intestinal | 1a | Yes | Yes | Yes | No |
| 4 | Female | 77 | Intestinal | 1a | Yes | Yes | Yes | No |
| 5 | Female | 79 | Intestinal | 1a | Yes | Yes | Yes | No |
| 6 | Female | 78 | Intestinal | 1a | Yes | Yes | Yes | No |
| 7 | Female | 80 | Intestinal | 1a | Yes | No | Yes | No |
| 8 | Female | 83 | Intestinal | 1a | Yes | Yes | Yes | No |
| 9 | Male | 59 | Intestinal | 1a | Yes | Yes | Yes | No |
| 10 | Male | 78 | Intestinal | 1a | Yes | Yes | Yes | No |
| 11 | Female | 77 | Intestinal | 1a | Yes | Yes | Yes | No |
| 12 | Male | 56 | Intestinal | 1a | Yes | Yes | Yes | No |
| 13 | Male | 56 | Intestinal | 1a | Yes | Yes | Yes | No |
| 14 | Male | 67 | Intestinal | 1a | Yes | Yes | Yes | No |
| 15 | Female | 76 | Intestinal | 1a | Yes | Yes | Yes | No |
| 16 | Male | 62 | Intestinal | 1a | No | Yes | Yes | No |
| 17 | Male | 65 | Intestinal | 1a | Yes | Yes | No | No |
| 18 | Female | 68 | Intestinal | 1b | Yes | Yes | Yes | No |
| 19 | Male | 77 | Intestinal | 1b | Yes | Yes | Yes | No |
| 20 | Male | 78 | Intestinal | 1b | Yes | Yes | Yes | No |
| 21 | Female | 52 | Intestinal | 1b | Yes | No | No | No |
| 22 | Male | 65 | Intestinal | 1b | Yes | Yes | Yes | No |
| 23 | Female | 78 | Intestinal | 1b | Yes | Yes | Yes | No |
| 24 | Male | 82 | Intestinal | 1b | Yes | Yes | Yes | No |
| 25 | Male | 67 | Intestinal | 1b | Yes | Yes | Yes | Yes |
| 26 | Male | 77 | Intestinal | 1b | No | Yes | Yes | No |
| 27 | Male | 80 | Intestinal | 1b | Yes | Yes | Yes | No |
| 28 | Female | 78 | Intestinal | 1b | Yes | Yes | Yes | No |
| 29 | Male | 73 | Intestinal | 1b | Yes | Yes | Yes | No |
| 30 | Male | 56 | Intestinal | 1b | Yes | Yes | Yes | No |
| 31 | Female | 49 | Intestinal | 1b | Yes | No | No | No |
| 32 | Male | 78 | Intestinal | 1b | Yes | Yes | Yes | No |
| 33 | Female | 68 | Intestinal | 1b | Yes | Yes | No | No |
| 34 | Male | 71 | Intestinal | 1b | Yes | Yes | Yes | No |
| 35 | Female | 44 | Intestinal | 1b | Yes | Yes | Yes | No |
| 36 | Male | 72 | Intestinal | 1b | Yes | Yes | Yes | No |
| 37 | Female | 81 | Intestinal | 2 | Yes | Yes | Yes | No |
| 38 | Female | 49 | Intestinal | 2 | Yes | Yes | No | No |
| 39 | Male | 67 | Intestinal | 2 | No | Yes | No | No |
| 40 | Male | 58 | Intestinal | 2 | Yes | No | No | No |
| 41 | Female | 57 | Intestinal | 2 | No | Yes | Yes | No |
| 42 | Male | 72 | Intestinal | 2 | Yes | Yes | No | No |
| 43 | Female | 73 | Intestinal | 2 | Yes | Yes | Yes | No |
| 44 | Male | 88 | Intestinal | 2 | Yes | Yes | Yes | No |

TABLE 2-continued

Clinical information of gastric cancer subjects

| S/N | Sex | Age | Classification | Stage | Gastritis | H Pylori | Intestinal Metaplasia | Atrophy |
|---|---|---|---|---|---|---|---|---|
| 45 | Male | 56 | Intestinal | 2 | Yes | Yes | No | No |
| 46 | Female | 74 | Intestinal | 2 | Yes | Yes | Yes | No |
| 47 | Male | 61 | Intestinal | 2 | Yes | Yes | Yes | No |
| 48 | Female | 75 | Intestinal | 2 | Yes | Yes | Yes | No |
| 49 | Male | 80 | Intestinal | 2 | Yes | Yes | Yes | No |
| 50 | Female | 56 | Intestinal | 2 | Yes | Yes | Yes | No |
| 51 | Male | 65 | Intestinal | 2 | Yes | Yes | Yes | No |
| 52 | Male | 72 | Intestinal | 2 | Yes | Yes | No | Yes |
| 53 | Male | 71 | Intestinal | 2 | Yes | Yes | Yes | No |
| 54 | Male | 59 | Intestinal | 2 | Yes | Yes | No | No |
| 55 | Male | 80 | Intestinal | 2 | Yes | Yes | Yes | No |
| 56 | Female | 78 | Intestinal | 2 | Yes | No | Yes | Yes |
| 57 | Male | 74 | Intestinal | 2 | Yes | Yes | Yes | No |
| 58 | Female | 83 | Intestinal | 2 | Yes | Yes | Yes | No |
| 59 | Male | 72 | Intestinal | 2 | Yes | Yes | Yes | No |
| 60 | Female | 49 | Intestinal | 2 | Yes | Yes | Yes | No |
| 61 | Male | 72 | Intestinal | 3a | Yes | No | Yes | No |
| 62 | Female | 55 | Intestinal | 3a | Yes | Yes | No | Yes |
| 63 | Male | 75 | Intestinal | 3a | Yes | Yes | Yes | No |
| 64 | Male | 67 | Intestinal | 3a | Yes | Yes | Yes | No |
| 65 | Male | 76 | Intestinal | 3a | Yes | Yes | Yes | No |
| 66 | Male | 72 | Intestinal | 3a | Yes | Yes | Yes | No |
| 67 | Female | 70 | Intestinal | 3a | Yes | Yes | Yes | No |
| 68 | Male | 63 | Intestinal | 3a | Yes | Yes | Yes | No |
| 69 | Male | 75 | Intestinal | 3a | Yes | Yes | Yes | No |
| 70 | Male | 66 | Intestinal | 3a | Yes | Yes | No | No |
| 71 | Female | 71 | Intestinal | 3a | Yes | Yes | No | No |
| 72 | Female | 75 | Intestinal | 3a | No | Yes | Yes | No |
| 73 | Female | 67 | Intestinal | 3a | Yes | Yes | No | No |
| 74 | Male | 81 | Intestinal | 3a | Yes | Yes | Yes | No |
| 75 | Male | 66 | Intestinal | 3a | Yes | Yes | Yes | No |
| 76 | Male | 54 | Intestinal | 3a | Yes | Yes | Yes | No |
| 77 | Male | 72 | Intestinal | 3a | Yes | Yes | Yes | No |
| 78 | Male | 76 | Intestinal | 3a | Yes | Yes | Yes | No |
| 79 | Male | 65 | Intestinal | 3a | Yes | No | Yes | No |
| 80 | Female | 80 | Intestinal | 3b | Yes | No | Yes | No |
| 81 | Male | 77 | Intestinal | 3b | Yes | Yes | No | No |
| 82 | Male | 69 | Intestinal | 3b | Yes | Yes | Yes | No |
| 83 | Male | 70 | Intestinal | 3b | No | Yes | No | No |
| 84 | Female | 85 | Intestinal | 3b | Yes | Yes | Yes | No |
| 85 | Male | 60 | Intestinal | 3b | Yes | Yes | No | No |
| 86 | Male | 79 | Intestinal | 3b | Yes | Yes | Yes | No |
| 87 | Female | 68 | Intestinal | 3b | Yes | Yes | No | No |
| 88 | Male | 78 | Mixed | 3b | Yes | Yes | Yes | No |
| 89 | Male | 50 | Mixed | 1a | Yes | No | Yes | No |
| 90 | Male | 90 | Mixed | 1b | Yes | Yes | Yes | No |
| 91 | Female | 60 | Mixed | 4 | No | Yes | No | No |
| 92 | Female | 56 | Mixed | 4 | Yes | Yes | Yes | No |
| 93 | Female | 78 | Intestinal | 1b | No | No | No | No |
| 94 | Male | 66 | Intestinal | 2 | Yes | No | Yes | No |
| 95 | Male | 81 | Mixed | 3a | Yes | No | Yes | No |
| 96 | Male | 68 | Intestinal | 4 | Yes | Yes | Yes | No |
| 97 | Female | 69 | Intestinal | 4 | Yes | No | Yes | No |
| 98 | Male | 89 | Intestinal | 1a | Yes | Yes | Yes | Yes |
| 99 | Male | 79 | Intestinal | 1a | Yes | No | Yes | Yes |
| 100 | Male | 81 | Intestinal | 4 | Yes | No | Yes | Yes |
| 101 | Male | 67 | Intestinal | 4 | Yes | No | No | No |
| 102 | Male | 76 | Diffuse | 3a | Yes | Yes | Yes | Yes |
| 103 | Male | 62 | Diffuse | 4 | Yes | Yes | Yes | Yes |
| 104 | Male | 71 | Intestinal | 1a | Yes | No | Yes | Yes |
| 105 | Female | 78 | Diffuse | 3b | No | Yes | No | No |
| 106 | Male | 57 | Intestinal | 2 | Yes | No | No | No |
| 107 | Female | 68 | Diffuse | 3b | Yes | Yes | Yes | No |
| 108 | Female | 68 | Diffuse | 4 | Yes | Yes | Yes | No |
| 109 | Male | 58 | Diffuse | 3a | Yes | No | No | No |
| 110 | Male | 86 | Mixed | 4 | No | Yes | Yes | No |
| 111 | Female | 56 | Diffuse | 1a | Yes | Yes | Yes | No |
| 112 | Male | 68 | Diffuse | 4 | Yes | Yes | No | No |
| 113 | Female | 83 | Diffuse | 1a | Yes | Yes | Yes | No |
| 114 | Male | 73 | Diffuse | 2 | Yes | Yes | Yes | No |
| 115 | Male | 79 | Diffuse | 3b | Yes | Yes | No | No |
| 116 | Male | 58 | Diffuse | 3a | Yes | Yes | Yes | No |
| 117 | Male | 74 | Mixed | 4 | No | Yes | No | No |
| 118 | Male | 64 | Diffuse | 1a | Yes | No | Yes | No |
| 119 | Male | 66 | Intestinal | 4 | Yes | No | Yes | No |

TABLE 2-continued

Clinical information of gastric cancer subjects

| S/N | Sex | Age | Classification | Stage | Gastritis | H Pylori | Intestinal Metaplasia | Atrophy |
|---|---|---|---|---|---|---|---|---|
| 120 | Female | 76 | Diffuse | 4 | Yes | Yes | Yes | No |
| 121 | Female | 79 | Diffuse | 2 | Yes | Yes | No | No |
| 122 | Female | 71 | Intestinal | 4 | No | Yes | No | No |
| 123 | Female | 64 | Diffuse | 4 | Yes | Yes | Yes | No |
| 124 | Female | 57 | Diffuse | 3b | Yes | Yes | Yes | No |
| 125 | Female | 60 | Diffuse | 4 | No | Yes | No | No |
| 126 | Male | 63 | Diffuse | 1a | No | Yes | Yes | No |
| 127 | Female | 71 | Diffuse | 3a | Yes | Yes | No | No |
| 128 | Male | 57 | Diffuse | 1a | Yes | Yes | No | No |
| 129 | Male | 75 | Mixed | 4 | Yes | Yes | Yes | No |
| 130 | Male | 43 | Mixed | 4 | Yes | Yes | No | No |
| 131 | Male | 29 | Diffuse | 3a | Yes | Yes | Yes | Yes |
| 132 | Male | 59 | Intestinal | 4 | Yes | Yes | Yes | Yes |
| 133 | Male | 63 | Diffuse | 2 | Yes | Yes | Yes | No |
| 134 | Male | 72 | Diffuse | 4 | No | Yes | Yes | No |
| 135 | Male | 54 | Mixed | 2 | Yes | No | No | No |
| 136 | Male | 61 | Mixed | 3a | Yes | Yes | Yes | No |
| 137 | Female | 58 | Mixed | 1a | Yes | Yes | Yes | No |
| 138 | Male | 68 | Intestinal | 4 | Yes | Yes | Yes | No |
| 139 | Male | 69 | Intestinal | 4 | Yes | Yes | Yes | No |
| 140 | Male | 61 | Intestinal | 4 | Yes | No | No | No |
| 141 | Male | 75 | Intestinal | 4 | No | Yes | No | No |
| 142 | Female | 66 | Diffuse | 3a | No | No | No | Yes |
| 143 | Male | 76 | Diffuse | 4 | No | No | No | No |
| 144 | Male | 70 | Intestinal | 4 | No | Yes | No | No |
| 145 | Female | 71 | Diffuse | 4 | Yes | Yes | Yes | No |
| 146 | Male | 56 | Intestinal | 4 | Yes | Yes | Yes | No |
| 147 | Female | 69 | Mixed | 1a | Yes | Yes | Yes | No |
| 148 | Male | 71 | Mixed | 2 | Yes | Yes | Yes | No |
| 149 | Female | 53 | Intestinal | 1a | Yes | No | Yes | No |
| 150 | Male | 70 | Mixed | 4 | Yes | Yes | No | No |
| 151 | Male | 71 | Diffuse | 1a | Yes | Yes | No | No |
| 152 | Female | 72 | Intestinal | 4 | No | Yes | No | No |
| 153 | Male | 64 | Diffuse | 3b | Yes | Yes | No | No |
| 154 | Female | 55 | Diffuse | 1a | Yes | Yes | Yes | No |
| 155 | Male | 44 | Diffuse | 4 | Yes | Yes | Yes | No |
| 156 | Male | 77 | Intestinal | 4 | Yes | No | Yes | No |
| 157 | Female | 75 | Diffuse | 4 | Yes | No | No | No |
| 158 | Male | 78 | Intestinal | 4 | Yes | Yes | Yes | No |
| 159 | Female | 68 | Intestinal | 4 | No | Yes | Yes | No |
| 160 | Female | 69 | Mixed | 4 | Yes | Yes | Yes | Yes |
| 161 | Male | 46 | Intestinal | 1b | Yes | No | No | No |
| 162 | Male | 66 | Diffuse | 3a | Yes | No | Yes | No |
| 163 | Female | 51 | Mixed | 1b | Yes | Yes | Yes | No |
| 164 | Male | 54 | Intestinal | 4 | No | No | No | No |
| 165 | Female | 61 | Mixed | 4 | Yes | Yes | Yes | No |
| 166 | Male | 51 | Diffuse | 4 | No | Yes | Yes | No |
| 167 | Male | 70 | Diffuse | 3a | Yes | Yes | Yes | No |
| 168 | Male | 69 | Mixed | 3a | Yes | Yes | No | No |
| 169 | Male | 73 | Diffuse | 3a | Yes | Yes | Yes | No |
| 170 | Male | 89 | Mixed | 4 | Yes | Yes | No | No |
| 171 | Male | 73 | Mixed | 2 | Yes | No | Yes | No |
| 172 | Female | 69 | Mixed | 1a | Yes | No | Yes | No |
| 173 | Male | 84 | Intestinal | 4 | No | Yes | No | No |
| 174 | Male | 75 | Intestinal | 1b | Yes | Yes | Yes | No |
| 175 | Female | 63 | Mixed | 3a | Yes | No | No | No |
| 176 | Male | 80 | Mixed | 4 | Yes | No | Yes | No |
| 177 | Female | 60 | Diffuse | 3a | No | Yes | No | No |
| 178 | Male | 72 | Diffuse | 2 | Yes | Yes | Yes | No |
| 179 | Female | 53 | Diffuse | 4 | Yes | Yes | No | No |
| 180 | Female | 60 | Diffuse | 4 | Yes | Yes | No | No |
| 181 | Male | 44 | Diffuse | 4 | Yes | No | No | No |
| 182 | Female | 64 | Intestinal | 1a | Yes | No | Yes | No |
| 183 | Male | 57 | Mixed | 1a | Yes | Yes | Yes | Yes |
| 184 | Male | 61 | Diffuse | 1b | Yes | Yes | Yes | No |
| 185 | Female | 59 | Mixed | 4 | Yes | Yes | Yes | No |
| 186 | Female | 81 | Diffuse | 3b | Yes | Yes | Yes | Yes |
| 187 | Male | 78 | Diffuse | 4 | Yes | Yes | Yes | No |
| 188 | Male | 73 | Diffuse | 1b | Yes | No | Yes | No |
| 189 | Male | 64 | Mixed | 3a | Yes | Yes | No | No |
| 190 | Male | 73 | Intestinal | 4 | No | Yes | Yes | Yes |
| 191 | Female | 76 | Intestinal | 4 | Yes | No | Yes | No |
| 192 | Female | 72 | Diffuse | 4 | No | Yes | No | No |
| 193 | Male | 82 | Diffuse | 1b | Yes | Yes | Yes | No |
| 194 | Male | 55 | Diffuse | 1a | Yes | Yes | Yes | No |

TABLE 2-continued

Clinical information of gastric cancer subjects

| S/N | Sex | Age | Classification | Stage | Gastritis | H Pylori | Intestinal Metaplasia | Atrophy |
|---|---|---|---|---|---|---|---|---|
| 195 | Male | 70 | Intestinal | 4 | Yes | Yes | Yes | No |
| 196 | Male | 67 | Diffuse | 1b | Yes | Yes | No | No |
| 197 | Male | 64 | Diffuse | 4 | Yes | Yes | No | No |
| 198 | Male | 67 | Intestinal | 4 | Yes | Yes | Yes | No |
| 199 | Female | 68 | Diffuse | 4 | Yes | Yes | No | No |
| 200 | Female | 62 | Diffuse | 4 | No | No | No | No |
| 201 | Female | 74 | Diffuse | 4 | Yes | Yes | Yes | No |
| 202 | Male | 77 | Intestinal | 4 | No | Yes | Yes | No |
| 203 | Female | 73 | Mixed | 4 | Yes | Yes | Yes | No |
| 204 | Male | 77 | Intestinal | 4 | Yes | Yes | Yes | No |
| 205 | Female | 56 | Diffuse | 1a | Yes | Yes | Yes | No |
| 206 | Male | 54 | Diffuse | 4 | No | Yes | No | No |
| 207 | Female | 76 | Intestinal | 1b | No | Yes | No | No |
| 208 | Male | 82 | Diffuse | 3a | No | Yes | Yes | No |
| 209 | Male | 55 | Diffuse | 4 | Yes | No | No | No |
| 210 | Male | 73 | Diffuse | 4 | No | Yes | No | No |
| 211 | Male | 69 | Intestinal | 4 | Yes | Yes | Yes | Yes |
| 212 | Female | 78 | Diffuse | 1b | Yes | No | Yes | No |
| 213 | Male | 63 | Intestinal | 4 | Yes | Yes | No | No |
| 214 | Female | 88 | Intestinal | 4 | Yes | Yes | No | No |
| 215 | Male | 76 | Mixed | 3a | Yes | No | No | No |
| 216 | Female | 50 | Diffuse | 1a | Yes | Yes | Yes | No |
| 217 | Male | 75 | Intestinal | 4 | Yes | Yes | Yes | Yes |
| 218 | Male | 37 | Diffuse | 4 | No | No | Yes | No |
| 219 | Male | 64 | Intestinal | 4 | Yes | Yes | No | No |
| 220 | Female | 85 | Diffuse | 4 | Yes | Yes | Yes | No |
| 221 | Female | 52 | Diffuse | 2 | Yes | Yes | No | No |
| 222 | Female | 67 | Intestinal | 2 | Yes | No | Yes | No |
| 223 | Male | 86 | Mixed | 1a | Yes | Yes | Yes | No |
| 224 | Female | 71 | Diffuse | 1a | Yes | Yes | Yes | Yes |
| 225 | Male | 53 | Diffuse | 3a | Yes | Yes | No | No |
| 226 | Female | 80 | Diffuse | 3b | Yes | No | Yes | No |
| 227 | Male | 53 | Diffuse | 4 | No | Yes | No | No |
| 228 | Male | 55 | Diffuse | 3b | Yes | No | Yes | No |
| 229 | Male | 43 | Diffuse | 4 | Yes | Yes | Yes | No |
| 230 | Female | 81 | Intestinal | 4 | No | Yes | No | No |
| 231 | Male | 79 | Intestinal | 2 | Yes | No | Yes | No |
| 232 | Female | 38 | Intestinal | 4 | Yes | Yes | Yes | No |
| 233 | Male | 78 | Mixed | 4 | Yes | Yes | No | No |
| 234 | Female | 81 | Intestinal | 1b | Yes | No | Yes | Yes |
| 235 | Male | 78 | Intestinal | 1b | Yes | No | Yes | No |
| 236 | Male | 48 | Diffuse | 4 | Yes | Yes | No | No |

TABLE 3

Clinical information of control subjects

| S/N | Sex | Age | Gastritis | H Pylori | Intestinal Metaplasia | Atrophy |
|---|---|---|---|---|---|---|
| 1 | Female | 55 | Yes | No | Yes | No |
| 2 | Female | 71 | Yes | Yes | Yes | No |
| 3 | Male | 60 | Yes | Yes | Yes | Yes |
| 4 | Female | 60 | Yes | No | Yes | Yes |
| 5 | Male | 70 | Yes | Yes | Yes | Yes |
| 6 | Male | 55 | Yes | Yes | Yes | Yes |
| 7 | Male | 51 | Yes | Yes | Yes | Yes |
| 8 | Female | 56 | Yes | Yes | Yes | Yes |
| 9 | Male | 64 | Yes | Yes | Yes | Yes |
| 10 | Male | 72 | Yes | Yes | No | No |
| 11 | Female | 60 | Yes | Yes | Yes | No |
| 12 | Female | 50 | Yes | Yes | Yes | Yes |
| 13 | Male | 70 | Yes | Yes | Yes | No |
| 14 | Female | 55 | Yes | Yes | Yes | Yes |
| 15 | Female | 69 | Yes | Yes | Yes | Yes |
| 16 | Male | 71 | Yes | Yes | Yes | Yes |
| 17 | Female | 72 | Yes | Yes | Yes | Yes |
| 18 | Male | 60 | Yes | No | Yes | No |
| 19 | Female | 67 | Yes | Yes | Yes | Yes |
| 20 | Male | 62 | Yes | Yes | No | No |
| 21 | Male | 60 | Yes | Yes | No | No |
| 22 | Male | 70 | Yes | Yes | Yes | Yes |
| 23 | Male | 71 | Yes | No | No | No |
| 24 | Female | 50 | Yes | Yes | Yes | Yes |
| 25 | Male | 71 | Yes | Yes | Yes | Yes |
| 26 | Male | 50 | Yes | Yes | No | No |
| 27 | Male | 64 | Yes | Yes | Yes | Yes |
| 28 | Male | 50 | Yes | Yes | Yes | Yes |
| 29 | Female | 50 | Yes | Yes | Yes | No |
| 30 | Male | 68 | Yes | Yes | No | No |
| 31 | Female | 73 | Yes | Yes | No | No |
| 32 | Male | 68 | Yes | Yes | Yes | Yes |
| 33 | Female | 63 | Yes | No | No | No |
| 34 | Male | 69 | Yes | Yes | Yes | Yes |
| 35 | Female | 50 | Yes | No | No | No |
| 36 | Male | 70 | Yes | Yes | Yes | Yes |
| 37 | Male | 64 | Yes | Yes | Yes | Yes |
| 38 | Male | 72 | Yes | Yes | Yes | Yes |
| 39 | Female | 65 | Yes | No | Yes | Yes |
| 40 | Female | 55 | Yes | Yes | No | No |
| 41 | Male | 63 | Yes | Yes | Yes | Yes |
| 42 | Male | 65 | Yes | Yes | Yes | Yes |
| 43 | Male | 66 | Yes | Yes | Yes | Yes |
| 44 | Male | 74 | Yes | Yes | Yes | No |

TABLE 3-continued

Clinical information of control subjects

| S/N | Sex | Age | Gastritis | H Pylori | Intestinal Metaplasia | Atrophy |
|---|---|---|---|---|---|---|
| 45 | Male | 62 | Yes | No | Yes | Yes |
| 46 | Female | 63 | Yes | Yes | Yes | No |
| 47 | Female | 65 | Yes | No | No | No |
| 48 | Male | 60 | Yes | Yes | Yes | No |
| 49 | Male | 50 | Yes | No | No | No |
| 50 | Female | 50 | Yes | No | No | No |
| 51 | Male | 50 | Yes | Yes | Yes | Yes |
| 52 | Female | 50 | Yes | Yes | Yes | Yes |
| 53 | Male | 69 | Yes | Yes | Yes | Yes |
| 54 | Female | 55 | Yes | Yes | Yes | Yes |
| 55 | Female | 50 | Yes | Yes | Yes | Yes |
| 56 | Female | 50 | Yes | No | Yes | Yes |
| 57 | Male | 74 | Yes | No | No | No |
| 58 | Male | 72 | Yes | Yes | Yes | Yes |
| 59 | Female | 50 | Yes | Yes | Yes | Yes |
| 60 | Male | 82 | Yes | Yes | Yes | Yes |
| 61 | Male | 69 | Yes | No | Yes | Yes |
| 62 | Male | 68 | Yes | Yes | Yes | Yes |
| 63 | Male | 61 | Yes | Yes | Yes | Yes |
| 64 | Male | 68 | Yes | No | No | No |
| 65 | Male | 50 | Yes | Yes | Yes | Yes |
| 66 | Female | 61 | Yes | Yes | Yes | Yes |
| 67 | Male | 67 | Yes | Yes | Yes | No |
| 68 | Male | 65 | Yes | Yes | Yes | Yes |
| 69 | Female | 62 | Yes | Yes | Yes | Yes |
| 70 | Male | 77 | Yes | No | Yes | Yes |
| 71 | Male | 62 | Yes | Yes | Yes | Yes |
| 72 | Male | 63 | Yes | No | No | No |
| 73 | Male | 64 | Yes | Yes | Yes | Yes |
| 74 | Male | 50 | Yes | Yes | No | No |
| 75 | Male | 62 | Yes | Yes | Yes | Yes |
| 76 | Female | 60 | Yes | Yes | No | No |
| 77 | Male | 63 | Yes | Yes | Yes | Yes |
| 78 | Female | 55 | No | No | No | No |
| 79 | Male | 66 | Yes | Yes | Yes | Yes |
| 80 | Female | 75 | Yes | Yes | Yes | Yes |
| 81 | Male | 71 | Yes | Yes | Yes | Yes |
| 82 | Male | 61 | Yes | No | No | No |
| 83 | Female | 54 | Yes | No | No | No |
| 84 | Female | 50 | Yes | No | No | No |
| 85 | Male | 63 | Yes | Yes | Yes | Yes |
| 86 | Male | 66 | Yes | Yes | Yes | Yes |
| 87 | Female | 60 | Yes | No | Yes | Yes |
| 88 | Male | 65 | Yes | Yes | Yes | Yes |
| 89 | Female | 82 | Yes | Yes | Yes | No |
| 90 | Male | 63 | Yes | No | No | No |
| 91 | Male | 57 | Yes | No | No | No |
| 92 | Male | 65 | Yes | Yes | No | Yes |
| 93 | Female | 62 | Yes | Yes | No | No |
| 94 | Male | 79 | Yes | Yes | Yes | No |
| 95 | Male | 51 | Yes | Yes | Yes | Yes |
| 96 | Male | 52 | Yes | No | No | No |
| 97 | Male | 52 | Yes | Yes | Yes | Yes |
| 98 | Male | 52 | Yes | Yes | Yes | Yes |
| 99 | Male | 51 | Yes | No | No | No |
| 100 | Male | 53 | No | No | No | No |
| 101 | Male | 60 | Yes | No | Yes | No |
| 102 | Female | 70 | Yes | No | No | No |
| 103 | Female | 52 | Yes | No | No | No |
| 104 | Male | 55 | Yes | No | No | No |
| 105 | Male | 66 | Yes | No | No | No |
| 106 | Female | 50 | Yes | Yes | No | No |
| 107 | Male | 65 | Yes | Yes | Yes | Yes |
| 108 | Male | 55 | Yes | No | No | No |
| 109 | Female | 71 | Yes | Yes | Yes | Yes |
| 110 | Female | 42 | Yes | Yes | Yes | Yes |
| 111 | Male | 50 | Yes | No | Yes | No |
| 112 | Male | 56 | Yes | No | No | No |
| 113 | Male | 71 | Yes | No | No | Yes |
| 114 | Male | 67 | Yes | Yes | Yes | Yes |
| 115 | Female | 63 | Yes | No | No | No |
| 116 | Male | 76 | Yes | Yes | Yes | Yes |
| 117 | Female | 50 | Yes | Yes | No | No |
| 118 | Male | 56 | No | No | No | No |
| 119 | Male | 52 | Yes | No | No | No |
| 120 | Male | 40 | Yes | Yes | Yes | Yes |
| 121 | Female | 69 | Yes | No | No | No |
| 122 | Male | 68 | Yes | Yes | Yes | Yes |
| 123 | Female | 56 | Yes | No | No | No |
| 124 | Female | 51 | Yes | No | No | No |
| 125 | Male | 63 | Yes | Yes | Yes | Yes |
| 126 | Male | 57 | Yes | No | No | No |
| 127 | Male | 48 | Yes | Yes | Yes | Yes |
| 128 | Female | 51 | Yes | Yes | No | No |
| 129 | Male | 60 | Yes | No | No | No |
| 130 | Female | 67 | Yes | Yes | Yes | Yes |
| 131 | Female | 52 | Yes | No | No | No |
| 132 | Male | 63 | Yes | Yes | Yes | Yes |
| 133 | Female | 57 | Yes | Yes | No | No |
| 134 | Male | 63 | Yes | Yes | Yes | Yes |
| 135 | Female | 50 | Yes | No | Yes | No |
| 136 | Female | 60 | Yes | No | No | No |
| 137 | Female | 62 | Yes | No | No | No |
| 138 | Male | 70 | Yes | Yes | Yes | Yes |
| 139 | Female | 51 | Yes | No | No | No |
| 140 | Male | 64 | Yes | Yes | Yes | Yes |
| 141 | Female | 59 | Yes | No | No | No |
| 142 | Male | 68 | Yes | Yes | Yes | Yes |
| 143 | Male | 65 | Yes | No | No | No |
| 144 | Male | 69 | Yes | No | No | No |
| 145 | Male | 66 | Yes | Yes | Yes | Yes |
| 146 | Male | 81 | Yes | No | No | No |
| 147 | Male | 73 | Yes | Yes | Yes | Yes |
| 148 | Male | 67 | Yes | No | No | No |
| 149 | Female | 61 | Yes | No | Yes | No |
| 150 | Female | 53 | Yes | No | No | No |
| 151 | Male | 50 | Yes | No | No | No |
| 152 | Male | 67 | Yes | Yes | Yes | Yes |
| 153 | Male | 52 | Yes | Yes | Yes | Yes |
| 154 | Male | 52 | Yes | No | No | No |
| 155 | Male | 60 | Yes | No | No | No |
| 156 | Male | 62 | Yes | No | No | No |
| 157 | Male | 53 | Yes | No | No | No |
| 158 | Male | 51 | Yes | Yes | Yes | Yes |
| 159 | Female | 57 | No | No | No | No |
| 160 | Female | 54 | Yes | No | No | No |
| 161 | Female | 77 | Yes | Yes | Yes | Yes |
| 162 | Female | 54 | Yes | No | No | No |
| 163 | Female | 51 | Yes | Yes | No | No |
| 164 | Female | 56 | Yes | No | No | No |
| 165 | Male | 68 | Yes | Yes | Yes | No |
| 166 | Female | 52 | Yes | No | No | No |
| 167 | Female | 73 | Yes | Yes | Yes | Yes |
| 168 | Male | 50 | Yes | Yes | Yes | Yes |
| 169 | Male | 63 | Yes | Yes | Yes | Yes |
| 170 | Male | 71 | Yes | Yes | Yes | Yes |
| 171 | Female | 52 | Yes | No | No | No |
| 172 | Male | 76 | Yes | No | No | No |
| 173 | Female | 54 | Yes | No | No | No |
| 174 | Male | 56 | Yes | No | No | No |
| 175 | Male | 62 | Yes | No | No | No |
| 176 | Male | 64 | Yes | No | No | No |
| 177 | Female | 51 | Yes | No | No | No |
| 178 | Male | 76 | Yes | Yes | Yes | Yes |
| 179 | Female | 53 | No | No | No | Yes |
| 180 | Male | 61 | Yes | No | No | No |
| 181 | Female | 56 | No | No | No | No |
| 182 | Male | 56 | Yes | No | No | No |
| 183 | Male | 60 | Yes | No | No | No |
| 184 | Male | 54 | Yes | Yes | No | No |
| 185 | Male | 67 | Yes | No | No | No |
| 186 | Female | 58 | No | No | No | No |
| 187 | Male | 56 | Yes | No | No | No |
| 188 | Male | 67 | Yes | No | No | No |
| 189 | Female | 61 | Yes | No | No | No |
| 190 | Female | 60 | Yes | Yes | No | No |
| 191 | Female | 52 | Yes | No | No | No |
| 192 | Female | 55 | Yes | No | No | No |
| 193 | Male | 69 | Yes | No | Yes | No |
| 194 | Male | 69 | Yes | Yes | Yes | Yes |

TABLE 3-continued

Clinical information of control subjects

| S/N | Sex | Age | Gastritis | H Pylori | Intestinal Metaplasia | Atrophy |
|---|---|---|---|---|---|---|
| 195 | Female | 51 | Yes | Yes | No | No |
| 196 | Male | 52 | Yes | Yes | No | Yes |
| 197 | Male | 54 | Yes | No | No | No |
| 198 | Male | 66 | Yes | Yes | Yes | Yes |
| 199 | Female | 50 | Yes | Yes | No | No |
| 200 | Female | 58 | Yes | No | No | No |
| 201 | Female | 59 | Yes | Yes | Yes | No |
| 202 | Female | 65 | Yes | No | No | No |
| 203 | Female | 73 | Yes | Yes | Yes | Yes |
| 204 | Male | 67 | Yes | Yes | Yes | Yes |
| 205 | Male | 66 | Yes | Yes | Yes | Yes |
| 206 | Male | 78 | Yes | Yes | No | No |
| 207 | Female | 69 | Yes | Yes | No | No |
| 208 | Male | 57 | Yes | No | No | No |
| 209 | Male | 66 | Yes | Yes | Yes | Yes |
| 210 | Male | 51 | Yes | No | No | No |
| 211 | Male | 67 | Yes | Yes | Yes | Yes |
| 212 | Female | 77 | Yes | Yes | Yes | No |
| 213 | Male | 66 | Yes | No | No | No |
| 214 | Male | 74 | Yes | Yes | Yes | Yes |
| 215 | Male | 71 | Yes | Yes | Yes | Yes |
| 216 | Male | 65 | Yes | Yes | Yes | Yes |
| 217 | Male | 68 | Yes | Yes | Yes | Yes |
| 218 | Female | 61 | Yes | No | No | No |
| 219 | Male | 54 | Yes | Yes | No | No |
| 220 | Female | 55 | Yes | No | No | No |
| 221 | Female | 61 | Yes | No | No | No |
| 222 | Male | 53 | Yes | No | No | No |
| 223 | Male | 55 | Yes | No | No | No |
| 224 | Male | 51 | Yes | Yes | Yes | Yes |
| 225 | Male | 51 | Yes | No | No | No |
| 226 | Male | 50 | Yes | Yes | Yes | Yes |
| 227 | Male | 64 | Yes | No | Yes | No |
| 228 | Female | 74 | Yes | No | No | No |
| 229 | Male | 52 | Yes | No | No | No |
| 230 | Male | 63 | Yes | No | No | No |
| 231 | Male | 51 | Yes | Yes | No | No |
| 232 | Male | 67 | Yes | Yes | Yes | Yes |
| 233 | Male | 68 | Yes | Yes | Yes | Yes |
| 234 | Male | 74 | Yes | Yes | No | No |
| 235 | Male | 63 | Yes | No | No | No |
| 236 | Male | 61 | Yes | No | No | No |
| 237 | Female | 69 | Yes | No | No | No |

TABLE 5

Characteristics of the studied subjects

| | Healthy control | Gastric Cancer |
|---|---|---|
| Total Number | 237 | 236 |
| Stage | — | Stage 1 = 71 (30.1%) |
| | | Stage 2 = 36 (15.3%) |
| | | Stage 3 = 54 (22.9%) |
| | | Stage 4 = 75 (31.8%) |
| Subtype | — | Intestinal = 134 (56.8%) |
| | | Diffuse = 70 (29.7%) |
| | | Mixed = 32 (13.6%) |
| Sex (Male) | 150 (63.6%) | 148 (62.7%) |
| Age | 61.2 ± 8.4 | 68.0 ± 10.9 |
| Gastritis | 230 (97.0%) | 200 (84.7%) |
| H Pylori | 132 (55.7%) | 186 (78.8%) |
| Intestinal metaplasia | 121 (51.1%) | 161 (68.2%) |
| Atrophy | 104 (43.9%) | 21 (8.9%) |

It is known that circulating cell-free miRNAs in the blood may be originated from different tissue sources. As a result, the change in the levels of a miRNA caused by the presence of solid gastric tumor can be complicated by the presence of the same miRNA from other sources. Thus, determining the differences in the level of expressions of miRNAs found in cancers and the control group will be challenging and predictably less distinct. In addition, because of the dilution effect of the large volume of blood (5 L in adult human), it is known that most of the cell-free miRNAs are of exceptionally low abundance in blood. Therefore, the accurate measurement of multiple miRNA targets from limited volume of serum/plasma samples is critical and presents a highly significant challenge. To best facilitate the discovery of significantly altered expressions of miRNAs and the identification of multivariate miRNA biomarker panels for the diagnosis of gastric cancer, instead of using low sensitivity or semi-quantitative screening methods (microarray, sequencing), the present Experimental study chose to perform qPCR-based assays with a workflow as summarized in FIG. 2.

In the workflow used in the present Experimental section, all the reactions were performed at least twice in a single-plex manner for miRNA targets and at least four times for synthetic RNA 'spike-in' controls. To ensure the accuracy of the results in such high-throughput qPCR studies, the present study was designed and established, after much iteration, a robust workflow for the discovery of circulating biomarkers (see "Method" section and FIG. 2). In this workflow, various artificially designed 'spike-in' controls were used to monitor and correct for technical variations in isolation, reverse transcription, augmentation and the qPCR processes. All spike-in controls were non-natural synthetic miRNAs mimics (small single-stranded RNA with length range from 22-24 bases), which were designed in silico to have exceptionally low similarity in sequence to all known human miRNAs, thus minimizing cross-hybridization to the primers used in the assays. In addition, the miRNA assays were deliberately divided into a number of multiplex groups in silico to minimize non-specific amplifications and primer-primer interactions. Synthetic miRNAs were used to construct standard curves for the interpolation of absolute copy numbers in all the measurements, thus further correcting for technical variations. Predictably, with this workflow with multiple levels of controls, low levels of expression of miRNAs in circulation could be detected reliably and reproducibly.

MiRNA Biomarkers

A step towards identifying biomarkers is to compare the expression levels of each miRNA in normal (control) and disease state. The expression levels of 578 (miRBase Version 10 release) human miRNAs in all 472 serum samples (gastric cancer and normal/control) were quantitatively measured using the robust workflow and highly sensitive qPCR assays (MiRXES, Singapore).

In the present experimental design, 200 µL of serum was extracted and the total RNA was reversed transcribed and augmented by touch-down amplification to increase the amount of cDNA but yet do not change the representation of the miRNA expression levels (FIG. 2). The augmented cDNA was then diluted for qPCR measurement. A simple calculation based on the effect of dilution revealed that an miRNA, which is expressed at levels ≤500 copies/ml in the serum will be quantified at levels close to the detection limit of the single-plex qPCR assay (≤10 copies/well). At such a concentration, measurements will be a significant challenge due to the technical limitations (errors in pipetting and qPCR). Thus, miRNAs expressed at concentration of ≤500 copies/ml were excluded from analyses and considered undetectable in the present studies.

About 33% of the total miRNAs assayed (578 total miRNA assayed) was found to be highly expressed. These 191 miRNAs were reliably detected in more than 90% of the serum samples (expression levels ≥500 copies/ml; Table 4)

and this was many more than previously reported using other technologies, highlighting the importance of the use of a robust experimental design and well-controlled workflow.

TABLE 4

Sequence of 191 reliable detected mature miRNA

| Name | Sequence | SEQ ID NO: |
|---|---|---|
| hsa-miR-99b-5p | CACCCGUAGAACCGACCUUGCG | 1 |
| hsa-miR-486-5p | UCCUGUACUGAGCUGCCCCGAG | 2 |
| hsa-miR-23b-3p | AUCACAUUGCCAGGGAUUACC | 3 |
| hsa-miR-140-3p | UACCACAGGGUAGAACCACGG | 4 |
| hsa-miR-101-3p | UACAGUACUGUGAUAACUGAA | 5 |
| hsa-miR-107 | AGCAGCAUUGUACAGGGCUAUCA | 6 |
| hsa-miR-130b-3p | CAGUGCAAUGAUGAAAGGGCAU | 7 |
| hsa-miR-369-3p | AAUAAUACAUGGUUGAUCUUU | 8 |
| hsa-miR-133a | UUUGGUCCCCUUCAACCAGCUG | 9 |
| hsa-miR-222-3p | AGCUACAUCUGGCUACUGGGU | 10 |
| hsa-miR-320d | AAAAGCUGGGUUGAGAGGA | 11 |
| hsa-miR-30a-5p | UGUAAACAUCCUCGACUGGAAG | 12 |
| hsa-miR-181a-5p | AACAUUCAACGCUGUCGGUGAGU | 13 |
| hsa-miR-140-5p | CAGUGGUUUUACCCUAUGGUAG | 14 |
| hsa-miR-425-3p | AUCGGGAAUGUCGUGUCCGCCC | 15 |
| hsa-miR-106b-3p | CCGCACUGUGGGUACUUGCUGC | 16 |
| hsa-miR-192-5p | CUGACCUAUGAAUUGACAGCC | 17 |
| hsa-miR-10a-3p | CAAAUUCGUAUCUAGGGGAAUA | 18 |
| hsa-miR-17-5p | CAAAGUGCUUACAGUGCAGGUAG | 19 |
| hsa-miR-590-5p | GAGCUUAUUCAUAAAAGUGCAG | 20 |
| hsa-miR-1299 | UUCUGGAAUUCUGUGUGAGGGA | 21 |
| hsa-miR-365a-3p | UAAUGCCCCUAAAAAUCCUUAU | 22 |
| hsa-miR-500a-5p | UAAUCCUUGCUACCUGGGUGAGA | 23 |
| hsa-miR-32-5p | UAUUGCACAUUACUAAGUUGCA | 24 |
| hsa-miR-340-5p | UUAUAAAGCAAUGAGACUGAUU | 25 |
| hsa-miR-374b-5p | AUAUAAUACAACCUGCUAAGUG | 26 |
| hsa-miR-27a-3p | UUCACAGUGGCUAAGUUCCGC | 27 |
| hsa-miR-627 | GUGAGUCUCUAAGAAAAGAGGA | 28 |
| hsa-miR-539-5p | GGAGAAAUUAUCCUUGGUGUGU | 29 |
| hsa-miR-342-5p | AGGGGUGCUAUCUGUGAUUGA | 30 |
| hsa-miR-484 | UCAGGCUCAGUCCCCUCCCGAU | 31 |
| hsa-miR-132-3p | UAACAGUCUACAGCCAUGGUCG | 32 |
| hsa-miR-379-5p | UGGUAGACUAUGGAACGUAGG | 33 |
| hsa-miR-125a-3p | ACAGGUGAGGUUCUUGGGAGCC | 34 |
| hsa-miR-29a-3p | UAGCACCAUCUGAAAUCGGUUA | 35 |

TABLE 4-continued

Sequence of 191 reliable detected mature miRNA

| Name | Sequence | SEQ ID NO: |
|---|---|---|
| hsa-miR-363-3p | AAUUGCACGGUAUCCAUCUGUA | 36 |
| hsa-miR-376b | AUCAUAGAGGAAAAUCCAUGUU | 37 |
| hsa-miR-589-5p | UGAGAACCACGUCUGCUCUGAG | 38 |
| hsa-miR-432-5p | UCUUGGAGUAGGUCAUUGGGUGG | 39 |
| hsa-miR-1280 | UCCCACCGCUGCCACCC | 40 |
| hsa-miR-103a-3p | AGCAGCAUUGUACAGGGCUAUGA | 41 |
| hsa-miR-122-5p | UGGAGUGUGACAAUGGUGUUUG | 42 |
| hsa-miR-93-5p | CAAAGUGCUGUUCGUGCAGGUAG | 43 |
| hsa-miR-25-3p | CAUUGCACUUGUCUCGGUCUGA | 44 |
| hsa-miR-9-5p | UCUUUGGUUAUCUAGCUGUAUGA | 45 |
| hsa-miR-579 | UUCAUUUGGUAUAAACCGCGAUU | 46 |
| hsa-miR-136-3p | CAUCAUCGUCUCAAAUGAGUCU | 47 |
| hsa-miR-146a-5p | UGAGAACUGAAUUCCAUGGGUU | 48 |
| hsa-miR-144-5p | GGAUAUCAUCAUAUACUGUAAG | 49 |
| hsa-miR-15a-5p | UAGCAGCACAUAAUGGUUUGUG | 50 |
| hsa-miR-150-5p | UCUCCCAACCCUUGUACCAGUG | 51 |
| hsa-miR-152 | UCAGUGCAUGACAGAACUUGG | 52 |
| hsa-miR-29c-5p | UGACCGAUUUCUCCUGGUGUUC | 53 |
| hsa-miR-320c | AAAAGCUGGGUUGAGAGGGU | 54 |
| hsa-miR-127-3p | UCGGAUCCGUCUGAGCUUGGCU | 55 |
| hsa-miR-331-5p | CUAGGUAUGGUCCCAGGGAUCC | 56 |
| hsa-miR-378a-3p | ACUGGACUUGGAGUCAGAAGG | 57 |
| hsa-miR-374a-5p | UUAUAAUACAACCUGAUAAGUG | 58 |
| hsa-miR-409-3p | GAAUGUUGCUCGGUGAACCCCU | 59 |
| hsa-miR-411-3p | UAUGUAACACGGUCCACUAACC | 60 |
| hsa-miR-505-3p | CGUCAACACUUGCUGGUUUCCU | 61 |
| hsa-miR-628-5p | AUGCUGACAUAUUUACUAGAGG | 62 |
| hsa-miR-629-3p | GUUCUCCCAACGUAAGCCCAGC | 63 |
| hsa-miR-4732-3p | GCCCUGACCUGUCCUGUUCUG | 64 |
| hsa-miR-501-5p | AAUCCUUUGUCCCUGGGUGAGA | 65 |
| hsa-miR-616-5p | ACUCAAAACCCUUCAGUGACUU | 66 |
| hsa-miR-454-3p | UAGUGCAAUAUUGCUUAUAGGGU | 67 |
| hsa-miR-485-3p | GUCAUACACGGCUCUCCUCUCU | 68 |
| hsa-miR-133b | UUUGGUCCCCUUCAACCAGCUA | 69 |
| hsa-miR-186-5p | CAAAGAAUUCUCCUUUUGGGCU | 70 |
| hsa-miR-20b-5p | CAAAGUGCUCAUAGUGCAGGUAG | 71 |
| hsa-miR-30d-5p | UGUAAACAUCCCCGACUGGAAG | 72 |
| hsa-miR-375 | UUUGUUCGUUCGGCUCGCGUGA | 73 |

TABLE 4-continued

Sequence of 191 reliable detected mature miRNA

| Name | Sequence | SEQ ID NO: |
|---|---|---|
| hsa-miR-16-5p | UAGCAGCACGUAAAUAUUGGCG | 74 |
| hsa-miR-106b-5p | UAAAGUGCUGACAGUGCAGAU | 75 |
| hsa-miR-139-5p | UCUACAGUGCACGUGUCUCCAG | 76 |
| hsa-miR-141-3p | UAACACUGUCUGGUAAAGAUGG | 77 |
| hsa-miR-185-5p | UGGAGAGAAAGGCAGUUCCUGA | 78 |
| hsa-miR-181b-5p | AACAUUCAUUGCUGUCGGUGGGU | 79 |
| hsa-miR-199a-3p | ACAGUAGUCUGCACAUUGGUUA | 80 |
| hsa-miR-19b-3p | UGUGCAAAUCCAUGCAAAACUGA | 81 |
| hsa-miR-148b-3p | UCAGUGCAUCACAGAACUUUGU | 82 |
| hsa-miR-29b-3p | UAGCACCAUUUGAAAUCAGUGUU | 83 |
| hsa-miR-338-5p | AACAAUAUCCUGGUGCUGAGUG | 84 |
| hsa-miR-584-5p | UUAUGGUUUGCCUGGGACUGAG | 85 |
| hsa-miR-382-5p | GAAGUUGUUCGUGGUGGAUUCG | 86 |
| hsa-miR-151a-3p | CUAGACUGAAGCUCCUUGAGG | 87 |
| hsa-miR-1290 | UGGAUUUUUGGAUCAGGGA | 88 |
| hsa-miR-200b-3p | UAAUACUGCCUGGUAAUGAUGA | 89 |
| hsa-miR-411-5p | UAGUAGACCGUAUAGCGUACG | 90 |
| hsa-miR-126-5p | CAUUAUUACUUUUGGUACGCG | 91 |
| hsa-miR-101-5p | CAGUUAUCACAGUGCUGAUGCU | 92 |
| hsa-miR-125b-5p | UCCCUGAGACCCUAACUUGUGA | 93 |
| hsa-miR-362-5p | AAUCCUUGGAACCUAGGUGUGAGU | 94 |
| hsa-miR-197-3p | UUCACCACCUUCUCCACCCAGC | 95 |
| hsa-miR-221-3p | AGCUACAUUGUCUGCUGGGUUUC | 96 |
| hsa-miR-501-3p | AAUGCACCCGGGCAAGGAUUCU | 97 |
| hsa-miR-671-3p | UCCGGUUCUCAGGGCUCCACC | 98 |
| hsa-miR-181a-2-3p | ACCACUGACCGUUGACUGUACC | 99 |
| hsa-miR-9-3p | AUAAAGCUAGAUAACCGAAAGU | 100 |
| hsa-miR-452-5p | AACUGUUUGCAGAGGAAACUGA | 101 |
| hsa-miR-598 | UACGUCAUCGUUGUCAUCGUCA | 102 |
| hsa-miR-320b | AAAAGCUGGGUUGAGAGGGCAA | 103 |
| hsa-miR-328 | CUGGCCCUCUCUGCCCUUCCGU | 104 |
| hsa-miR-650 | AGGAGGCAGCGCUCUCAGGAC | 105 |
| hsa-miR-134 | UGUGACUGGUUGACCAGAGGGG | 106 |
| hsa-miR-130a-3p | CAGUGCAAUGUUAAAAGGGCAU | 107 |
| hsa-miR-21-5p | UAGCUUAUCAGACUGAUGUUGA | 108 |
| hsa-miR-424-5p | CAGCAGCAAUUCAUGUUUUGAA | 109 |
| hsa-miR-99a-5p | AACCCGUAGAUCCGAUCUUGUG | 110 |
| hsa-miR-18a-3p | ACUGCCCUAAGUGCUCCUUCUGG | 111 |
| hsa-miR-195-5p | UAGCAGCACAGAAAUAUUGGC | 112 |
| hsa-miR-205-5p | UCCUUCAUUCCACCGGAGUCUG | 113 |
| hsa-miR-206 | UGGAAUGUAAGGAAGUGUGUGG | 114 |
| hsa-miR-500a-3p | AUGCACCUGGGCAAGGAUUCUG | 115 |
| hsa-miR-18b-5p | UAAGGUGCAUCUAGUGCAGUUAG | 116 |
| hsa-miR-181d | AACAUUCAUUGUUGUCGGUGGGU | 117 |
| hsa-miR-339-3p | UGAGCGCCUCGACGACAGAGCCG | 118 |
| hsa-miR-93-3p | ACUGCUGAGCUAGCACUUCCCG | 119 |
| hsa-miR-10b-5p | UACCCUGUAGAACCGAAUUUGUG | 120 |
| hsa-miR-497-5p | CAGCAGCACACUGUGGUUUGU | 121 |
| hsa-miR-27b-3p | UUCACAGUGGCUAAGUUCUGC | 122 |
| hsa-miR-128 | UCACAGUGAACCGGUCUCUUU | 123 |
| hsa-miR-183-5p | UAUGGCACUGGUAGAAUUCACU | 124 |
| hsa-miR-22-3p | AAGCUGCCAGUUGAAGAACUGU | 125 |
| hsa-miR-26a-5p | UUCAAGUAAUCCAGGAUAGGCU | 126 |
| hsa-miR-223-3p | UGUCAGUUUGUCAAAUACCCCA | 127 |
| hsa-miR-629-5p | UGGGUUUACGUUGGGAGAACU | 128 |
| hsa-miR-92a-3p | UAUUGCACUUGUCCCGGCCUGU | 129 |
| hsa-miR-29b-2-5p | CUGGUUUCACAUGGUGGCUUAG | 130 |
| hsa-miR-21-3p | CAACACCAGUCGAUGGGCUGU | 131 |
| hsa-miR-199a-5p | CCCAGUGUUCAGACUACCUGUUC | 132 |
| hsa-miR-148a-3p | UCAGUGCACUACAGAACUUUGU | 133 |
| hsa-miR-193a-5p | UGGGUCUUUGCGGGCGAGAUGA | 134 |
| hsa-miR-27a-5p | AGGGCUUAGCUGCUUGUGAGCA | 135 |
| hsa-miR-200c-3p | UAAUACUGCCGGGUAAUGAUGGA | 136 |
| hsa-miR-20a-5p | UAAAGUGCUUAUAGUGCAGGUAG | 137 |
| hsa-miR-194-5p | UGUAACAGCAACUCCAUGUGGA | 138 |
| hsa-miR-532-3p | CCUCCCACACCCAAGGCUUGCA | 139 |
| hsa-miR-19a-3p | UGUGCAAAUCUAUGCAAAACUGA | 140 |
| hsa-miR-142-5p | CAUAAAGUAGAAAGCACUACU | 141 |
| hsa-miR-144-3p | UACAGUAUAGAUGAUGUACU | 142 |
| hsa-miR-145-5p | GUCCAGUUUUCCCAGGAAUCCCU | 143 |
| hsa-miR-10a-5p | UACCCUGUAGAUCCGAAUUUGUG | 144 |
| hsa-miR-23a-3p | AUCACAUUGCCAGGGAUUUCC | 145 |
| hsa-miR-23a-5p | GGGGUUCCUGGGGAUGGGAUUU | 146 |
| hsa-miR-15b-3p | CGAAUCAUUAUUUGCUGCUCUA | 147 |
| hsa-miR-301a-3p | CAGUGCAAUAGUAUUGUCAAAGC | 148 |

TABLE 4-continued

Sequence of 191 reliable detected mature miRNA

| Name | Sequence | SEQ ID NO: |
|---|---|---|
| hsa-miR-660-5p | UACCCAUUGCAUAUCGGAGUUG | 149 |
| hsa-miR-30b-5p | UGUAAACAUCCUACACUCAGCU | 150 |
| hsa-miR-30e-5p | UGUAAACAUCCUUGACUGGAAG | 151 |
| hsa-miR-550a-5p | AGUGCCUGAGGGAGUAAGAGCCC | 152 |
| hsa-miR-425-5p | AAUGACACGAUCACUCCCGUUGA | 153 |
| hsa-miR-4306 | UGGAGAGAAAGGCAGUA | 154 |
| hsa-miR-532-5p | CAUGCCUUGAGUGUAGGACCGU | 155 |
| hsa-miR-335-5p | UCAAGAGCAAUAACGAAAAAUGU | 156 |
| hsa-miR-483-5p | AAGACGGGAGGAAAGAAGGGAG | 157 |
| hsa-miR-1226-3p | UCACCAGCCCUGUGUUCCCUAG | 158 |
| hsa-miR-431-5p | UGUCUUGCAGGCCGUCAUGCA | 159 |
| hsa-miR-324-5p | CGCAUCCCCUAGGGCAUUGGUGU | 160 |
| hsa-miR-487b | AAUCGUACAGGGUCAUCCACUU | 161 |
| hsa-miR-451a | AAACCGUUACCAUUACUGAGUU | 162 |
| hsa-miR-493-5p | UUGUACAUGGUAGGCUUUCAUU | 163 |
| hsa-miR-136-5p | ACUCCAUUUGUUUUGAUGAUGGA | 164 |
| hsa-miR-23c | AUCACAUUGCCAGUGAUUACCC | 165 |
| hsa-miR-95 | UUCAACGGGUAUUUAUUGAGCA | 166 |
| hsa-miR-423-5p | UGAGGGGCAGAGAGCGAGACUUU | 167 |
| hsa-miR-320e | AAAGCUGGGUUGAGAAGG | 168 |
| hsa-miR-224-5p | CAAGUCACUAGUGGUUCCGUU | 169 |
| hsa-miR-28-3p | CACUAGAUUGUGAGCUCCUGGA | 170 |
| hsa-miR-29c-3p | UAGCACCAUUUGAAAUCGGUUA | 171 |
| hsa-miR-326 | CCUCUGGGCCCUUCCUCCAG | 172 |
| hsa-miR-596 | AAGCCUGCCCGGCUCCUCGGG | 173 |
| hsa-miR-885-5p | UCCAUUACACUACCCUGCCUCU | 174 |
| hsa-miR-146b-5p | UGAGAACUGAAUUCCAUAGGCU | 175 |
| hsa-miR-34a-5p | UGGCAGUGUCUUAGCUGGUUGU | 176 |
| hsa-miR-330-3p | GCAAAGCACACGGCCUGCAGAGA | 177 |
| hsa-miR-154-5p | UAGGUUAUCCGUGUUGCCUUCG | 178 |
| hsa-miR-191-5p | CAACGGAAUCCCAAAAGCAGCUG | 179 |
| hsa-miR-193b-3p | AACUGGCCCUCAAAGUCCCGCU | 180 |
| hsa-miR-301b | CAGUGCAAUGAUAUUGUCAAAGC | 181 |
| hsa-miR-30e-3p | CUUUCAGUCGGAUGUUUACAGC | 182 |
| hsa-miR-320a | AAAAGCUGGGUUGAGAGGGCGA | 183 |
| hsa-miR-199b-3p | ACAGUAGUCUGCACAUUGGUUA | 184 |
| hsa-miR-502-3p | AAUGCACCUGGGCAAGGAUUCA | 185 |

TABLE 4-continued

Sequence of 191 reliable detected mature miRNA

| Name | Sequence | SEQ ID NO: |
|---|---|---|
| hsa-miR-450a-5p | UUUUGCGAUGUGUUCCUAAUAU | 186 |
| hsa-miR-495 | AAACAAACAUGGUGCACUUCUU | 187 |
| hsa-miR-126-3p | UCGUACCGUGAGUAAUAAUGCG | 188 |
| hsa-miR-15b-5p | UAGCAGCACAUCAUGGUUUACA | 189 |
| hsa-miR-339-5p | UCCCUGUCCUCCAGGAGCUCACG | 190 |
| hsa-miR-337-5p | GAACGGCUUCAUACAGGAGUU | 191 |

Figure 3:
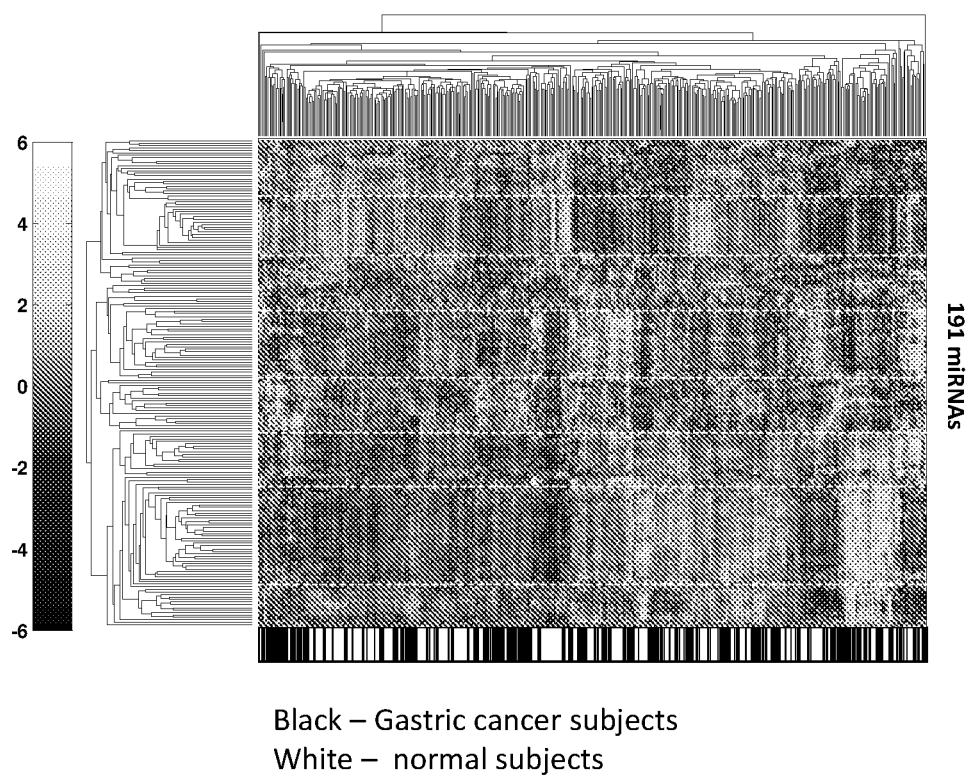
FIG. 3 shows a heat-map of miRNAs consistently detected in samples obtained from subjects.

A heat-map was then constructed to represent the expression levels of all detected serum miRNAs (191 detected miRNAs, FIG. 3). Although various subgroups of miRNAs were clustered together, there did not appear to be clear distinction between the cancer and control groups by unsupervised hierarchical clustering based on total number of detected miRNAs. Thus, without any feature selection, the overall miRNA profiles for both groups appeared similar.

The expressions of the 191 serum miRNAs were then compared

A] Between normal/control and gastric cancer (regardless of stage or subtypes),

B] Between the various stages of the disease (stage 1-4), and

C] Between normal/control and the various stages of the disease.

Significance in differential expressions between two groups were calculated based on the t-test (p-value<0.01) corrected for false discovery rate (FDR) estimation using Bonferroni-type multiple comparison procedures as known in the art.

A] Identification of miRNAs Differentially Expressed in Normal/Control and Gastric Cancer (Regardless of Stage or Subtypes)

Samples from patients clinically confirmed to have either diffuse, intestinal or mixed type of gastric cancers were grouped together and compared to samples from normal/control donors. A pool of 75 miRNAs that showed significant differential expression between control and cancer groups was identified (p-value<0.01; Table 6). Unlike other reports where most of the expression of the putative biomarkers was found to be higher in gastric cancer subjects (Table 1), the present study demonstrated that 51 miRNAs were up-regulated in cancer subjects while 24 were down-regulated (Table 6). Thus, the present experimental design identified of more regulated biomarkers.

TABLE 1

Summary of serum/plasma microRNA biomarkers known in the art for being correlated to gastric cancer

| Up regulated | Down regulated | Method | Samples |
|---|---|---|---|
| miR-199a-3p | — | RT-qPCR | Plasma/80GC/70C |
| — | miR-195-5p | RT-qPCR | Serum/20GC/190C |
| miR-106b, miR-20a, miR-221 | — | RT-qPCR | Plasma/90GC/90C |
| miR-181c | — | RT-qPCR | Plasma/30GC/60C |

TABLE 1-continued

Summary of serum/plasma microRNA biomarkers known
in the art for being correlated to gastric cancer

| Up regulated | Down regulated | Method | Samples |
|---|---|---|---|
| miR-199a-3p, miR-151-5p | — | RT-qPCR | Plasma/180GC/100C |
| miR-221, miR-744, miR-376c, miR-191, miR-27a, let-7e, miR-27b, and miR-222 | — | RT-qPCR | Serum/82GC/82C |
| miR-223, miR-21 | miR-218 | RT-qPCR | Plasma/60GC/60C |
| miR-200c | — | RT-qPCR | whole blood/52GC/15C |
| — | miR-375 | RT-qPCR | Serum |
| miR-370 | — | RT-qPCR | Plasma/33GC/33C |
| miR-17-5p, miR-21, miR-106a, miR-106b | let-7a | RT-qPCR | Plasma/69GC/30C |
| miR-1, miR-20a, miR-27a, miR-34a, miR-423-5p | — | RT-qPCR | Serum/142GC/105C |
| miR-187*, miR-371-5p, miR-378 | — | RT-qPCR | Serum/40GC/41C |

TABLE 6

MiRNAs differentially expressed between
normal/control and gastric cancer

| miRNA name | AUC | P-value | P-value, FDR correction | Fold change |
|---|---|---|---|---|
| Up-regulated | | | | |
| hsa-miR-101-3p | 0.61 | 1.80E−05 | 9.50E−05 | 1.27 |
| hsa-miR-106b-3p | 0.66 | 3.70E−09 | 4.10E−08 | 1.13 |
| hsa-miR-106b-5p | 0.61 | 5.10E−04 | 1.70E−03 | 1.21 |
| hsa-miR-128 | 0.62 | 1.40E−06 | 8.80E−06 | 1.16 |
| hsa-miR-1280 | 0.66 | 3.10E−09 | 3.90E−08 | 1.38 |
| hsa-miR-140-3p | 0.62 | 6.40E−06 | 3.50E−05 | 1.2 |
| hsa-miR-140-5p | 0.67 | 6.20E−10 | 1.20E−08 | 1.24 |
| hsa-miR-142-5p | 0.71 | 1.90E−14 | 3.70E−12 | 1.31 |
| hsa-miR-148a-3p | 0.67 | 2.20E−10 | 4.80E−09 | 1.32 |
| hsa-miR-15b-3p | 0.62 | 6.20E−06 | 3.50E−05 | 1.32 |
| hsa-miR-17-5p | 0.63 | 1.00E−05 | 5.50E−05 | 1.24 |
| hsa-miR-183-5p | 0.64 | 8.80E−07 | 6.20E−06 | 1.53 |
| hsa-miR-186-5p | 0.59 | 1.40E−03 | 3.70E−03 | 1.11 |
| hsa-miR-18b-5p | 0.64 | 1.50E−07 | 1.20E−06 | 1.38 |
| hsa-miR-197-3p | 0.68 | 8.10E−13 | 5.10E−11 | 1.32 |
| hsa-miR-19a-3p | 0.63 | 4.90E−07 | 3.60E−06 | 1.29 |
| hsa-miR-19b-3p | 0.59 | 1.10E−03 | 3.00E−03 | 1.18 |
| hsa-miR-20a-5p | 0.65 | 1.20E−07 | 1.10E−06 | 1.35 |
| hsa-miR-20b-5p | 0.60 | 2.90E−04 | 9.90E−04 | 1.3 |
| hsa-miR-21-3p | 0.60 | 7.90E−05 | 3.20E−04 | 1.13 |
| hsa-miR-21-5p | 0.63 | 2.60E−08 | 2.80E−07 | 1.23 |
| hsa-miR-223-3p | 0.66 | 7.00E−10 | 1.20E−08 | 1.36 |
| hsa-miR-23a-5p | 0.64 | 1.00E−07 | 9.20E−07 | 1.31 |
| hsa-miR-25-3p | 0.62 | 3.40E−05 | 1.60E−04 | 1.26 |
| hsa-miR-27a-5p | 0.69 | 1.00E−13 | 1.00E−11 | 1.76 |
| hsa-miR-29a-3p | 0.61 | 6.00E−05 | 2.60E−04 | 1.17 |
| hsa-miR-29b-2-5p | 0.59 | 4.70E−05 | 2.10E−04 | 1.16 |
| hsa-miR-29b-3p | 0.61 | 7.20E−05 | 3.00E−04 | 1.18 |
| hsa-miR-29c-3p | 0.65 | 2.00E−09 | 2.90E−08 | 1.23 |
| hsa-miR-29c-5p | 0.63 | 1.40E−06 | 8.80E−06 | 1.15 |
| hsa-miR-338-5p | 0.57 | 3.70E−03 | 9.40E−03 | 1.29 |
| hsa-miR-423-5p | 0.60 | 7.20E−05 | 3.00E−04 | 1.18 |
| hsa-miR-424-5p | 0.68 | 7.00E−11 | 1.90E−09 | 1.41 |
| hsa-miR-425-3p | 0.57 | 2.20E−03 | 5.70E−03 | 1.05 |
| hsa-miR-4306 | 0.63 | 1.20E−06 | 8.00E−06 | 1.35 |
| hsa-miR-450a-5p | 0.67 | 2.10E−10 | 4.80E−09 | 1.53 |

TABLE 6-continued

MiRNAs differentially expressed between
normal/control and gastric cancer

| miRNA name | AUC | P-value | P-value, FDR correction | Fold change |
|---|---|---|---|---|
| hsa-miR-486-5p | 0.61 | 9.60E−05 | 3.70E−04 | 1.32 |
| hsa-miR-500a-3p | 0.60 | 1.10E−04 | 4.20E−04 | 1.2 |
| hsa-miR-501-5p | 0.60 | 9.60E−04 | 2.80E−03 | 1.24 |
| hsa-miR-532-3p | 0.60 | 1.90E−04 | 7.00E−04 | 1.15 |
| hsa-miR-550a-5p | 0.63 | 9.00E−07 | 6.20E−06 | 1.38 |
| hsa-miR-579 | 0.62 | 2.20E−05 | 1.10E−04 | 1.3 |
| hsa-miR-589-5p | 0.63 | 1.70E−06 | 1.00E−05 | 1.18 |
| hsa-miR-590-5p | 0.69 | 3.00E−12 | 1.40E−10 | 1.23 |
| hsa-miR-598 | 0.67 | 7.10E−12 | 2.70E−10 | 1.27 |
| hsa-miR-616-5p | 0.65 | 3.40E−09 | 4.10E−08 | 1.35 |
| hsa-miR-627 | 0.58 | 7.30E−04 | 2.30E−03 | 1.19 |
| hsa-miR-629-3p | 0.67 | 6.10E−11 | 1.90E−09 | 1.38 |
| hsa-miR-629-5p | 0.63 | 1.40E−04 | 5.10E−04 | 1.5 |
| hsa-miR-93-3p | 0.62 | 5.10E−06 | 3.00E−05 | 1.22 |
| hsa-miR-93-5p | 0.60 | 2.30E−04 | 8.00E−04 | 1.21 |
| Down-regulated | | | | |
| hsa-miR-107 | 0.65 | 4.40E−08 | 4.40E−07 | 0.8 |
| hsa-miR-122-5p | 0.61 | 8.10E−05 | 3.20E−04 | 0.66 |
| hsa-miR-126-3p | 0.66 | 1.70E−09 | 2.70E−08 | 0.87 |
| hsa-miR-136-5p | 0.61 | 2.30E−05 | 1.10E−04 | 0.72 |
| hsa-miR-139-5p | 0.60 | 8.60E−05 | 3.40E−04 | 0.84 |
| hsa-miR-146a-5p | 0.59 | 2.10E−03 | 5.60E−03 | 0.89 |
| hsa-miR-154-5p | 0.59 | 8.60E−04 | 2.60E−03 | 0.8 |
| hsa-miR-181a-5p | 0.60 | 2.30E−04 | 8.00E−04 | 0.92 |
| hsa-miR-193b-3p | 0.58 | 1.20E−03 | 3.20E−03 | 0.77 |
| hsa-miR-23c | 0.59 | 8.00E−04 | 2.40E−03 | 0.84 |
| hsa-miR-26a-5p | 0.60 | 4.40E−05 | 2.00E−04 | 0.86 |
| hsa-miR-30a-5p | 0.64 | 6.70E−08 | 6.40E−07 | 0.76 |
| hsa-miR-30b-5p | 0.59 | 9.50E−04 | 2.80E−03 | 0.9 |
| hsa-miR-337-5p | 0.63 | 4.80E−07 | 3.60E−06 | 0.74 |
| hsa-miR-339-5p | 0.64 | 4.90E−07 | 3.60E−06 | 0.79 |
| hsa-miR-382-5p | 0.59 | 1.00E−03 | 2.90E−03 | 0.81 |
| hsa-miR-409-3p | 0.59 | 5.00E−04 | 1.60E−03 | 0.77 |
| hsa-miR-411-5p | 0.6 | 7.30E−04 | 2.30E−03 | 0.74 |
| hsa-miR-485-3p | 0.6 | 6.40E−04 | 2.00E−03 | 0.77 |
| hsa-miR-487b | 0.59 | 1.10E−03 | 3.00E−03 | 0.76 |
| hsa-miR-495 | 0.6 | 2.10E−04 | 7.40E−04 | 0.77 |
| hsa-miR-885-5p | 0.62 | 1.90E−05 | 9.60E−05 | 0.69 |
| hsa-miR-99a-5p | 0.58 | 2.90E−03 | 7.50E−03 | 0.82 |
| hsa-miR-99b-5p | 0.67 | 2.60E−09 | 3.50E−08 | 0.78 |

Comparing the results of the present study (Table 6) with the 30 miRNAs identified to be differentially expressed in blood by other reports (Table 1), only six miRNAs (hsa-miR-106b-5p, hsa-miR-17-5p, hsa-miR-20a-5p, hsa-miR-21-5p, hsa-miR-223-3p and hsa-miR-423-5p) were found to be commonly up-regulated (Table 7). Thus, the majority of the purported differentially regulated miRNAs in the literature were not confirmed in the present study. Interestingly, 69 novel miRNAs, which were potential biomarkers for gastric cancers, were identified here.

TABLE 7

Comparison between the current study and other literature reports

| miRNA name in literature | miRBase V18 name | Regulation in literature | Regulation in the current study |
|---|---|---|---|
| let-7e | hsa-let-7e-5p | up | N.D. |
| miR-1 | hsa-miR-1 | up | N.D. |
| miR-106a | hsa-miR-106a-5p | up | N.D. |
| miR-106b | hsa-miR-106b-5p | up | up |
| miR-151-5p | hsa-miR-151a-5p | up | N.D. |
| miR-17-5p | hsa-miR-17-5p | up | up |
| miR-181c | hsa-miR-181c-5p | up | N.D. |
| miR-187* | hsa-miR-187-5p | up | N.D. |
| miR-191 | hsa-miR-191-5p | up | no change |

TABLE 7-continued

Comparison between the current study and other literature reports

| miRNA name in literature | miRBase V18 name | Regulation in literature | Regulation in the current study |
|---|---|---|---|
| miR-199a-3p | hsa-miR-199a-3p | up | no change |
| miR-200c | hsa-miR-200c-3p | up | no change |
| miR-20a | hsa-miR-20a-5p | up | up |
| miR-21 | hsa-miR-21-5p | up | up |
| miR-221 | hsa-miR-221-3p | up | no change |
| miR-222 | hsa-miR-222-3p | up | no change |
| miR-223 | hsa-miR-223-3p | up | up |
| miR-27a | hsa-miR-27a-3p | up | no change |
| miR-27b | hsa-miR-27b-3p | up | no change |
| miR-34a | hsa-miR-34a-5p | up | no change |
| miR-370 | hsa-miR-370 | up | N.D. |
| miR-371-5p | hsa-miR-371a-5p | up | N.D. |
| miR-376c | hsa-miR-376c | up | N.D. |
| miR-378 | hsa-miR-378a-3p | up | no change |
| miR-423-5p | hsa-miR-423-5p | up | up |
| miR-744 | hsa-miR-744-5p | up | N.D. |
| miR-195-5p | hsa-miR-195-5p | down | no change |
| miR-218 | hsa-miR-218-5p | down | N.D. |
| miR-375 | hsa-miR-375 | down | no change |
| let-7a | hsa-let-7a-5p | down | N.D. |

Figure 4:
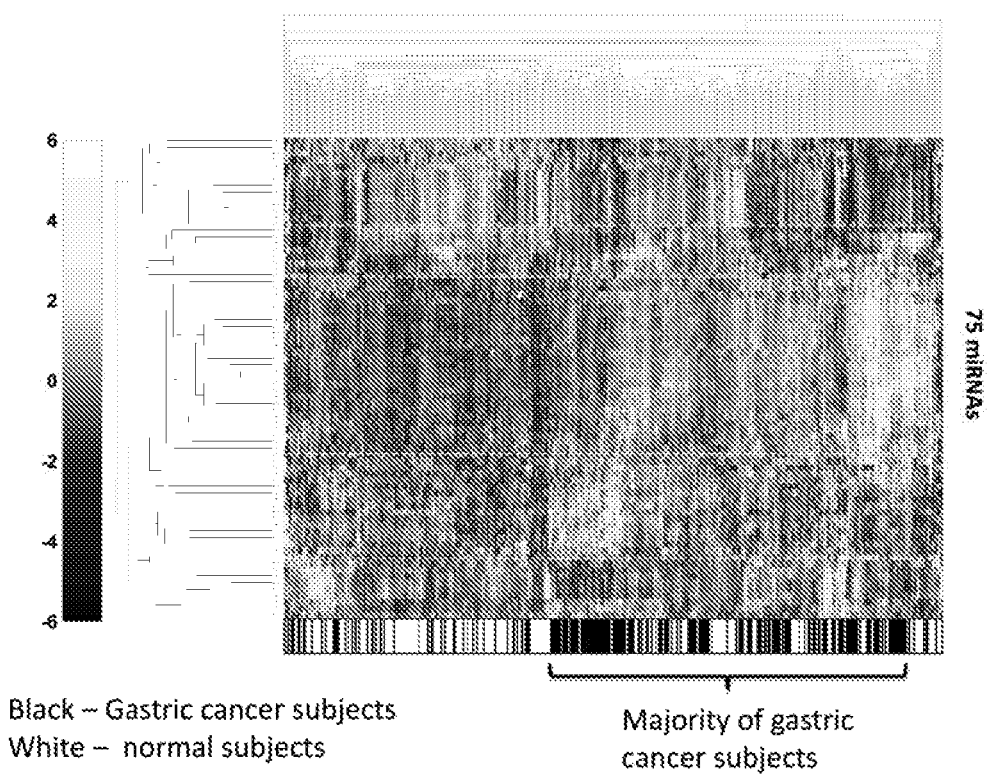
FIG. 4 shows a heat-map of regulated miRNAs. In particular, the heat-map as presented in FIG. 4 represents all of the regulated miRNAs, which are listed in Table 6, in gastric cancer. The expression levels (copy/ml) of miRNAs were presented in log 2 scale and standardized to zero mean. The gray-scale represented the concentrations of miRNA. Hierarchical clustering was carried out for both dimensions (the miRNAs and the samples) based on the Euclidean distance. For the horizon dimensions: black represents gastric cancer subjects and white represents normal/control subjects.
Figure 5:
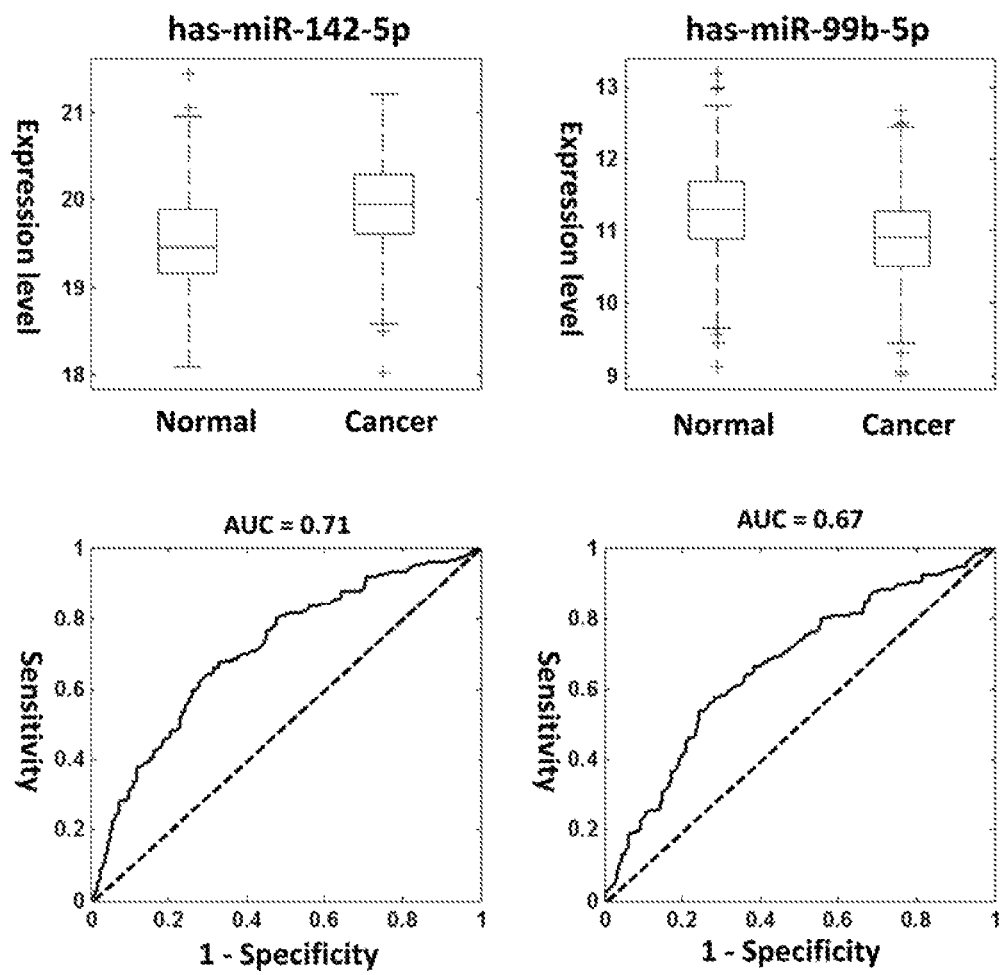
FIG. 5 shows boxplot diagrams representing the expression level of topped ranked up-regulated (hsa-miR-142-5p) and down-regulated miRNAs (hsa-miR-99b-5p) in all gastric cancer subjects (regardless of subtypes and stages) compared to normal/control subjects. Expression levels (copy/ml) are presented in log 2 scale. The boxplot presented miRNA expression levels in subjects that falls in the $25^{th}$, $50^{th}$, and $75^{th}$ percentiles in the distribution of expression levels. AUC refers to area under the receiver operating characteristic curve.

Using this set of 75 biomarkers, a more distinct clustering between gastric cancer and normal/control subjects were observed in the heat-map of the miRNA profile (FIG. 4). Looking at the horizontal dimension, majority of gastric cancer subjects (black) were clustered into a focused area leaving majority of the normal/control subjects to the rest of the space in the map. The AUC values for the topped ranked up-regulated (hsa-miR-142-5p) and down-regulated (hsa-miR-99b-5p) miRNAs were only 0.71 and 0.67, respectively (FIG. 5). Each or the combination of a few of the 75 differentiated miRNAs may serve as biomarker or panels of biomarker (multivariant index assays) for the diagnosis of gastric cancer.

Figure 6:
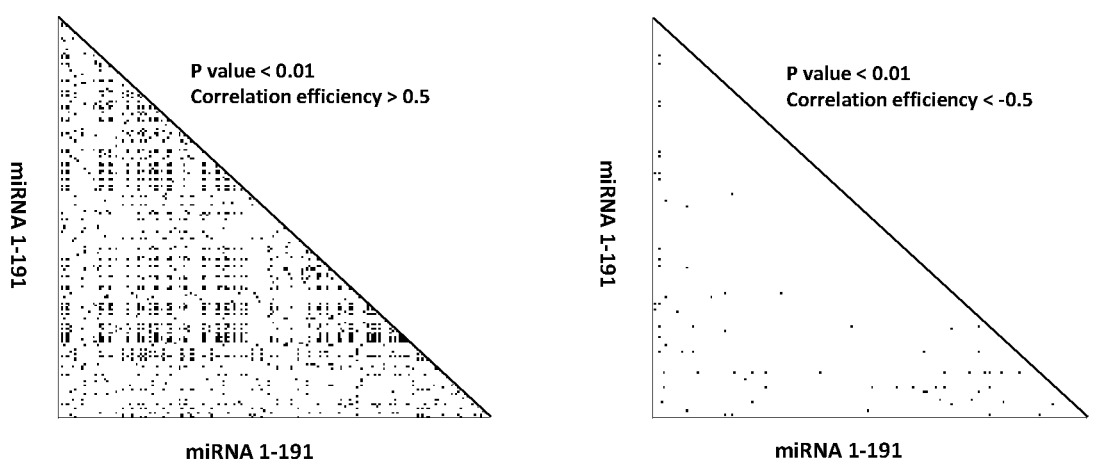
FIG. 6 shows a dot plot showing the results of a correlation analysis between all reliably detected miRNAs. Based on the log 2 scale expression levels (copy/mL), the Pearson's linear correlation efficiencies were calculated between all 191 reliable detected miRNA targets, which are listed in Table 4. Each dot represents a pair of miRNAs where the correlation efficiency is higher than 0.5 (left graph, positively correlated) or low than −0.5 (right graph, negatively correlated) and where the p-value for having a correlation different from zero is lower than 0.01.
Figure 7:
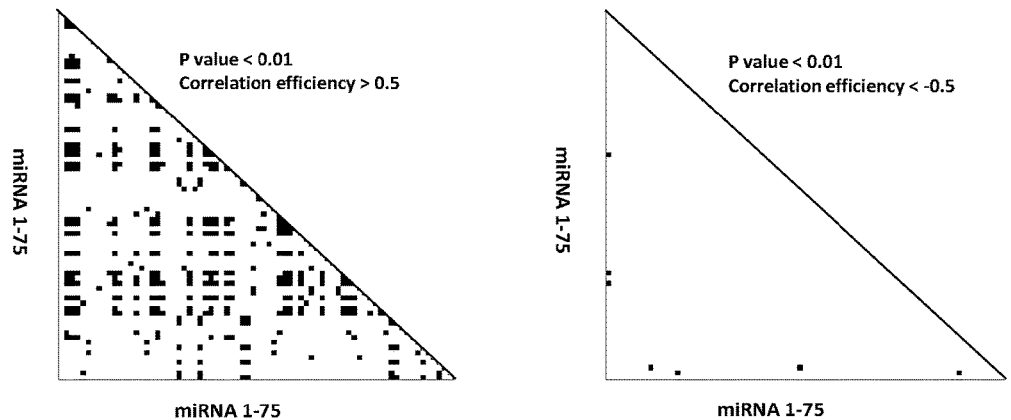
FIG. 7 shows a dot plot showing the results of a correlation analysis gastric cancer biomarkers. Based on the log 2 scale expression levels (copy/mL), the Pearson's linear correlation efficiencies were calculated between all 75 miRNAs altered in gastric cancer subjects, which are listed in Table 6. Each dot represents a pair of miRNAs where the correlation efficiency is higher than 0.5 (left figure, positively correlated) or low than −0.5 (right figure, negatively correlated) and the p-value with a correlation different from zero is lower than 0.01. Thus, taken together.

The expressions of miRNAs were found to cluster into subgroups as illustrated in the heat-maps (FIG. 3, 4). Each cluster has about 10-20 miRNAs (FIG. 3, 4 dashed lines). Analyses of all detectable miRNAs revealed a large number of these as positively correlated (Pearson correlation efficiency>0.5) (FIG. 6). The same observation was also found with the gastric cancer specific miRNAs (FIG. 7). The results demonstrated that certain groups of miRNAs were regulated similarly among all subjects. As a result, a panel of miRNAs could be assembled by substituting one or more distinct miRNAs with another so as to enhance the diagnostic performance and all the 75 significantly altered miRNA were critical for the development of a multivariant index diagnostic assay for gastric cancer.

B] Identification of Differentially Expressed miRNAs Between Normal/Control and Various Stages of Gastric Cancers.

The expressions of miRNAs between the various stages of the disease were then compared. With a two-way Anova test taking account the stages and subtypes, 36 miRNAs (from the pool of 191 serum miRNAs) were found to be differentially expressed between various stages of gastric cancer subjects (p-value of anova test<0.01 after false discovery rate correction, data not shown).

Knowing the difference between the various stages, the next attempt was made to identify differentially expressed miRNA between each stage of cancer and normal/control. The total number of distinct miRNAs found in this new search process was 113 (Tables 8-11, where the profiles overlapped). Among these, a pool of 20 (8 Up-regulated and 12 Down-regulated), 62 (54 Up-regulated and 8 Down-regulated), 43 (37 Up-regulated and 6 Down-regulated) or 74 (28 Up-regulated and 46 Down-regulated) miRNAs showed differential expression between normal/control and the corresponding stages of 1, 2, 3 and 4, respectively (p-value after FDR correction<0.01, Tables 8-11).

TABLE 8

MiRNAs differentially expressed between normal/control and stage 1 gastric cancer

| miRNA name | AUC | P-value | P-value, FDR correction | Fold change |
|---|---|---|---|---|
| Up-regulated, N = 8 | | | | |
| hsa-miR-27a-5p | 0.66 | 5.4E−05 | 1.7E−03 | 1.57 |
| hsa-miR-101-3p | 0.63 | 8.0E−04 | 9.8E−03 | 1.31 |
| hsa-miR-29c-3p | 0.66 | 4.9E−05 | 1.7E−03 | 1.22 |
| hsa-miR-29b-3p | 0.63 | 1.0E−03 | 9.8E−03 | 1.21 |
| hsa-miR-142-5p | 0.67 | 1.7E−04 | 4.7E−03 | 1.21 |
| hsa-miR-590-5p | 0.65 | 3.2E−04 | 7.6E−03 | 1.16 |
| hsa-miR-21-3p | 0.63 | 4.0E−04 | 7.7E−03 | 1.16 |
| hsa-miR-106b-3p | 0.64 | 6.8E−04 | 9.8E−03 | 1.11 |
| Down-regulated, N = 12 | | | | |
| hsa-miR-146a-5p | 0.65 | 1.0E−03 | 9.8E−03 | 0.84 |
| hsa-miR-15b-5p | 0.63 | 4.0E−04 | 7.7E−03 | 0.82 |
| hsa-miR-103a-3p | 0.65 | 5.1E−04 | 8.9E−03 | 0.82 |
| hsa-miR-26a-5p | 0.67 | 1.3E−05 | 8.5E−04 | 0.79 |
| hsa-miR-362-5p | 0.63 | 6.0E−04 | 9.6E−03 | 0.78 |
| hsa-miR-671-3p | 0.68 | 8.7E−04 | 9.8E−03 | 0.78 |
| hsa-miR-454-3p | 0.62 | 9.5E−04 | 9.8E−03 | 0.77 |
| hsa-miR-328 | 0.67 | 5.4E−05 | 1.7E−03 | 0.74 |
| hsa-miR-221-3p | 0.69 | 3.5E−07 | 6.8E−05 | 0.74 |
| hsa-miR-23c | 0.69 | 2.3E−06 | 2.2E−04 | 0.70 |
| hsa-miR-136-5p | 0.63 | 9.8E−04 | 9.8E−03 | 0.68 |
| hsa-miR-485-3p | 0.64 | 9.7E−04 | 9.8E−03 | 0.68 |

TABLE 9

MiRNAs differentially expressed between normal/control and stage 2 gastric cancer

| miRNA name | AUC | P-value | P-value, FDR correction | Fold change |
|---|---|---|---|---|
| Up-regulated, N = 54 | | | | |
| hsa-miR-27a-5p | 0.76 | 5.6E−07 | 1.2E−05 | 2.13 |
| hsa-miR-183-5p | 0.72 | 7.4E−05 | 5.9E−04 | 1.99 |
| hsa-miR-629-5p | 0.72 | 7.7E−04 | 3.3E−03 | 1.99 |
| hsa-miR-424-5p | 0.79 | 2.4E−08 | 1.2E−06 | 1.76 |
| hsa-miR-1280 | 0.74 | 3.4E−07 | 9.2E−06 | 1.74 |
| hsa-miR-18b-5p | 0.74 | 3.6E−06 | 5.3E−05 | 1.74 |
| hsa-miR-195-5p | 0.73 | 1.9E−06 | 3.0E−05 | 1.70 |
| hsa-miR-18a-3p | 0.73 | 1.9E−05 | 2.1E−04 | 1.68 |
| hsa-miR-550a-5p | 0.72 | 8.6E−05 | 6.6E−04 | 1.67 |
| hsa-miR-197-3p | 0.81 | 1.4E−11 | 1.7E−09 | 1.63 |
| hsa-miR-20a-5p | 0.74 | 1.7E−05 | 1.9E−04 | 1.61 |
| hsa-miR-363-3p | 0.68 | 1.2E−03 | 4.5E−03 | 1.60 |
| hsa-miR-450a-5p | 0.69 | 4.3E−04 | 2.2E−03 | 1.60 |
| hsa-miR-20b-5p | 0.67 | 1.2E−03 | 4.7E−03 | 1.58 |
| hsa-miR-15b-5p | 0.71 | 1.7E−04 | 1.2E−03 | 1.58 |
| hsa-miR-142-5p | 0.82 | 1.8E−11 | 1.7E−09 | 1.57 |
| hsa-miR-93-5p | 0.73 | 2.2E−05 | 2.1E−04 | 1.55 |
| hsa-miR-501-5p | 0.70 | 1.0E−03 | 4.2E−03 | 1.54 |
| hsa-miR-4306 | 0.70 | 2.9E−04 | 1.6E−03 | 1.53 |
| hsa-miR-181a-2-3p | 0.70 | 1.6E−04 | 1.1E−03 | 1.53 |
| hsa-miR-16-5p | 0.67 | 1.1E−03 | 4.2E−03 | 1.53 |
| hsa-miR-128 | 0.82 | 5.9E−11 | 3.8E−09 | 1.49 |
| hsa-miR-500a-3p | 0.73 | 1.1E−05 | 1.3E−04 | 1.48 |
| hsa-miR-223-3p | 0.71 | 2.2E−05 | 2.1E−04 | 1.47 |
| hsa-miR-501-3p | 0.68 | 3.6E−04 | 1.9E−03 | 1.47 |
| hsa-miR-19a-3p | 0.72 | 6.9E−05 | 5.8E−04 | 1.46 |
| hsa-miR-629-3p | 0.70 | 5.8E−05 | 5.2E−04 | 1.46 |
| hsa-miR-25-3p | 0.69 | 7.0E−04 | 3.1E−03 | 1.46 |

TABLE 9-continued

MiRNAs differentially expressed between normal/control and stage 2 gastric cancer

| miRNA name | AUC | P-value | P-value, FDR correction | Fold change |
|---|---|---|---|---|
| hsa-miR-140-5p | 0.79 | 3.7E−08 | 1.4E−06 | 1.43 |
| hsa-miR-29a-3p | 0.73 | 1.1E−05 | 1.3E−04 | 1.42 |
| hsa-miR-23a-5p | 0.65 | 2.2E−04 | 1.3E−03 | 1.41 |
| hsa-miR-148a-3p | 0.73 | 6.6E−05 | 5.7E−04 | 1.40 |
| hsa-miR-598 | 0.76 | 4.9E−07 | 1.2E−05 | 1.38 |
| hsa-miR-17-5p | 0.71 | 4.4E−04 | 2.2E−03 | 1.38 |
| hsa-miR-106b-5p | 0.68 | 2.0E−03 | 6.5E−03 | 1.38 |
| hsa-miR-186-5p | 0.76 | 2.1E−07 | 6.7E−06 | 1.36 |
| hsa-miR-93-3p | 0.71 | 2.8E−04 | 1.6E−03 | 1.35 |
| hsa-miR-23a-3p | 0.72 | 1.7E−06 | 3.0E−05 | 1.34 |
| hsa-miR-339-3p | 0.65 | 1.9E−03 | 6.4E−03 | 1.33 |
| hsa-miR-15a-5p | 0.69 | 1.7E−03 | 6.0E−03 | 1.33 |
| hsa-miR-29b-3p | 0.70 | 1.9E−04 | 1.2E−03 | 1.33 |
| hsa-miR-140-3p | 0.68 | 4.7E−04 | 2.3E−03 | 1.33 |
| hsa-miR-29c-5p | 0.75 | 1.7E−06 | 3.0E−05 | 1.32 |
| hsa-miR-320b | 0.68 | 2.5E−03 | 8.0E−03 | 1.32 |
| hsa-miR-423-5p | 0.70 | 2.0E−04 | 1.2E−03 | 1.31 |
| hsa-miR-15b-5p | 0.69 | 6.3E−04 | 2.9E−03 | 1.27 |
| hsa-miR-221-3p | 0.68 | 1.9E−03 | 6.4E−03 | 1.27 |
| hsa-miR-29b-2-5p | 0.67 | 8.6E−04 | 3.7E−03 | 1.26 |
| hsa-miR-532-3p | 0.66 | 2.6E−03 | 8.2E−03 | 1.26 |
| hsa-miR-374b-5p | 0.67 | 4.9E−04 | 2.3E−03 | 1.25 |
| hsa-miR-29c-3p | 0.68 | 1.3E−03 | 4.9E−03 | 1.24 |
| hsa-miR-21-5p | 0.66 | 2.7E−03 | 8.5E−03 | 1.23 |
| hsa-miR-589-5p | 0.69 | 2.0E−03 | 6.7E−03 | 1.23 |
| hsa-miR-106b-3p | 0.67 | 1.6E−03 | 5.9E−03 | 1.13 |
| Down-regulated, N = 8 | | | | |
| hsa-miR-126-3p | 0.68 | 3.7E−04 | 1.9E−03 | 0.87 |
| hsa-miR-107 | 0.65 | 3.1E−03 | 9.5E−03 | 0.80 |
| hsa-miR-320a | 0.67 | 1.3E−03 | 4.9E−03 | 0.77 |
| hsa-miR-339-5p | 0.71 | 1.2E−04 | 9.1E−04 | 0.70 |
| hsa-miR-337-5p | 0.68 | 9.4E−04 | 3.9E−03 | 0.70 |
| hsa-miR-99b-5p | 0.74 | 7.0E−06 | 9.5E−05 | 0.69 |
| hsa-miR-193b-3p | 0.69 | 5.6E−04 | 2.6E−03 | 0.58 |
| hsa-miR-885-5p | 0.71 | 2.0E−04 | 1.2E−03 | 0.56 |

TABLE 10

MiRNAs differentially expressed between normal/control and stage 3 gastric cancer

| miRNA name | AUC | P-value | P-value, FDR correction | Fold change |
|---|---|---|---|---|
| Up-regulated, N = 37 | | | | |
| hsa-miR-629-5p | 0.70 | 1.7E−04 | 1.3E−03 | 1.93 |
| hsa-miR-650 | 0.66 | 3.1E−05 | 3.3E−04 | 1.79 |
| hsa-miR-1280 | 0.75 | 5.4E−09 | 2.6E−07 | 1.67 |
| hsa-miR-27a-5p | 0.68 | 3.7E−05 | 3.5E−04 | 1.67 |
| hsa-miR-18b-5p | 0.70 | 1.3E−06 | 2.4E−05 | 1.66 |
| hsa-miR-424-5p | 0.72 | 1.1E−07 | 3.0E−06 | 1.60 |
| hsa-miR-21-5p | 0.78 | 1.7E−12 | 3.3E−10 | 1.57 |
| hsa-miR-500a-3p | 0.69 | 3.6E−08 | 1.1E−06 | 1.55 |
| hsa-miR-629-3p | 0.71 | 3.6E−07 | 8.7E−06 | 1.50 |
| hsa-miR-223-3p | 0.70 | 7.6E−07 | 1.6E−05 | 1.49 |
| hsa-miR-550a-5p | 0.65 | 4.9E−04 | 3.0E−03 | 1.48 |
| hsa-miR-4306 | 0.65 | 2.1E−04 | 1.5E−03 | 1.46 |
| hsa-miR-197-3p | 0.73 | 1.2E−09 | 7.7E−08 | 1.45 |
| hsa-miR-616-5p | 0.68 | 5.7E−06 | 7.2E−05 | 1.44 |
| hsa-miR-128 | 0.77 | 1.2E−11 | 1.1E−09 | 1.43 |
| hsa-miR-450a-5p | 0.63 | 1.4E−03 | 7.1E−03 | 1.42 |
| hsa-miR-148a-3p | 0.70 | 3.4E−06 | 5.2E−05 | 1.39 |
| hsa-miR-598 | 0.74 | 7.9E−09 | 3.0E−07 | 1.38 |
| hsa-miR-15b-3p | 0.66 | 1.4E−03 | 6.9E−03 | 1.38 |
| hsa-miR-423-5p | 0.66 | 2.3E−06 | 3.9E−05 | 1.37 |
| hsa-miR-1290 | 0.63 | 1.7E−03 | 7.7E−03 | 1.36 |
| hsa-miR-93-3p | 0.65 | 5.3E−05 | 4.8E−04 | 1.36 |
| hsa-miR-22-3p | 0.64 | 7.8E−05 | 6.5E−04 | 1.34 |
| hsa-miR-23a-5p | 0.65 | 2.6E−04 | 1.8E−03 | 1.32 |

TABLE 10-continued

MiRNAs differentially expressed between normal/control and stage 3 gastric cancer

| miRNA name | AUC | P-value | P-value, FDR correction | Fold change |
|---|---|---|---|---|
| hsa-miR-320c | 0.63 | 6.3E−04 | 3.7E−03 | 1.31 |
| hsa-miR-130a-3p | 0.66 | 1.4E−05 | 1.6E−04 | 1.31 |
| hsa-miR-320b | 0.62 | 8.9E−04 | 4.7E−03 | 1.31 |
| hsa-miR-320e | 0.63 | 8.8E−04 | 4.7E−03 | 1.31 |
| hsa-miR-19a-3p | 0.64 | 1.5E−03 | 7.1E−03 | 1.30 |
| hsa-miR-378a-3p | 0.63 | 4.9E−04 | 3.0E−03 | 1.28 |
| hsa-miR-9-5p | 0.62 | 2.0E−03 | 8.9E−03 | 1.27 |
| hsa-miR-29b-2-5p | 0.64 | 1.6E−04 | 1.3E−03 | 1.27 |
| hsa-miR-532-3p | 0.64 | 6.7E−04 | 3.9E−03 | 1.25 |
| hsa-miR-590-5p | 0.69 | 6.8E−06 | 8.2E−05 | 1.24 |
| hsa-miR-589-5p | 0.62 | 9.5E−04 | 4.9E−03 | 1.20 |
| hsa-miR-140-5p | 0.65 | 8.9E−04 | 4.7E−03 | 1.20 |
| hsa-miR-29c-5p | 0.67 | 2.3E−04 | 1.6E−03 | 1.20 |
| Down-regulated, N = 6 | | | | |
| hsa-miR-126-5p | 0.60 | 2.1E−03 | 9.5E−03 | 0.88 |
| hsa-miR-126-3p | 0.63 | 3.2E−04 | 2.1E−03 | 0.88 |
| hsa-miR-27a-3p | 0.64 | 3.9E−06 | 5.3E−05 | 0.78 |
| hsa-miR-99b-5p | 0.68 | 3.5E−05 | 3.5E−04 | 0.75 |
| hsa-miR-107 | 0.68 | 3.6E−06 | 5.2E−05 | 0.74 |
| hsa-miR-30a-5p | 0.67 | 6.9E−05 | 6.0E−04 | 0.72 |

TABLE 11

MiRNAs differentially expressed between normal/control and stage 4 gastric cancer

| miRNA name | AUC | P-value | P-value, FDR correction | Fold change |
|---|---|---|---|---|
| Up-regulated, N = 46 | | | | |
| hsa-miR-27a-5p | 0.70 | 7.5E−08 | 1.0E−06 | 1.86 |
| hsa-miR-338-5p | 0.70 | 2.0E−06 | 1.7E−05 | 1.86 |
| hsa-miR-450a-5p | 0.73 | 9.2E−09 | 1.8E−07 | 1.80 |
| hsa-miR-183-5p | 0.66 | 1.2E−04 | 6.3E−04 | 1.62 |
| hsa-miR-579 | 0.69 | 5.6E−07 | 6.0E−06 | 1.59 |
| hsa-miR-616-5p | 0.71 | 5.0E−10 | 2.4E−08 | 1.55 |
| hsa-miR-424-5p | 0.72 | 1.0E−08 | 1.8E−07 | 1.52 |
| hsa-miR-200b-3p | 0.61 | 1.5E−04 | 7.0E−04 | 1.48 |
| hsa-miR-148a-3p | 0.74 | 7.7E−10 | 2.9E−08 | 1.48 |
| hsa-miR-223-3p | 0.68 | 2.5E−07 | 3.0E−06 | 1.46 |
| hsa-miR-142-5p | 0.77 | 1.1E−12 | 2.1E−10 | 1.43 |
| hsa-miR-629-3p | 0.67 | 9.4E−07 | 8.5E−06 | 1.42 |
| hsa-miR-4306 | 0.63 | 1.5E−04 | 7.0E−04 | 1.40 |
| hsa-miR-15b-3p | 0.64 | 2.6E−04 | 1.1E−03 | 1.40 |
| hsa-miR-20a-5p | 0.65 | 7.0E−05 | 4.2E−04 | 1.40 |
| hsa-miR-627 | 0.67 | 1.1E−05 | 7.8E−05 | 1.37 |
| hsa-miR-20b-5p | 0.61 | 2.7E−03 | 7.4E−03 | 1.37 |
| hsa-miR-1280 | 0.71 | 5.4E−09 | 1.2E−07 | 1.37 |
| hsa-miR-197-3p | 0.71 | 5.4E−09 | 1.2E−07 | 1.37 |
| hsa-miR-101-3p | 0.64 | 1.3E−04 | 6.3E−04 | 1.36 |
| hsa-miR-598 | 0.71 | 1.9E−09 | 5.2E−08 | 1.36 |
| hsa-miR-23a-5p | 0.65 | 1.4E−05 | 9.3E−05 | 1.36 |
| hsa-miR-141-3p | 0.57 | 1.3E−03 | 4.3E−03 | 1.34 |
| hsa-miR-19a-3p | 0.64 | 9.0E−05 | 5.1E−04 | 1.34 |
| hsa-miR-550a-5p | 0.62 | 2.8E−03 | 7.6E−03 | 1.33 |
| hsa-miR-140-5p | 0.70 | 4.2E−08 | 6.7E−07 | 1.33 |
| hsa-miR-29c-3p | 0.69 | 5.2E−08 | 7.6E−07 | 1.32 |
| hsa-miR-18b-5p | 0.62 | 2.3E−03 | 6.5E−03 | 1.31 |
| hsa-miR-590-5p | 0.73 | 4.1E−10 | 2.4E−08 | 1.31 |
| hsa-miR-106b-5p | 0.63 | 9.5E−04 | 3.3E−03 | 1.31 |
| hsa-miR-1280 | 0.64 | 6.8E−04 | 2.6E−03 | 1.29 |
| hsa-miR-191-5p | 0.60 | 2.1E−03 | 6.1E−03 | 1.27 |
| hsa-miR-589-5p | 0.69 | 8.4E−07 | 8.0E−06 | 1.27 |
| hsa-miR-140-3p | 0.64 | 1.3E−04 | 6.3E−04 | 1.26 |
| hsa-miR-93-5p | 0.62 | 2.0E−03 | 5.9E−03 | 1.26 |
| hsa-miR-17-5p | 0.63 | 1.4E−03 | 4.5E−03 | 1.25 |
| hsa-miR-29b-3p | 0.62 | 2.5E−04 | 1.1E−03 | 1.25 |
| hsa-miR-628-5p | 0.62 | 3.5E−03 | 9.0E−03 | 1.23 |
| hsa-miR-93-3p | 0.63 | 7.5E−04 | 2.7E−03 | 1.23 |
| hsa-miR-21-5p | 0.63 | 8.3E−05 | 4.8E−04 | 1.23 |

TABLE 11-continued

MiRNAs differentially expressed between normal/control and stage 4 gastric cancer

| miRNA name | AUC | P-value | P-value, FDR correction | Fold change |
|---|---|---|---|---|
| hsa-miR-106b-3p | 0.71 | 2.2E-09 | 5.2E-08 | 1.21 |
| hsa-miR-484 | 0.63 | 1.7E-03 | 5.3E-03 | 1.20 |
| hsa-miR-29a-3p | 0.62 | 2.1E-03 | 6.1E-03 | 1.19 |
| hsa-miR-29b-2-5p | 0.61 | 1.5E-03 | 4.6E-03 | 1.18 |
| hsa-miR-29c-5p | 0.65 | 2.2E-04 | 9.6E-04 | 1.17 |
| hsa-miR-425-5p | 0.62 | 2.2E-03 | 6.3E-03 | 1.15 |
| hsa-miR-425-3p | 0.65 | 2.2E-06 | 1.8E-05 | 1.12 |
| Down-regulated, N = 28 | | | | |
| hsa-miR-181a-5p | 0.61 | 1.3E-03 | 4.4E-03 | 0.90 |
| hsa-miR-30d-5p | 0.62 | 5.7E-04 | 2.2E-03 | 0.88 |
| hsa-miR-30b-5p | 0.62 | 1.2E-03 | 4.1E-03 | 0.85 |
| hsa-miR-126-3p | 0.72 | 2.2E-10 | 2.1E-08 | 0.82 |
| hsa-miR-146a-5p | 0.66 | 1.2E-04 | 6.3E-04 | 0.81 |
| hsa-miR-107 | 0.64 | 2.1E-04 | 9.5E-04 | 0.81 |
| hsa-miR-99b-5p | 0.65 | 9.4E-05 | 5.1E-04 | 0.78 |
| hsa-miR-10a-5p | 0.66 | 3.9E-04 | 1.6E-03 | 0.77 |
| hsa-miR-139-5p | 0.66 | 2.1E-05 | 1.3E-04 | 0.77 |
| hsa-miR-10b-5p | 0.62 | 2.8E-03 | 7.6E-03 | 0.77 |
| hsa-miR-23c | 0.65 | 1.6E-04 | 7.2E-04 | 0.76 |
| hsa-miR-497-5p | 0.65 | 7.1E-04 | 2.6E-03 | 0.76 |
| hsa-miR-154-5p | 0.62 | 3.3E-03 | 8.7E-03 | 0.75 |
| hsa-miR-26a-5p | 0.68 | 1.0E-07 | 1.3E-06 | 0.74 |
| hsa-miR-339-5p | 0.67 | 1.7E-05 | 1.1E-04 | 0.74 |
| hsa-miR-382-5p | 0.64 | 7.2E-04 | 2.6E-03 | 0.73 |
| hsa-miR-134 | 0.63 | 7.4E-04 | 2.7E-03 | 0.72 |
| hsa-miR-409-3p | 0.63 | 1.1E-03 | 3.8E-03 | 0.70 |
| hsa-miR-487b | 0.62 | 3.3E-03 | 8.7E-03 | 0.69 |
| hsa-miR-136-5p | 0.62 | 1.5E-03 | 4.6E-03 | 0.69 |
| hsa-miR-150-5p | 0.66 | 1.8E-06 | 1.6E-05 | 0.67 |
| hsa-miR-193b-3p | 0.64 | 4.9E-04 | 2.0E-03 | 0.66 |
| hsa-miR-30a-5p | 0.72 | 2.0E-09 | 5.2E-08 | 0.65 |
| hsa-miR-99a-5p | 0.67 | 8.1E-06 | 6.0E-05 | 0.65 |
| hsa-miR-337-5p | 0.69 | 2.9E-07 | 3.2E-06 | 0.64 |
| hsa-miR-495 | 0.67 | 7.1E-06 | 5.4E-05 | 0.63 |
| hsa-miR-885-5p | 0.66 | 2.5E-05 | 1.5E-04 | 0.59 |
| hsa-miR-122-5p | 0.69 | 7.5E-07 | 7.5E-06 | 0.48 |

With the exception of three miRNAs (hsa-miR-486-5p, hsa-miR-19b-3p, hsa-miR-411-5p), the rest of the 75 miRNAs discovered from analysis using all stages of cancer collectively (Table 6) were found to be a subset of these 113 miRNAs identified when analyzing each stage of the cancer independently. Most of the 36 miRNAs (except one) found differentially regulated between various stages of gastric cancers were also found to be differentially expressed when comparing normal/control (N) and each stage (S1-S4) of gastric cancer (Tables 8-11). The differences between the stages resulted different pools of miRNAs to be useful for the detection of gastric cancer. Hence, the results from comparing expression levels in the different stages against normal/control resulted in a larger pool of informative miRNAs.

Figure 8:
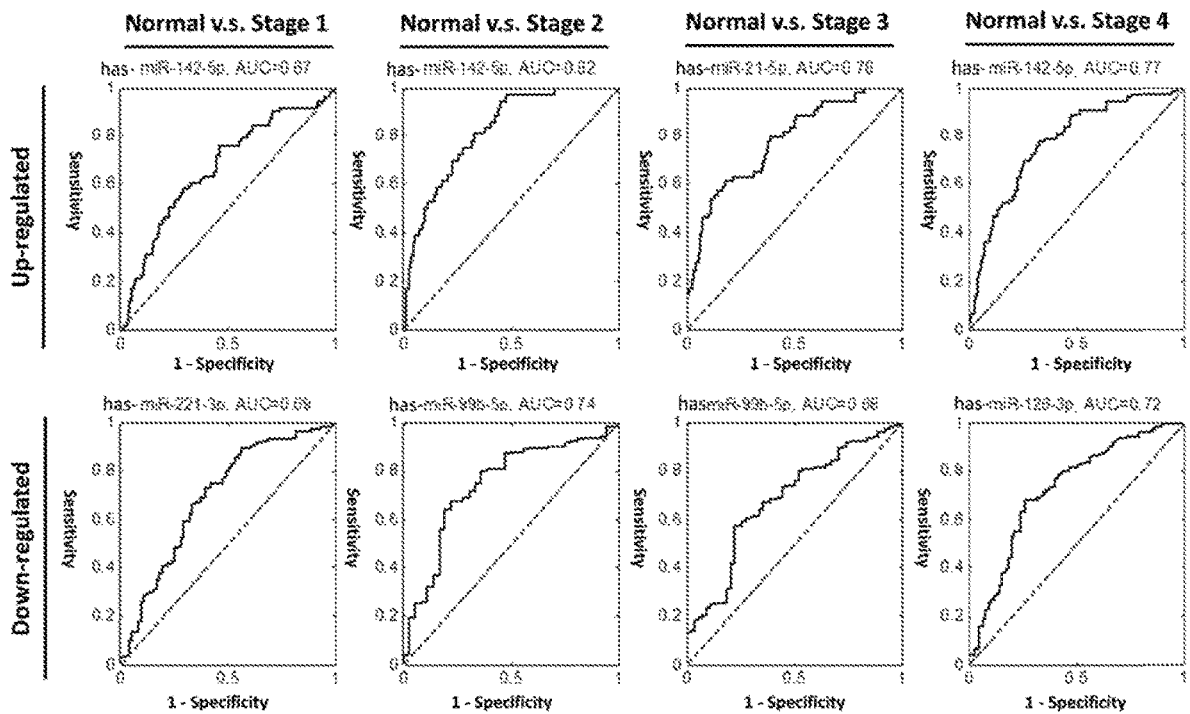
FIG. 8 shows graphs plotting the sensitivity and specificity of various top rated miRNAs in the various stages of gastric cancer as compared to normal/control. More specifically.
Figure 10:
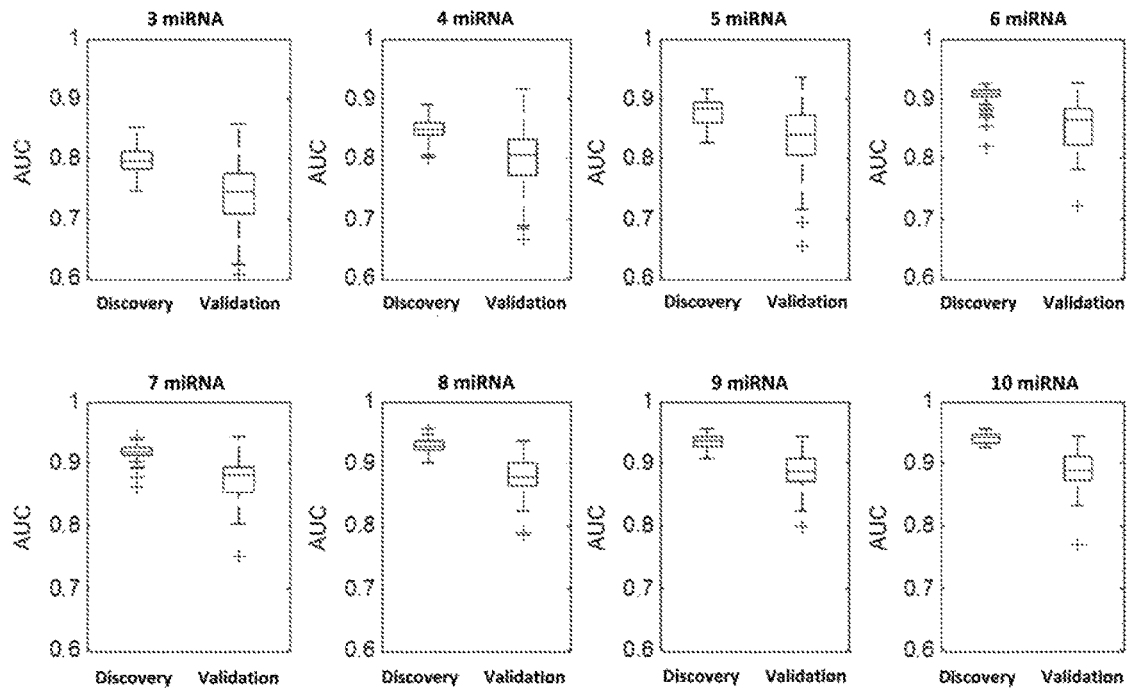
FIG. 10 shows boxplots of diagnostic power (AUC) of multivariant biomarker panels (number of miRNAs is 3 to 10) in the discovery and validation phases during the four fold cross validation in silico. The biomarker panels with 3 to 10 miRNAs were identified with the sequence forward floating search using linear support vector machine as the model based on the discovery set of samples and validated in another independent set of samples. Multiple times of four fold cross validation were carried out. The boxplot presented the 25th, 50th, and 75th percentiles of miRNA sets in the AUC for the classification of normal/control and gastric cancer subjects.

Clearly, lesser number of miRNAs was identified in early stage 1 than in later stages. The identity of the miRNAs which were ranked highest in AUC values were not always the same for all stages (FIG. 8). Large numbers of miRNAs were regulated (Table 8-11) and similar identities were repeatedly found across the stages (FIG. 10). Only one miRNA (hsa-miR-27a-5p) was found to be common among all four stages. These distinct miRNAs (Tables 8-11) can be used individually and the collective results of multiple miRNAs may be useful for the diagnosis of gastric cancers in a clinical setting where the stage of the cancer is unknown at point of presentation.

From the study above, a biomarker panel consisting of at least one miRNA from the each stage specific miRNA list could provide an alternative method for determining the likelihood of a subject having gastric cancer.

III, Search for Multivariant Biomarker Panels

Figure 9:
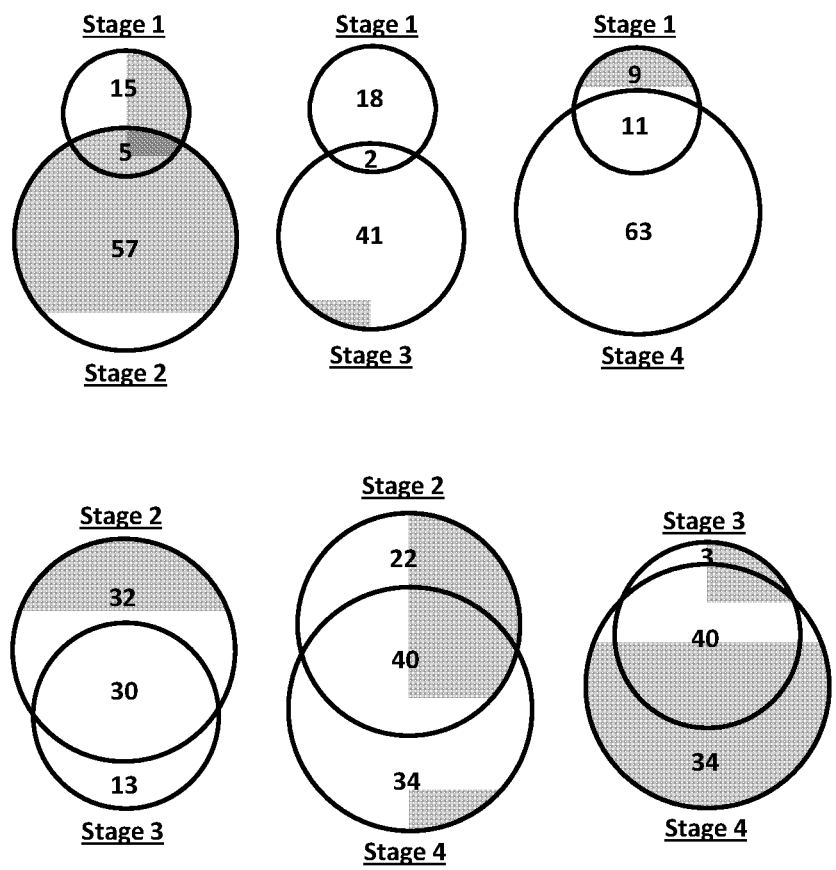
FIG. 9 shows Venn diagrams illustrating the overlaps between the biomarkers for various stages of gastric cancers. These Venn diagrams are generated based on Tables 8, 9, 10 and 11. Thus.

An important criterion to assemble a multivariate panel is to include at least one miRNA from the specific list for each stage of cancer to ensure all cancer subgroups were covered. However, the miRNAs defining the four stages of cancer were not totally distinct as the same miRNAs were similarly found between them (FIG. 9). At the same time, large numbers of cancer related or non-related miRNAs were found to be positively correlated (FIGS. 6, 7) which makes the choice of the best miRNA combinations for gastric cancer diagnosis challenging.

In view of the complexity of the task, it was decided that the present study has to identify panels of miRNA with the highest AUC using sequence forward floating search algorithm. The state-of-the art linear support vector machine, a well utilized and recognized modeling tool for the construction of panels of variables, was also known to be used in the art to aid in the selection of the combinations of miRNAs. The model yields a score based on a linear formula accounting for the expression level of each member and their weightages. These linear models are easily accepted and applied in the clinical practice.

A critical requirement for the success of such process is the availability of high quality data. The quantitative data of all the detected miRNAs in a large number of well-defined clinical samples not only improved the accuracy as well as precision of the result but also ensured the consistency of the identified biomarker panels for further clinical application using qPCR.

With the large number of clinical samples (500+), the issue of over-fitting of data in modeling was minimized as there were only 191 candidate features to be selected from. In addition, to ensure the veracity of the result, multiple times of four fold cross validation were carried out to test the performance of the identified biomarker panel based on the discovery set (¾ of the samples at each fold) in an independent set of validation samples (the rest ¼ of the samples at each fold). During the cross validation process, the samples were matched for sex, subtype and stage.

The boxplots representative of the results (the AUC of the biomarker panel in both discovery phase and validation phase) were shown in FIG. 10. As predicted, there was a decrease in AUC values with the validation set for each search (0.04-0.06). Although the size of the box was larger with data in the validation phase, indicative of a spread of values, the difference was ≤0.1 AUC values. This spread of values was even tighter (<0.05) when the number of biomarkers included in the analysis was higher than 6. This observation indicated that a more robust result was obtained with 6 or more miRNAs.

A more quantitative representation of the results was shown in FIG. 11 where there were no improvements on the AUC values were observed when the numbers of biomarkers included in the analyses were greater than seven. Although the difference between six miRNAs and seven miRNAs biomarker panels was statically significant, the improvement was a mere 0.02 in AUC values. Thus, an AUC value of 0.855 using 6 miRNAs panel is sufficient for clinical use.

IV, Composition of Multivariant-miRNA Biomarker Panels

To examine the composition of multivariant biomarker panels, the occurrence of miRNAs in all the panels containing 6-10 miRNAs was counted, where the panels with the top 10% and bottom 10% AUC were excluded. The exclusion of the top 10% and bottom 10% AUC was carried out to avoid counting of falsely discovered biomarkers due to fitting of inaccurate data from subpopulations generated by the randomization process in cross-validation analysis. Excluding these miRNAs with lesser than four counts, a total of 55 miRNA were selected in the discovery process (Table 12) where the expression of 43 of these were also found to be significantly altered in cancers. The inclusion of 12 others, although not altered in cancers, was found to significantly improve the AUC values. Without a direct and quantitative measurement of all miRNA targets, these miRNAs would never have been selected in high-through put screening methods (microarray, sequencing) and would have been excluded for qPCR validation. These miRNAs were not selected randomly as the top two miRNA (hsa-miR-532-5p, hsa-miR-30e-5p) were consistently found in 57.8% and 48.4% of the panels.

TABLE 12

MiRNAs identified in multivariant biomarker panel identification process

| | | | Changes in various stages of cancers | | | |
|---|---|---|---|---|---|---|
| | Prevalence | stage 1 | stage 2 | stage 3 | stage 4 | all stages |
| Significant group | | | | | | |
| hsa-miR-21-5p | 87.4% | No | Yes | Yes | Yes | Yes |
| hsa-miR-103a-3p | 87.0% | Yes | No | No | No | No |
| hsa-miR-20a-5p | 69.3% | No | Yes | No | Yes | Yes |
| hsa-miR-181a-5p | 39.4% | No | No | No | Yes | Yes |
| hsa-miR-142-5p | 32.1% | Yes | Yes | No | Yes | Yes |
| hsa-miR-27a-5p | 29.6% | Yes | Yes | Yes | Yes | Yes |
| hsa-miR-26a-5p | 27.4% | Yes | No | No | Yes | Yes |
| hsa-miR-17-5p | 26.4% | No | Yes | No | Yes | Yes |
| hsa-miR-616-5p | 23.1% | No | No | Yes | Yes | Yes |
| hsa-miR-30a-5p | 20.9% | No | No | Yes | Yes | Yes |
| hsa-miR-484 | 17.3% | No | No | No | Yes | No |
| hsa-miR-423-5p | 15.5% | No | Yes | Yes | No | Yes |
| hsa-miR-4306 | 13.4% | No | Yes | Yes | Yes | Yes |
| hsa-miR-590-5p | 11.6% | Yes | No | Yes | Yes | Yes |
| hsa-miR-362-5p | 11.2% | Yes | No | No | No | No |
| hsa-miR-106b-3p | 9.7% | Yes | Yes | No | Yes | Yes |
| hsa-miR-497-5p | 8.3% | No | No | No | Yes | No |
| hsa-miR-18b-5p | 7.9% | No | Yes | Yes | Yes | Yes |
| hsa-miR-122-5p | 6.9% | No | No | No | Yes | Yes |
| hsa-miR-200b-3p | 6.1% | No | No | No | Yes | No |
| hsa-miR-197-3p | 6.1% | No | Yes | Yes | Yes | Yes |
| hsa-miR-486-5p | 5.1% | No | No | No | No | Yes |
| hsa-miR-99a-5p | 5.1% | No | No | No | Yes | Yes |
| hsa-miR-885-5p | 4.3% | No | Yes | No | Yes | Yes |
| hsa-miR-598 | 3.2% | No | Yes | Yes | Yes | Yes |
| hsa-miR-454-3p | 2.9% | Yes | No | No | No | No |
| hsa-miR-130a-3p | 2.9% | No | No | Yes | No | No |
| hsa-miR-29c-3p | 2.9% | Yes | Yes | No | Yes | Yes |
| hsa-miR-126-3p | 2.9% | No | Yes | Yes | Yes | Yes |
| hsa-miR-107 | 2.5% | No | Yes | Yes | Yes | Yes |
| hsa-miR-140-5p | 2.2% | No | Yes | Yes | Yes | Yes |
| hsa-miR-150-5p | 2.2% | No | No | No | Yes | No |
| hsa-miR-30d-5p | 2.2% | No | No | No | Yes | No |
| hsa-miR-10b-5p | 2.2% | No | No | No | Yes | No |
| hsa-miR-532-3p | 2.2% | No | Yes | Yes | No | Yes |
| hsa-miR-23a-5p | 2.2% | No | Yes | Yes | Yes | Yes |
| hsa-miR-29b-3p | 1.8% | Yes | Yes | No | Yes | Yes |
| hsa-miR-21-3p | 1.8% | Yes | No | No | No | Yes |
| hsa-miR-148a-3p | 1.8% | No | Yes | Yes | Yes | Yes |
| hsa-miR-136-5p | 1.8% | Yes | No | No | Yes | Yes |
| hsa-miR-1280 | 1.4% | No | Yes | Yes | Yes | Yes |
| hsa-miR-16-5p | 1.4% | No | Yes | No | No | No |
| hsa-miR-223-3p | 1.4% | No | Yes | Yes | Yes | Yes |
| Insignificant group | | | | | | |
| hsa-miR-532-5p | 57.8% | No | No | No | No | No |
| hsa-miR-30e-5p | 48.4% | No | No | No | No | No |
| hsa-miR-340-5p | 11.2% | No | No | No | No | No |
| hsa-miR-23b-3p | 4.0% | No | No | No | No | No |

TABLE 12-continued

MiRNAs identified in multivariant biomarker panel identification process

| | | | Changes in various stages of cancers | | | |
|---|---|---|---|---|---|---|
| | Prevalence | stage 1 | stage 2 | stage 3 | stage 4 | all stages |
| hsa-miR-27b-3p | 2.2% | No | No | No | No | No |
| hsa-miR-224-5p | 2.2% | No | No | No | No | No |
| hsa-miR-185-5p | 1.8% | No | No | No | No | No |
| hsa-miR-320d | 1.4% | No | No | No | No | No |
| hsa-miR-374a-5p | 1.4% | No | No | No | No | No |
| hsa-miR-584-5p | 1.4% | No | No | No | No | No |
| hsa-miR-194-5p | 1.4% | No | No | No | No | No |
| hsa-miR-34a-5p | 1.4% | No | No | No | No | No |

The miRNAs selected to form the multivariate panels (Table 12) showed variability in detecting cancer at various stages (Tables 8-11). For the top 10 frequently chosen miRNAs in the list with occurrence higher than 20%, only three of the them were found to be commonly regulated in more than two different stages of cancers (hsa-miR-21-5p, hsa-miR-27a-5p, hsa-miR-142-5p) while for the rest, hsa-miR-103a-3p was only significant for stage 1, hsa-miR-181a-5p was only significant for stage 4, hsa-miR-26a-5p was significant for stage 1&4 hsa-miR-20a-5p and hsa-miR-17-5p were significant for stage 2 & 4 and hsa-miR-616-5p and hsa-miR-30a-5p were significant for stage 3 & 4. Excluding stage 4, where large numbers of miRNAs overlapped with lists for 3 other stages (FIG. 9), two specific miRNAs for each of stage 1-3 were frequently selected.

When comparing the identities of the chosen miRNAs for multivariate panels and single miRNA as diagnostic markers, they were not necessarily the same. For example, the top down-regulated (hsa-miR-99b-5p) miRNA for all cancers (FIG. 5) were not included in the list. Hence, it was not possible to merely to combine the best biomarker identified for various stages to form the optimal biomarker panel but rather a panel of markers providing complementary information that gives the best result.

Interestingly, five miRNAs were frequently selected for the multivariate panels (with >48% prevalence, see Table 12). Three of these were cancer specific (hsa-miR-21-5p, hsa-miR-103a-3p and hsa-miR-20a-5p) and two were from the other group (insignificant group; hsa-miR-532-5p and hsa-miR-30e-5p). The co-occurrence of these 5 miRNAs in all multivariant panels (Table 13) was analyzed and it was found that 85.9% of the panels had either hsa-miR-532-5p or hsa-miR-30e-5p. Thus, the use of either one of these two miRNAs may be sufficiently useful to increase the AUC values in the multivariate index panel.

In total, 93.8% of the miRNA biomarker panel had at least one miRNA from each group. Thus, in one example, the multivariate method for determining the likelihood of a subject having a gastric cancer may comprise at least one miRNA from each of these two frequently selected miRNA groups.

TABLE 13

Occurrence of frequently selected miRNAs

| | | Group: hsa-21-5p, -103a-3p, -20a-5p | | | | |
|---|---|---|---|---|---|---|
| | | n = 0 | n = 1 | n = 2 | n = 3 | sum |
| Group: hsa-miR-532-5p, -30e-5p | n = 0 | 0.7% | 1.1% | 2.2% | 0.0% | 4.0% |
| | n = 1 | 1.4% | 7.6% | 26.0% | 50.9% | 85.9% |
| | n = 2 | 0.0% | 0.7% | 2.9% | 6.5% | 10.1% |
| | sum | 2.2% | 9.4% | 31.0% | 57.4% | |

Calculation of Cancer Risk Score

MiRNAs can be combined to form a biomarker panel to calculate the cancer risk score (Formula 1). For example, the 12 miRNAs frequently selected in the multivariant biomarker panel identification process with prevalence >20% (Table 21) can be combined to form a biomarker panel to calculate the cancer risk score. The formula here demonstrates the use of a linear model for gastric cancer risk prediction, where the cancer risk score (unique for each subject) indicates the likelihood of a subject having gastric cancer. This is calculated by the summing the weighted measurements for the 12 miRNAs and a constant of 50.

$$\text{cancer risk score} = 50 + \sum_{i=1}^{12} K_i \times \log_2 \text{copy\_miRNA}_i \quad \text{Formula 1}$$

$\log_2$ copy_miRNA$_i$—log transformed copy numbers (copy/ml of serum) of the 12 individual miRNAs'. $K_i$—the coefficients used to weight multiple miRNA targets which can be found in Table 21. The values of $K_i$ were optimized with support vector machine method and scaled to range from 0 to 100. Subjects with cancer risk score lower than 0 will be considered as 0 and subjects with cancer risk score higher than 100 will be considered as 100.

TABLE 21

12 MiRNAs frequently selected in the multivariant biomarker panel identification process with prevalence > 20%

| miRNA$_i$ | K$_i$ |
|---|---|
| hsa-miR-21-5p | 13.9 |
| hsa-miR-103a-3p | −13.1 |
| hsa-miR-20a-5p | 13.3 |
| hsa-miR-181a-5p | −5.7 |
| hsa-miR-142-5p | 4.4 |
| hsa-miR-27a-5p | 1.9 |
| hsa-miR-26a-5p | −5.8 |
| hsa-miR-17-5p | 6.9 |
| hsa-miR-616-5p | 3.3 |
| hsa-miR-30a-5p | −4.2 |
| hsa-miR-532-5p | −6.1 |
| hsa-miR-30e-5p | −10.7 |

The control and cancer subjects in this studies have different cancer risk score values calculated based on the formula (FIG. 15A). The fitted probability distributions of the cancer risk scores for the control and cancer subjects can be found in FIG. 15B where a clear separation between the two groups can be found. In this study, the control subjects were non-cancer subjects selected from the high risk population which has a probability of 0.0067 to have gastric cancer. Based on this prior probability and the fitted probability distributions in FIG. 15B, the probability (risk) of an unknown subject having cancer can be calculated based on their cancer risk score values (FIG. 15C). With higher score, the subject has higher risk of having gastric cancer. Furthermore, the cancer risk score can tell the fold change of the probability (risk) of an unknown subject having gastric cancer compared to the cancer incidence rate in high risk population (FIG. 15D). For example, an unknown high risk subject having cancer risk score of 70 will have 14.6% probability to have gastric cancer which is about 22 times higher than the average risk of the high risk population.

Further applying two threshold values at 40 and 70, the subjects can be defined into three categories based on the cancer risk score FIG. 15C, D. Subjects with cancer risk score range of 0-40 belong to the low cancer risk group having 0.052% chance to have gastric cancer which is 13 fold lower than the average cancer incidence rate in high risk population. Subjects with cancer risk score range of 40-70 belong to the medium cancer risk group having 1.4% chance to have gastric cancer which is 2 times higher than the average cancer incidence rate in high risk population. Subjects with cancer risk score range of 70-100 belong to the high cancer risk group having 12.2% chance to have gastric cancer which is 18 folds higher than the average cancer incidence rate in high risk population.

The invention claimed is:

1. A method of treating a gastric cancer, wherein the method comprises:
   a) detecting or diagnosing a gastric cancer in a subject or determining a likelihood of a subject having said gastric cancer, wherein detecting or diagnosing said gastric cancer in the subject or determining the likelihood of the subject having said gastric cancer comprises:
      i) determining, in a non-cellular biofluid sample obtained from the subject, the expression level of at least six microRNAs (miRNAs) each having at least 90% sequence identity with an miRNA selected from the group consisting of hsa-miR-21-5p, hsa-miR-103a-3p, hsa-miR-20a-5p, hsa-miR-181a-5p, hsa-miR-142-5p, hsa-miR-27a-5p, hsa-miR-26a-5p, hsa-miR-17-5p, hsa-miR-616-5p, hsa-miR-30a-5p, hsa-miR-532-5p and hsa-miR-30e-5p,
      ii) determining differential expression of miRNA in the sample, as compared to a control in order to determine the subject to have said gastric cancer or diagnose the subject as having said gastric cancer or determine the likelihood of the subject to develop said gastric cancer, wherein the differential expression of miRNA is an upregulation or a downregulation of miRNA expression of the at least six miRNAs and
   b) treating the subject determined to have or diagnosed with said gastric cancer or having the likelihood of developing said gastric cancer with an anti-gastric cancer compound or a combination of anti-gastric cancer compounds.

2. The method according to claim 1, wherein the control is a sample obtained from a gastric cancer free subject.

3. The method according to claim 1, wherein the at least six miRNAs comprise hsa-miR-21-5p, hsa-miR-103a-3p, hsa-miR-20a-5p, hsa-miR-181a-5p, hsa-miR-142-5p, hsa-miR-27a-5p, hsa-miR-26a-5p, hsa-miR-17-5p, hsa-miR-616-5p, hsa-miR-30a-5p, hsa-miR-532-5p and hsa-miR-30e-5p.

4. The method according to claim 1, wherein the at least six miRNAs are identical to miRNAs selected from the group consisting of hsa-miR-21-5p, hsa-miR-103a-3p, hsa-miR-20a-5p, hsa-miR-181a-5p, hsa-miR-142-5p, hsa-miR-27a-5p, hsa-miR-26a-5p, hsa-miR-17-5p, hsa-miR-616-5p, hsa-miR-30a-5p, hsa-miR-532-5p and hsa-miR-30e-5p.

* * * * *

SEQUENCE LISTING

<160> NUMBER OF SEQ ID NOS: 191

<210> SEQ ID NO 1
<211> LENGTH: 22
<212> TYPE: RNA
<213> ORGANISM: Homo sapiens

<400> SEQUENCE: 1
cacccguaga accgaccuug cg                                            22

<210> SEQ ID NO 2
<211> LENGTH: 22
<212> TYPE: RNA
<213> ORGANISM: Homo sapiens

```
<400> SEQUENCE: 2
uccuguacug agcugccccg ag                                        22

<210> SEQ ID NO 3
<211> LENGTH: 21
<212> TYPE: RNA
<213> ORGANISM: Homo sapiens

<400> SEQUENCE: 3
aucacauugc cagggauuac c                                         21

<210> SEQ ID NO 4
<211> LENGTH: 21
<212> TYPE: RNA
<213> ORGANISM: Homo sapiens

<400> SEQUENCE: 4
uaccacaggg uagaaccacg g                                         21

<210> SEQ ID NO 5
<211> LENGTH: 21
<212> TYPE: RNA
<213> ORGANISM: Homo sapiens

<400> SEQUENCE: 5
uacaguacug ugauaacuga a                                         21

<210> SEQ ID NO 6
<211> LENGTH: 23
<212> TYPE: RNA
<213> ORGANISM: Homo sapiens

<400> SEQUENCE: 6
agcagcauug uacagggcua uca                                       23

<210> SEQ ID NO 7
<211> LENGTH: 22
<212> TYPE: RNA
<213> ORGANISM: Homo sapiens

<400> SEQUENCE: 7
cagugcaaug augaaagggc au                                        22

<210> SEQ ID NO 8
<211> LENGTH: 21
<212> TYPE: RNA
<213> ORGANISM: Homo sapiens

<400> SEQUENCE: 8
aauaauacau gguugaucuu u                                         21

<210> SEQ ID NO 9
<211> LENGTH: 22
<212> TYPE: RNA
<213> ORGANISM: Homo sapiens

<400> SEQUENCE: 9
uuuggucccc uucaaccagc ug                                        22

<210> SEQ ID NO 10
<211> LENGTH: 21
<212> TYPE: RNA
<213> ORGANISM: Homo sapiens
```

```
<400> SEQUENCE: 10
agcuacaucu ggcuacuggg u                                        21

<210> SEQ ID NO 11
<211> LENGTH: 19
<212> TYPE: RNA
<213> ORGANISM: Homo sapiens

<400> SEQUENCE: 11
aaaagcuggg uugagagga                                           19

<210> SEQ ID NO 12
<211> LENGTH: 22
<212> TYPE: RNA
<213> ORGANISM: Homo sapiens

<400> SEQUENCE: 12
uguaaacauc cucgacugga ag                                       22

<210> SEQ ID NO 13
<211> LENGTH: 23
<212> TYPE: RNA
<213> ORGANISM: Homo sapiens

<400> SEQUENCE: 13
aacauucaac gcugucggug agu                                      23

<210> SEQ ID NO 14
<211> LENGTH: 22
<212> TYPE: RNA
<213> ORGANISM: Homo sapiens

<400> SEQUENCE: 14
cagugguuuu acccuauggu ag                                       22

<210> SEQ ID NO 15
<211> LENGTH: 22
<212> TYPE: RNA
<213> ORGANISM: Homo sapiens

<400> SEQUENCE: 15
aucgggaaug ucguguccgc cc                                       22

<210> SEQ ID NO 16
<211> LENGTH: 22
<212> TYPE: RNA
<213> ORGANISM: Homo sapiens

<400> SEQUENCE: 16
ccgcacugug gguacuugcu gc                                       22

<210> SEQ ID NO 17
<211> LENGTH: 21
<212> TYPE: RNA
<213> ORGANISM: Homo sapiens

<400> SEQUENCE: 17
cugaccuaug aauugacagc c                                        21

<210> SEQ ID NO 18
<211> LENGTH: 22
<212> TYPE: RNA
```

<213> ORGANISM: Homo sapiens

<400> SEQUENCE: 18
caaauucgua ucuagggaa ua                                    22

<210> SEQ ID NO 19
<211> LENGTH: 23
<212> TYPE: RNA
<213> ORGANISM: Homo sapiens

<400> SEQUENCE: 19
caaagugcuu acagugcagg uag                                  23

<210> SEQ ID NO 20
<211> LENGTH: 22
<212> TYPE: RNA
<213> ORGANISM: Homo sapiens

<400> SEQUENCE: 20
gagcuuauuc auaaaagugc ag                                   22

<210> SEQ ID NO 21
<211> LENGTH: 22
<212> TYPE: RNA
<213> ORGANISM: Homo sapiens

<400> SEQUENCE: 21
uucuggaauu cugugugagg ga                                   22

<210> SEQ ID NO 22
<211> LENGTH: 22
<212> TYPE: RNA
<213> ORGANISM: Homo sapiens

<400> SEQUENCE: 22 uaaugcccu aaaaauccuu au                                    22

<210> SEQ ID NO 23
<211> LENGTH: 23
<212> TYPE: RNA
<213> ORGANISM: Homo sapiens

<400> SEQUENCE: 23
uaauccuugc uaccugggug aga                                  23

<210> SEQ ID NO 24
<211> LENGTH: 22
<212> TYPE: RNA
<213> ORGANISM: Homo sapiens

<400> SEQUENCE: 24
uauugcacau uacuaaguug ca                                   22

<210> SEQ ID NO 25
<211> LENGTH: 22
<212> TYPE: RNA
<213> ORGANISM: Homo sapiens

<400> SEQUENCE: 25
uuauaaagca augagacuga uu                                   22

<210> SEQ ID NO 26
<211> LENGTH: 22

```
<212> TYPE: RNA
<213> ORGANISM: Homo sapiens

<400> SEQUENCE: 26
auauaauaca accugcuaag ug                                              22

<210> SEQ ID NO 27
<211> LENGTH: 21
<212> TYPE: RNA
<213> ORGANISM: Homo sapiens

<400> SEQUENCE: 27
uucacagugg cuaaguuccg c                                               21

<210> SEQ ID NO 28
<211> LENGTH: 22
<212> TYPE: RNA
<213> ORGANISM: Homo sapiens

<400> SEQUENCE: 28
gugagucucu aagaaaagag ga                                              22

<210> SEQ ID NO 29
<211> LENGTH: 22
<212> TYPE: RNA
<213> ORGANISM: Homo sapiens

<400> SEQUENCE: 29
ggagaaauua uccuuggugu gu                                              22

<210> SEQ ID NO 30
<211> LENGTH: 21
<212> TYPE: RNA
<213> ORGANISM: Homo sapiens

<400> SEQUENCE: 30
aggggugcua ucugugauug a                                               21

<210> SEQ ID NO 31
<211> LENGTH: 22
<212> TYPE: RNA
<213> ORGANISM: Homo sapiens

<400> SEQUENCE: 31
ucaggcucag uccccucccg au                                              22

<210> SEQ ID NO 32
<211> LENGTH: 22
<212> TYPE: RNA
<213> ORGANISM: Homo sapiens

<400> SEQUENCE: 32
uaacagucua cagccauggu cg                                              22

<210> SEQ ID NO 33
<211> LENGTH: 21
<212> TYPE: RNA
<213> ORGANISM: Homo sapiens

<400> SEQUENCE: 33
ugguagacua uggaacguag g                                               21

<210> SEQ ID NO 34
```

```
<211> LENGTH: 22
<212> TYPE: RNA
<213> ORGANISM: Homo sapiens

<400> SEQUENCE: 34
acaggugagg uucuugggag cc                                              22

<210> SEQ ID NO 35
<211> LENGTH: 22
<212> TYPE: RNA
<213> ORGANISM: Homo sapiens

<400> SEQUENCE: 35
uagcaccauc ugaaaucggu ua                                              22

<210> SEQ ID NO 36
<211> LENGTH: 22
<212> TYPE: RNA
<213> ORGANISM: Homo sapiens

<400> SEQUENCE: 36
aauugcacgg uauccaucug ua                                              22

<210> SEQ ID NO 37
<211> LENGTH: 22
<212> TYPE: RNA
<213> ORGANISM: Homo sapiens

<400> SEQUENCE: 37
aucauagagg aaaauccaug uu                                              22

<210> SEQ ID NO 38
<211> LENGTH: 22
<212> TYPE: RNA
<213> ORGANISM: Homo sapiens

<400> SEQUENCE: 38
ugagaaccac gucugcucug ag                                              22

<210> SEQ ID NO 39
<211> LENGTH: 23
<212> TYPE: RNA
<213> ORGANISM: Homo sapiens

<400> SEQUENCE: 39
ucuuggagua ggucauuggg ugg                                             23

<210> SEQ ID NO 40
<211> LENGTH: 17
<212> TYPE: RNA
<213> ORGANISM: Homo sapiens

<400> SEQUENCE: 40
ucccaccgcu gccaccc                                                    17

<210> SEQ ID NO 41
<211> LENGTH: 23
<212> TYPE: RNA
<213> ORGANISM: Homo sapiens

<400> SEQUENCE: 41
agcagcauug uacagggcua uga                                             23
```

```
<210> SEQ ID NO 42
<211> LENGTH: 22
<212> TYPE: RNA
<213> ORGANISM: Homo sapiens

<400> SEQUENCE: 42
uggaguguga caauguguu ug                                         22

<210> SEQ ID NO 43
<211> LENGTH: 23
<212> TYPE: RNA
<213> ORGANISM: Homo sapiens

<400> SEQUENCE: 43 caaagucug uucgugcagg uag                                        23

<210> SEQ ID NO 44
<211> LENGTH: 22
<212> TYPE: RNA
<213> ORGANISM: Homo sapiens

<400> SEQUENCE: 44
cauugcacuu gucucggucu ga                                        22

<210> SEQ ID NO 45
<211> LENGTH: 23
<212> TYPE: RNA
<213> ORGANISM: Homo sapiens

<400> SEQUENCE: 45
ucuuugguua ucuagcugua uga                                       23

<210> SEQ ID NO 46
<211> LENGTH: 23
<212> TYPE: RNA
<213> ORGANISM: Homo sapiens

<400> SEQUENCE: 46
uucauuuggu auaaaccgcg auu                                       23

<210> SEQ ID NO 47
<211> LENGTH: 22
<212> TYPE: RNA
<213> ORGANISM: Homo sapiens

<400> SEQUENCE: 47
caucaucguc ucaaugagu cu                                         22

<210> SEQ ID NO 48
<211> LENGTH: 22
<212> TYPE: RNA
<213> ORGANISM: Homo sapiens

<400> SEQUENCE: 48
ugagaacuga auuccauggg uu                                        22

<210> SEQ ID NO 49
<211> LENGTH: 22
<212> TYPE: RNA
<213> ORGANISM: Homo sapiens

<400> SEQUENCE: 49
ggauaucauc auauacugua ag                                        22
```

```
<210> SEQ ID NO 50
<211> LENGTH: 22
<212> TYPE: RNA
<213> ORGANISM: Homo sapiens

<400> SEQUENCE: 50
uagcagcaca uaaugguuug ug                                              22

<210> SEQ ID NO 51
<211> LENGTH: 22
<212> TYPE: RNA
<213> ORGANISM: Homo sapiens

<400> SEQUENCE: 51
ucucccaacc cuuguaccag ug                                              22

<210> SEQ ID NO 52
<211> LENGTH: 21
<212> TYPE: RNA
<213> ORGANISM: Homo sapiens

<400> SEQUENCE: 52
ucagugcaug acagaacuug g                                               21

<210> SEQ ID NO 53
<211> LENGTH: 22
<212> TYPE: RNA
<213> ORGANISM: Homo sapiens

<400> SEQUENCE: 53
ugaccgauuu cuccuggugu uc                                              22

<210> SEQ ID NO 54
<211> LENGTH: 20
<212> TYPE: RNA
<213> ORGANISM: Homo sapiens

<400> SEQUENCE: 54
aaaagcuggg uugagagggu                                                 20

<210> SEQ ID NO 55
<211> LENGTH: 22
<212> TYPE: RNA
<213> ORGANISM: Homo sapiens

<400> SEQUENCE: 55
ucggauccgu cugagcuugg cu                                              22

<210> SEQ ID NO 56
<211> LENGTH: 22
<212> TYPE: RNA
<213> ORGANISM: Homo sapiens

<400> SEQUENCE: 56
cuagguaugg ucccagggau cc                                              22

<210> SEQ ID NO 57
<211> LENGTH: 21
<212> TYPE: RNA
<213> ORGANISM: Homo sapiens

<400> SEQUENCE: 57
acuggacuug gagucagaag g                                               21
```

```
<210> SEQ ID NO 58
<211> LENGTH: 22
<212> TYPE: RNA
<213> ORGANISM: Homo sapiens

<400> SEQUENCE: 58
uuauaauaca accugauaag ug                                              22

<210> SEQ ID NO 59
<211> LENGTH: 22
<212> TYPE: RNA
<213> ORGANISM: Homo sapiens

<400> SEQUENCE: 59
gaauguugcu cggugaaccc cu                                              22

<210> SEQ ID NO 60
<211> LENGTH: 22
<212> TYPE: RNA
<213> ORGANISM: Homo sapiens

<400> SEQUENCE: 60
uauguaacac gguccacuaa cc                                              22

<210> SEQ ID NO 61
<211> LENGTH: 22
<212> TYPE: RNA
<213> ORGANISM: Homo sapiens

<400> SEQUENCE: 61
cgucaacacu ugcugguuuc cu                                              22

<210> SEQ ID NO 62
<211> LENGTH: 22
<212> TYPE: RNA
<213> ORGANISM: Homo sapiens

<400> SEQUENCE: 62
augcugacau auuuacuaga gg                                              22

<210> SEQ ID NO 63
<211> LENGTH: 22
<212> TYPE: RNA
<213> ORGANISM: Homo sapiens

<400> SEQUENCE: 63
guucucccaa cguaagccca gc                                              22

<210> SEQ ID NO 64
<211> LENGTH: 21
<212> TYPE: RNA
<213> ORGANISM: Homo sapiens

<400> SEQUENCE: 64
gcccugaccu guccuguucu g                                               21

<210> SEQ ID NO 65
<211> LENGTH: 22
<212> TYPE: RNA
<213> ORGANISM: Homo sapiens

<400> SEQUENCE: 65
```
aauccuuugu cccuggguga ga					22

<210> SEQ ID NO 66
<211> LENGTH: 22
<212> TYPE: RNA
<213> ORGANISM: Homo sapiens

<400> SEQUENCE: 66
acucaaaacc cuucagugac uu					22

<210> SEQ ID NO 67
<211> LENGTH: 23
<212> TYPE: RNA
<213> ORGANISM: Homo sapiens

<400> SEQUENCE: 67
uagugcaaua uugcuuauag ggu					23

<210> SEQ ID NO 68
<211> LENGTH: 22
<212> TYPE: RNA
<213> ORGANISM: Homo sapiens

<400> SEQUENCE: 68
gucauacacg gcucuccucu cu					22

<210> SEQ ID NO 69
<211> LENGTH: 22
<212> TYPE: RNA
<213> ORGANISM: Homo sapiens

<400> SEQUENCE: 69
uuuggucccc uucaaccagc ua					22

<210> SEQ ID NO 70
<211> LENGTH: 22
<212> TYPE: RNA
<213> ORGANISM: Homo sapiens

<400> SEQUENCE: 70
caaagaauuc uccuuuuggg cu					22

<210> SEQ ID NO 71
<211> LENGTH: 23
<212> TYPE: RNA
<213> ORGANISM: Homo sapiens

<400> SEQUENCE: 71
caaagugcuc auagugcagg uag					23

<210> SEQ ID NO 72
<211> LENGTH: 22
<212> TYPE: RNA
<213> ORGANISM: Homo sapiens

<400> SEQUENCE: 72
uguaaacauc cccgacugga ag					22

<210> SEQ ID NO 73
<211> LENGTH: 22
<212> TYPE: RNA
<213> ORGANISM: Homo sapiens

<400> SEQUENCE: 73
uuuguucguu cggcucgcgu ga					22

<210> SEQ ID NO 74
<211> LENGTH: 22
<212> TYPE: RNA
<213> ORGANISM: Homo sapiens

<400> SEQUENCE: 74
uagcagcacg uaaauauugg cg					22

<210> SEQ ID NO 75
<211> LENGTH: 21
<212> TYPE: RNA
<213> ORGANISM: Homo sapiens

<400> SEQUENCE: 75
uaaagugcug acagugcaga u						21

<210> SEQ ID NO 76
<211> LENGTH: 22
<212> TYPE: RNA
<213> ORGANISM: Homo sapiens

<400> SEQUENCE: 76
ucuacagugc acgugucucc ag					22

<210> SEQ ID NO 77
<211> LENGTH: 22
<212> TYPE: RNA
<213> ORGANISM: Homo sapiens

<400> SEQUENCE: 77
uaacacuguc ugguaaagau gg					22

<210> SEQ ID NO 78
<211> LENGTH: 22
<212> TYPE: RNA
<213> ORGANISM: Homo sapiens

<400> SEQUENCE: 78
uggagagaaa ggcaguuccu ga					22

<210> SEQ ID NO 79
<211> LENGTH: 23
<212> TYPE: RNA
<213> ORGANISM: Homo sapiens

<400> SEQUENCE: 79
aacauucauu gcugucggug ggu					23

<210> SEQ ID NO 80
<211> LENGTH: 22
<212> TYPE: RNA
<213> ORGANISM: Homo sapiens

<400> SEQUENCE: 80
acaguagucu gcacauuggu ua					22

<210> SEQ ID NO 81
<211> LENGTH: 23
<212> TYPE: RNA
<213> ORGANISM: Homo sapiens

```
<400> SEQUENCE: 81
ugugcaaauc caugcaaaac uga                                    23

<210> SEQ ID NO 82
<211> LENGTH: 22
<212> TYPE: RNA
<213> ORGANISM: Homo sapiens

<400> SEQUENCE: 82
ucagugcauc acagaacuuu gu                                     22

<210> SEQ ID NO 83
<211> LENGTH: 23
<212> TYPE: RNA
<213> ORGANISM: Homo sapiens

<400> SEQUENCE: 83
uagcaccauu ugaaaucagu guu                                    23

<210> SEQ ID NO 84
<211> LENGTH: 22
<212> TYPE: RNA
<213> ORGANISM: Homo sapiens

<400> SEQUENCE: 84
aacaauaucc uggugcugag ug                                     22

<210> SEQ ID NO 85
<211> LENGTH: 22
<212> TYPE: RNA
<213> ORGANISM: Homo sapiens

<400> SEQUENCE: 85
uuaugguuug ccugggacug ag                                     22

<210> SEQ ID NO 86
<211> LENGTH: 22
<212> TYPE: RNA
<213> ORGANISM: Homo sapiens

<400> SEQUENCE: 86
gaaguuguuc gugguggauu cg                                     22

<210> SEQ ID NO 87
<211> LENGTH: 21
<212> TYPE: RNA
<213> ORGANISM: Homo sapiens

<400> SEQUENCE: 87
cuagacugaa gcuccuugag g                                      21

<210> SEQ ID NO 88
<211> LENGTH: 19
<212> TYPE: RNA
<213> ORGANISM: Homo sapiens

<400> SEQUENCE: 88
uggauuuuug gaucaggga                                         19

<210> SEQ ID NO 89
<211> LENGTH: 22
<212> TYPE: RNA
<213> ORGANISM: Homo sapiens
```

-continued

<400> SEQUENCE: 89
uaauacugcc ugguaaugau ga                                              22

<210> SEQ ID NO 90
<211> LENGTH: 21
<212> TYPE: RNA
<213> ORGANISM: Homo sapiens

<400> SEQUENCE: 90
uaguagaccg uauagcguac g                                               21

<210> SEQ ID NO 91
<211> LENGTH: 21
<212> TYPE: RNA
<213> ORGANISM: Homo sapiens

<400> SEQUENCE: 91
cauuauuacu uuugguacgc g                                               21

<210> SEQ ID NO 92
<211> LENGTH: 22
<212> TYPE: RNA
<213> ORGANISM: Homo sapiens

<400> SEQUENCE: 92
caguuaucac agugcugaug cu                                              22

<210> SEQ ID NO 93
<211> LENGTH: 22
<212> TYPE: RNA
<213> ORGANISM: Homo sapiens

<400> SEQUENCE: 93
ucccugagac ccuaacuugu ga                                              22

<210> SEQ ID NO 94
<211> LENGTH: 24
<212> TYPE: RNA
<213> ORGANISM: Homo sapiens

<400> SEQUENCE: 94
aauccuugga accaggugu gagu                                             24

<210> SEQ ID NO 95
<211> LENGTH: 22
<212> TYPE: RNA
<213> ORGANISM: Homo sapiens

<400> SEQUENCE: 95
uucaccaccu ucuccaccca gc                                              22

<210> SEQ ID NO 96
<211> LENGTH: 23
<212> TYPE: RNA
<213> ORGANISM: Homo sapiens

<400> SEQUENCE: 96
agcuacauug ucugcugggu uuc                                             23

<210> SEQ ID NO 97
<211> LENGTH: 22
<212> TYPE: RNA

```
<213> ORGANISM: Homo sapiens

<400> SEQUENCE: 97
aaugcacccg ggcaaggauu cu                                          22

<210> SEQ ID NO 98
<211> LENGTH: 21
<212> TYPE: RNA
<213> ORGANISM: Homo sapiens

<400> SEQUENCE: 98
uccgguucuc agggcuccac c                                           21

<210> SEQ ID NO 99
<211> LENGTH: 22
<212> TYPE: RNA
<213> ORGANISM: Homo sapiens

<400> SEQUENCE: 99
accacugacc guugacugua cc                                          22

<210> SEQ ID NO 100
<211> LENGTH: 22
<212> TYPE: RNA
<213> ORGANISM: Homo sapiens

<400> SEQUENCE: 100
auaaagcuag auaaccgaaa gu                                          22

<210> SEQ ID NO 101
<211> LENGTH: 22
<212> TYPE: RNA
<213> ORGANISM: Homo sapiens

<400> SEQUENCE: 101
aacuguuugc agaggaaacu ga                                          22

<210> SEQ ID NO 102
<211> LENGTH: 22
<212> TYPE: RNA
<213> ORGANISM: Homo sapiens

<400> SEQUENCE: 102
uacgucaucg uugucaucgu ca                                          22

<210> SEQ ID NO 103
<211> LENGTH: 22
<212> TYPE: RNA
<213> ORGANISM: Homo sapiens

<400> SEQUENCE: 103
aaaagcuggg uugagagggc aa                                          22

<210> SEQ ID NO 104
<211> LENGTH: 22
<212> TYPE: RNA
<213> ORGANISM: Homo sapiens

<400> SEQUENCE: 104
cuggcccucu cugcccuucc gu                                          22

<210> SEQ ID NO 105
<211> LENGTH: 21
```

<212> TYPE: RNA
<213> ORGANISM: Homo sapiens

<400> SEQUENCE: 105
aggaggcagc gcucucagga c                                              21

<210> SEQ ID NO 106
<211> LENGTH: 22
<212> TYPE: RNA
<213> ORGANISM: Homo sapiens

<400> SEQUENCE: 106
ugugacuggu ugaccagagg gg                                             22

<210> SEQ ID NO 107
<211> LENGTH: 22
<212> TYPE: RNA
<213> ORGANISM: Homo sapiens

<400> SEQUENCE: 107
cagugcaaug uuaaaagggc au                                             22

<210> SEQ ID NO 108
<211> LENGTH: 22
<212> TYPE: RNA
<213> ORGANISM: Homo sapiens

<400> SEQUENCE: 108
uagcuuauca gacugauguu ga                                             22

<210> SEQ ID NO 109
<211> LENGTH: 22
<212> TYPE: RNA
<213> ORGANISM: Homo sapiens

<400> SEQUENCE: 109
cagcagcaau ucauguuuug aa                                             22

<210> SEQ ID NO 110
<211> LENGTH: 22
<212> TYPE: RNA
<213> ORGANISM: Homo sapiens

<400> SEQUENCE: 110
aacccguaga uccgaucuug ug                                             22

<210> SEQ ID NO 111
<211> LENGTH: 23
<212> TYPE: RNA
<213> ORGANISM: Homo sapiens

<400> SEQUENCE: 111
acugcccuaa gugcuccuuc ugg                                            23

<210> SEQ ID NO 112
<211> LENGTH: 21
<212> TYPE: RNA
<213> ORGANISM: Homo sapiens

<400> SEQUENCE: 112
uagcagcaca gaaauauugg c                                              21

<210> SEQ ID NO 113

```
<211> LENGTH: 22
<212> TYPE: RNA
<213> ORGANISM: Homo sapiens

<400> SEQUENCE: 113
uccuucauuc caccggaguc ug                                              22

<210> SEQ ID NO 114
<211> LENGTH: 22
<212> TYPE: RNA
<213> ORGANISM: Homo sapiens

<400> SEQUENCE: 114
uggaauguaa ggaagugugu gg                                              22

<210> SEQ ID NO 115
<211> LENGTH: 22
<212> TYPE: RNA
<213> ORGANISM: Homo sapiens

<400> SEQUENCE: 115
augcaccugg gcaaggauuc ug                                              22

<210> SEQ ID NO 116
<211> LENGTH: 23
<212> TYPE: RNA
<213> ORGANISM: Homo sapiens

<400> SEQUENCE: 116
uaaggugcau cuagugcagu uag                                             23

<210> SEQ ID NO 117
<211> LENGTH: 23
<212> TYPE: RNA
<213> ORGANISM: Homo sapiens

<400> SEQUENCE: 117
aacauucauu guugucggug ggu                                             23

<210> SEQ ID NO 118
<211> LENGTH: 23
<212> TYPE: RNA
<213> ORGANISM: Homo sapiens

<400> SEQUENCE: 118
ugagcgccuc gacgacagag ccg                                             23

<210> SEQ ID NO 119
<211> LENGTH: 22
<212> TYPE: RNA
<213> ORGANISM: Homo sapiens

<400> SEQUENCE: 119
acugcugagc uagcacuucc cg                                              22

<210> SEQ ID NO 120
<211> LENGTH: 23
<212> TYPE: RNA
<213> ORGANISM: Homo sapiens

<400> SEQUENCE: 120
uacccuguag aaccgaauuu gug                                             23
```

```
<210> SEQ ID NO 121
<211> LENGTH: 21
<212> TYPE: RNA
<213> ORGANISM: Homo sapiens

<400> SEQUENCE: 121
cagcagcaca cugugguuug u                                              21

<210> SEQ ID NO 122
<211> LENGTH: 21
<212> TYPE: RNA
<213> ORGANISM: Homo sapiens

<400> SEQUENCE: 122
uucacagugg cuaaguucug c                                              21

<210> SEQ ID NO 123
<211> LENGTH: 21
<212> TYPE: RNA
<213> ORGANISM: Homo sapiens

<400> SEQUENCE: 123
ucacagugaa ccggucucuu u                                              21

<210> SEQ ID NO 124
<211> LENGTH: 22
<212> TYPE: RNA
<213> ORGANISM: Homo sapiens

<400> SEQUENCE: 124
uauggcacug guagaauuca cu                                             22

<210> SEQ ID NO 125
<211> LENGTH: 22
<212> TYPE: RNA
<213> ORGANISM: Homo sapiens

<400> SEQUENCE: 125
aagcugccag uugaagaacu gu                                             22

<210> SEQ ID NO 126
<211> LENGTH: 22
<212> TYPE: RNA
<213> ORGANISM: Homo sapiens

<400> SEQUENCE: 126
uucaaguaau ccaggauagg cu                                             22

<210> SEQ ID NO 127
<211> LENGTH: 22
<212> TYPE: RNA
<213> ORGANISM: Homo sapiens

<400> SEQUENCE: 127
ugucaguuug ucaaauaccc ca                                             22

<210> SEQ ID NO 128
<211> LENGTH: 21
<212> TYPE: RNA
<213> ORGANISM: Homo sapiens

<400> SEQUENCE: 128
uggguuuacg uugggagaac u                                              21
```

```
<210> SEQ ID NO 129
<211> LENGTH: 22
<212> TYPE: RNA
<213> ORGANISM: Homo sapiens

<400> SEQUENCE: 129
uauugcacuu gucccggccu gu                                              22

<210> SEQ ID NO 130
<211> LENGTH: 22
<212> TYPE: RNA
<213> ORGANISM: Homo sapiens

<400> SEQUENCE: 130
cugguuucac augguggcuu ag                                              22

<210> SEQ ID NO 131
<211> LENGTH: 21
<212> TYPE: RNA
<213> ORGANISM: Homo sapiens

<400> SEQUENCE: 131
caacaccagu cgaugggcug u                                               21

<210> SEQ ID NO 132
<211> LENGTH: 23
<212> TYPE: RNA
<213> ORGANISM: Homo sapiens

<400> SEQUENCE: 132
cccaguguuc agacuaccug uuc                                             23

<210> SEQ ID NO 133
<211> LENGTH: 22
<212> TYPE: RNA
<213> ORGANISM: Homo sapiens

<400> SEQUENCE: 133
ucagugcacu acagaacuuu gu                                              22

<210> SEQ ID NO 134
<211> LENGTH: 22
<212> TYPE: RNA
<213> ORGANISM: Homo sapiens

<400> SEQUENCE: 134
ugggucuuug cgggcgagau ga                                              22

<210> SEQ ID NO 135
<211> LENGTH: 22
<212> TYPE: RNA
<213> ORGANISM: Homo sapiens

<400> SEQUENCE: 135
agggcuuagc ugcuugugag ca                                              22

<210> SEQ ID NO 136
<211> LENGTH: 23
<212> TYPE: RNA
<213> ORGANISM: Homo sapiens

<400> SEQUENCE: 136
uaauacugcc ggguaaugau gga                                             23
```

```
<210> SEQ ID NO 137
<211> LENGTH: 23
<212> TYPE: RNA
<213> ORGANISM: Homo sapiens

<400> SEQUENCE: 137
uaaagugcuu auagugcagg uag                                              23

<210> SEQ ID NO 138
<211> LENGTH: 22
<212> TYPE: RNA
<213> ORGANISM: Homo sapiens

<400> SEQUENCE: 138
uguaacagca acuccaugug ga                                               22

<210> SEQ ID NO 139
<211> LENGTH: 22
<212> TYPE: RNA
<213> ORGANISM: Homo sapiens

<400> SEQUENCE: 139
ccucccacac ccaaggcuug ca                                               22

<210> SEQ ID NO 140
<211> LENGTH: 23
<212> TYPE: RNA
<213> ORGANISM: Homo sapiens

<400> SEQUENCE: 140
ugugcaaauc uaugcaaaac uga                                              23

<210> SEQ ID NO 141
<211> LENGTH: 21
<212> TYPE: RNA
<213> ORGANISM: Homo sapiens

<400> SEQUENCE: 141
cauaaaguag aaagcacuac u                                                21

<210> SEQ ID NO 142
<211> LENGTH: 20
<212> TYPE: RNA
<213> ORGANISM: Homo sapiens

<400> SEQUENCE: 142
uacaguauag augauguacu                                                  20

<210> SEQ ID NO 143
<211> LENGTH: 23
<212> TYPE: RNA
<213> ORGANISM: Homo sapiens

<400> SEQUENCE: 143
guccaguuuu cccaggaauc ccu                                              23

<210> SEQ ID NO 144
<211> LENGTH: 23
<212> TYPE: RNA
<213> ORGANISM: Homo sapiens

<400> SEQUENCE: 144
```

```
uacccuguag auccgaauuu gug                                              23

<210> SEQ ID NO 145
<211> LENGTH: 21
<212> TYPE: RNA
<213> ORGANISM: Homo sapiens

<400> SEQUENCE: 145
aucacauugc cagggauuuc c                                                21

<210> SEQ ID NO 146
<211> LENGTH: 22
<212> TYPE: RNA
<213> ORGANISM: Homo sapiens

<400> SEQUENCE: 146
gggguuccug gggaugggau uu                                               22

<210> SEQ ID NO 147
<211> LENGTH: 22
<212> TYPE: RNA
<213> ORGANISM: Homo sapiens

<400> SEQUENCE: 147
cgaaucauua uuugcugcuc ua                                               22

<210> SEQ ID NO 148
<211> LENGTH: 23
<212> TYPE: RNA
<213> ORGANISM: Homo sapiens

<400> SEQUENCE: 148
cagugcaaua guauugucaa agc                                              23

<210> SEQ ID NO 149
<211> LENGTH: 22
<212> TYPE: RNA
<213> ORGANISM: Homo sapiens

<400> SEQUENCE: 149
uacccauugc auaucggagu ug                                               22

<210> SEQ ID NO 150
<211> LENGTH: 22
<212> TYPE: RNA
<213> ORGANISM: Homo sapiens

<400> SEQUENCE: 150
uguaaacauc cuacacucag cu                                               22

<210> SEQ ID NO 151
<211> LENGTH: 22
<212> TYPE: RNA
<213> ORGANISM: Homo sapiens

<400> SEQUENCE: 151
uguaaacauc cuugacugga ag                                               22

<210> SEQ ID NO 152
<211> LENGTH: 23
<212> TYPE: RNA
<213> ORGANISM: Homo sapiens

<400> SEQUENCE: 152
```

```
agugccugag ggaguaagag ccc                                              23

<210> SEQ ID NO 153
<211> LENGTH: 23
<212> TYPE: RNA
<213> ORGANISM: Homo sapiens

<400> SEQUENCE: 153
aaugacacga ucacucccgu uga                                              23

<210> SEQ ID NO 154
<211> LENGTH: 17
<212> TYPE: RNA
<213> ORGANISM: Homo sapiens

<400> SEQUENCE: 154
uggagagaaa ggcagua                                                     17

<210> SEQ ID NO 155
<211> LENGTH: 22
<212> TYPE: RNA
<213> ORGANISM: Homo sapiens

<400> SEQUENCE: 155
caugccuuga guguaggacc gu                                               22

<210> SEQ ID NO 156
<211> LENGTH: 23
<212> TYPE: RNA
<213> ORGANISM: Homo sapiens

<400> SEQUENCE: 156
ucaagagcaa uaacgaaaaa ugu                                              23

<210> SEQ ID NO 157
<211> LENGTH: 22
<212> TYPE: RNA
<213> ORGANISM: Homo sapiens

<400> SEQUENCE: 157
aagacgggag gaaagaaggg ag                                               22

<210> SEQ ID NO 158
<211> LENGTH: 22
<212> TYPE: RNA
<213> ORGANISM: Homo sapiens

<400> SEQUENCE: 158
ucaccagccc uguguucccu ag                                               22

<210> SEQ ID NO 159
<211> LENGTH: 21
<212> TYPE: RNA
<213> ORGANISM: Homo sapiens

<400> SEQUENCE: 159
ugucuugcag gccgucaugc a                                                21

<210> SEQ ID NO 160
<211> LENGTH: 23
<212> TYPE: RNA
<213> ORGANISM: Homo sapiens
```

<400> SEQUENCE: 160
cgcauccccu agggcauugg ugu 23

<210> SEQ ID NO 161
<211> LENGTH: 22
<212> TYPE: RNA
<213> ORGANISM: Homo sapiens

<400> SEQUENCE: 161
aaucguacag ggucauccac uu 22

<210> SEQ ID NO 162
<211> LENGTH: 22
<212> TYPE: RNA
<213> ORGANISM: Homo sapiens

<400> SEQUENCE: 162
aaaccguuac cauuacugag uu 22

<210> SEQ ID NO 163
<211> LENGTH: 22
<212> TYPE: RNA
<213> ORGANISM: Homo sapiens

<400> SEQUENCE: 163
uuguacaugg uaggcuuuca uu 22

<210> SEQ ID NO 164
<211> LENGTH: 23
<212> TYPE: RNA
<213> ORGANISM: Homo sapiens

<400> SEQUENCE: 164
acuccauuug uuuugaugau gga 23

<210> SEQ ID NO 165
<211> LENGTH: 22
<212> TYPE: RNA
<213> ORGANISM: Homo sapiens

<400> SEQUENCE: 165
aucacauugc cagugauuac cc 22

<210> SEQ ID NO 166
<211> LENGTH: 22
<212> TYPE: RNA
<213> ORGANISM: Homo sapiens

<400> SEQUENCE: 166
uucaacgggu auuuauugag ca 22

<210> SEQ ID NO 167
<211> LENGTH: 23
<212> TYPE: RNA
<213> ORGANISM: Homo sapiens

<400> SEQUENCE: 167
ugaggggcag agagcgagac uuu 23

<210> SEQ ID NO 168
<211> LENGTH: 18
<212> TYPE: RNA
<213> ORGANISM: Homo sapiens

```
<400> SEQUENCE: 168
aaagcugggu ugagaagg                                                       18

<210> SEQ ID NO 169
<211> LENGTH: 21
<212> TYPE: RNA
<213> ORGANISM: Homo sapiens

<400> SEQUENCE: 169
caagucacua gugguuccgu u                                                   21

<210> SEQ ID NO 170
<211> LENGTH: 22
<212> TYPE: RNA
<213> ORGANISM: Homo sapiens

<400> SEQUENCE: 170
cacuagauug ugagcuccug ga                                                  22

<210> SEQ ID NO 171
<211> LENGTH: 22
<212> TYPE: RNA
<213> ORGANISM: Homo sapiens

<400> SEQUENCE: 171
uagcaccauu ugaaacggu ua                                                   22

<210> SEQ ID NO 172
<211> LENGTH: 20
<212> TYPE: RNA
<213> ORGANISM: Homo sapiens

<400> SEQUENCE: 172
ccucugggcc cuuccuccag                                                     20

<210> SEQ ID NO 173
<211> LENGTH: 21
<212> TYPE: RNA
<213> ORGANISM: Homo sapiens

<400> SEQUENCE: 173
aagccugccc ggcuccucgg g                                                   21

<210> SEQ ID NO 174
<211> LENGTH: 22
<212> TYPE: RNA
<213> ORGANISM: Homo sapiens

<400> SEQUENCE: 174
uccauuacac uacccugccu cu                                                  22

<210> SEQ ID NO 175
<211> LENGTH: 22
<212> TYPE: RNA
<213> ORGANISM: Homo sapiens

<400> SEQUENCE: 175
ugagaacuga auuccauagg cu                                                  22

<210> SEQ ID NO 176
<211> LENGTH: 22
<212> TYPE: RNA
```

<213> ORGANISM: Homo sapiens

<400> SEQUENCE: 176
uggcaguguc uuagcugguu gu                                    22

<210> SEQ ID NO 177
<211> LENGTH: 23
<212> TYPE: RNA
<213> ORGANISM: Homo sapiens

<400> SEQUENCE: 177
gcaaagcaca cggccugcag aga                                   23

<210> SEQ ID NO 178
<211> LENGTH: 22
<212> TYPE: RNA
<213> ORGANISM: Homo sapiens

<400> SEQUENCE: 178
uagguuaucc guguugccuu cg                                    22

<210> SEQ ID NO 179
<211> LENGTH: 23
<212> TYPE: RNA
<213> ORGANISM: Homo sapiens

<400> SEQUENCE: 179
caacggaauc ccaaaagcag cug                                   23

<210> SEQ ID NO 180
<211> LENGTH: 22
<212> TYPE: RNA
<213> ORGANISM: Homo sapiens

<400> SEQUENCE: 180
aacuggcccu caaagucccg cu                                    22

<210> SEQ ID NO 181
<211> LENGTH: 23
<212> TYPE: RNA
<213> ORGANISM: Homo sapiens

<400> SEQUENCE: 181
cagugcaaug auauugucaa agc                                   23

<210> SEQ ID NO 182
<211> LENGTH: 22
<212> TYPE: RNA
<213> ORGANISM: Homo sapiens

<400> SEQUENCE: 182
cuuucagucg gauguuuaca gc                                    22

<210> SEQ ID NO 183
<211> LENGTH: 22
<212> TYPE: RNA
<213> ORGANISM: Homo sapiens

<400> SEQUENCE: 183
aaaagcuggg uugagagggc ga                                    22

<210> SEQ ID NO 184
<211> LENGTH: 22

```
<212> TYPE: RNA
<213> ORGANISM: Homo sapiens

<400> SEQUENCE: 184
acaguagucu gcacauuggu ua                                              22

<210> SEQ ID NO 185
<211> LENGTH: 22
<212> TYPE: RNA
<213> ORGANISM: Homo sapiens

<400> SEQUENCE: 185
aaugcaccug ggcaaggauu ca                                              22

<210> SEQ ID NO 186
<211> LENGTH: 22
<212> TYPE: RNA
<213> ORGANISM: Homo sapiens

<400> SEQUENCE: 186
uuuugcgaug uguuccuaau au                                              22

<210> SEQ ID NO 187
<211> LENGTH: 22
<212> TYPE: RNA
<213> ORGANISM: Homo sapiens

<400> SEQUENCE: 187
aaacaaacau ggugcacuuc uu                                              22

<210> SEQ ID NO 188
<211> LENGTH: 22
<212> TYPE: RNA
<213> ORGANISM: Homo sapiens

<400> SEQUENCE: 188
ucguaccgug aguaauaaug cg                                              22

<210> SEQ ID NO 189
<211> LENGTH: 22
<212> TYPE: RNA
<213> ORGANISM: Homo sapiens

<400> SEQUENCE: 189
uagcagcaca ucaugguuua ca                                              22

<210> SEQ ID NO 190
<211> LENGTH: 23
<212> TYPE: RNA
<213> ORGANISM: Homo sapiens

<400> SEQUENCE: 190
ucccuguccu ccaggagcuc acg                                             23

<210> SEQ ID NO 191
<211> LENGTH: 21
<212> TYPE: RNA
<213> ORGANISM: Homo sapiens

<400> SEQUENCE: 191
gaacggcuuc auacaggagu u                                               21
```